United States Patent
Tonkovich et al.

(10) Patent No.: US 8,252,245 B2
(45) Date of Patent: Aug. 28, 2012

(54) PARTIAL BOILING IN MINI AND MICRO-CHANNELS

(75) Inventors: Anna Lee Tonkovich, Dublin, OH (US); David J. Hesse, Columbus, OH (US); Sean P. Fitzgerald, Columbus, OH (US); Bin Yang, Columbus, OH (US); Ravi Arora, New Albany, OH (US); Laura J. Silva, Dublin, OH (US); G. Bradley Chadwell, Reynoldsburg, OH (US); Kai Jarosch, Bexley, OH (US); Dongming Qiu, Bothell, WA (US)

(73) Assignee: Velocys, Inc., Plain City, OH (US)

(*) Notice: Subject to any disclaimer, the term of this patent is extended or adjusted under 35 U.S.C. 154(b) by 0 days.

(21) Appl. No.: 11/266,582

(22) Filed: Nov. 3, 2005

(65) Prior Publication Data
US 2006/0142401 A1    Jun. 29, 2006

Related U.S. Application Data

(60) Provisional application No. 60/624,860, filed on Nov. 3, 2004.

(51) Int. Cl.
*B01J 19/24* (2006.01)
*F28D 9/00* (2006.01)
*B01B 1/00* (2006.01)

(52) U.S. Cl. ........ 422/198; 422/601; 422/602; 422/603; 165/104.19; 165/104.21; 165/104.27

(58) Field of Classification Search ................. 422/198, 422/601–603; 165/104.19, 104.21, 104.27
See application file for complete search history.

(56) References Cited

U.S. PATENT DOCUMENTS

| | | | |
|---|---|---|---|
| 2,950,604 A * | 8/1960 | Gambill et al. | 62/5 |
| 4,624,299 A * | 11/1986 | Harding et al. | 165/104.19 |
| 4,795,618 A | 1/1989 | Laumen | |
| 5,209,291 A | 5/1993 | Taylor | |
| 5,607,616 A | 3/1997 | Minor et al. | |
| 5,904,424 A | 5/1999 | Schwesinger et al. | |
| 6,159,434 A | 12/2000 | Gonjo et al. | |
| 6,200,536 B1 | 3/2001 | Tonkovich et al. | |
| 7,035,104 B2 * | 4/2006 | Meyer | 361/700 |
| 2002/0031471 A1 | 3/2002 | Tonkovich et al. | |
| 2003/0062149 A1* | 4/2003 | Goodson et al. | 165/104.11 |
| 2003/0131972 A1* | 7/2003 | Cosley et al. | 165/80.4 |
| 2003/0219903 A1 | 11/2003 | Wang et al. | |
| 2004/0076562 A1 | 4/2004 | Tonkovich et al. | |
| 2004/0194910 A1* | 10/2004 | Garner et al. | 165/11.1 |

(Continued)

FOREIGN PATENT DOCUMENTS

DE    19963594 A1    7/2001

(Continued)

OTHER PUBLICATIONS

S. Lin, K. Sefiane, J.R.E. Christy. Prospects of confined flow boiling in thermal management of microsystems. Applied Thermal Engineering 22 (2002) 825-837.*

(Continued)

*Primary Examiner* — Jennifer A Leung
(74) *Attorney, Agent, or Firm* — Frank Rosenberg

(57) ABSTRACT

The invention provides methods, apparatus and systems in which there is partial boiling of a liquid in a mini-channel or microchannel. The partial boiling removes heat from an exothermic process.

36 Claims, 24 Drawing Sheets

U.S. PATENT DOCUMENTS

| | | | |
|---|---|---|---|
| 2004/0220434 A1 | 11/2004 | Brophy et al. | |
| 2004/0234566 A1 | 11/2004 | Qiu et al. | |
| 2005/0176832 A1 | 8/2005 | Tonkovich et al. | |
| 2006/0142401 A1* | 6/2006 | Tonkovich et al. | 518/726 |

FOREIGN PATENT DOCUMENTS

| | | |
|---|---|---|
| EP | 0861802 | 9/1998 |
| JP | 57061004 | 4/1982 |
| JP | 2004221434 | 8/2004 |
| WO | WO 99/00186 | 1/1999 |
| WO | WO 02/14854 A1 * | 2/2002 |
| WO | WO03078052 A1 * | 9/2003 |
| WO | WO 03/099429 A1 | 12/2003 |
| WO | WO 2004/037418 A2 | 5/2004 |
| WO | WO 2004/083742 A2 * | 9/2004 |
| WO | WO 2004/099113 A1 | 11/2004 |
| WO | WO 2004/103539 A2 | 12/2004 |
| WO | WO 2004/103539 A3 | 12/2004 |
| WO | WO 2005/082519 A1 | 11/2005 |

OTHER PUBLICATIONS

PCT Search Report mailed Apr 25, 2006.
Kandlikar et al., "Flow Boiling in Microchannels: Non-dimensional Groups and Heat Transfer Mechanisms," Congres de la Societe Francais de Thermique 2003, slides 1-30.
Kandlikar et al., "Extending the Applicability of the Flow Boiling Correlation to Low Reynolds Number Flows in Microchannels," First Int'l Conf. On Microchannels and Minichannels, pp. 1-6 (2003).
Kandlikar, "Fundamental issues related to flow boiling in microchannels and minichannels," Experimental Thermal and Fluid Science, 26, pp. 389-407 (2002).
Kandlikar, Heat Transfer Characteristics in Partial Boiling, Fully Developed Boiling, and Significant Void Flow Regions of Subcooled Flow Boiling, J. Heat Transfer pp. 395-401 (1998).
Liu et al., "Prediction of the Onset of Nucleate Boiling in Microchannel Flow," Heat and Mass Transfer 48. pp. 5134-5149 (2005).
Kandlikar et al., "An Extension of the Flow Boiling Correlation to Transition, Laminar, and Deep Laminar Flows in Microchannels," Heat Transfer Engineering 25(3), pp. 86-93 (2004).
Thome, "Boiling in Microchannels: a review of experiment and theory," Int'l J. Heat and Fluid Flow, 25, pp. 128-139 (2004).
Ohadi et al., "Critical review of available correlations for two-phase flow heat transfer of ammonia," Int. J. Refrig. 19, pp. 272-284 (1996).
Lin et al., "Prospects of confined flow boiling in thermal management of microsystems," Applied Thermal Eng., 22, pp. 825-837 (2002).
Wu et al., "Visualization and measurements of periodic boiling in silicon microchannels," Heat and Mass Transfer, 46, 2603-2614 (2003).
Brutin et al., "Experimental study of unsteady convective boiling in heated microchannels," Heat and Mass Transfer, 46, 2957-2965 (2003).
Prodanovic et al., "On the transition from partial to fully developed subcooled flow boiling," Int'l J. Of Heat and Mass Transfer 45, 4727-4738 (2002).
Zhao et al., "Theoretical studies on transient pool boiling based on microlayer model," Int'l J. Of Heat and Mass Transfer 45, 4325-4331 (2002).
Haynes et al, "Subcooled flow boiling heat transfer in narrow passages," Int'l J. Of Heat and Mass Transfer 45, 3673-3682 (2003).
Lee et al., "Size and shape effects on two-phase flow patterns in microchannel forced convection boiling," J. Micromech. Microeng. 13, 155-164 (2003).
Ramaswamy et al., "High-speed visualization of boiling from an enhanced structure," Int'l J. Of Heat and Mass Transfer 45, 4761-4771 (2002).
Celata et al., "Prediction of the critical heat flux in water subcooled flow boiling using a new mechanistic approach," Int'l J. Of Heat and Mass Transfer 42, 1457-1466 (1999).
Chedester et al., "A proposed mechanism for hydrodynamically-controlled onset of significant void in microtubes," Int'l J. Of Heat and Fluid Flow 23, 769-775 (2002).

Delhaye et al., "Appendix 4: Report of study group o nmicrophysics," I'ntl J. Of Multiphase Flow 29, 1101-1116 (2003).
Dupont et al., "Heat transfer model for evaporation in microchannels. Part II: comparison with the database," Int'l J. Of Heat and Mass Transfer 47, 3387-3401 (2004).
Thome et al., "Heat transfer model for evaporation in microchannels. Part I: presentation of the model," Int'l J. Of Heat and Mass Transfer 47, 3375-3385 (2004).
Mishkinis et al., "Homogeneous nucleation and the heat-pipe boiling limitation," J. Eng. Physics and Thermophysics, 76, 813-818 (2003).
Peng et al., "Boiling nucleation during liquid flow in microchannels," Int. J. Mass Transfer, 41, 101-106 (1998).
Gopinath et al., "Interfacial heat transfer during subcooled flow boiling," Int. J. Heat and Mass Transfer 45, 3947-3959 (2002).
Honda et al., "Enhanced boiling heat transfer from electronic components by use of surface microstructures," Expt'l Thermal and Fluid Science 28, 159-169 (2004).
Pettersen, "Flow vaporization of CO2 in microchannel tubes,"Expt'l Thermal and Fluid Science 28, 111-121 (2004).
Peng et al, "Flow boiling of binary mixtures in microchanneled plates," Int. J. Heat and Mass Transfer 39, 1257-1264 (1996).
Peng et al, "An experimental study of convective heat transfer in silicon microchannels with different surface conditions," Int. J. Heat and Mass Transfer 46, 2547-2556 (2003).
Peng et al, "Cluster dynamics and fictitious boiling in microchannels," Int. J. Heat and Mass Transfer 43, 4259-4265 (2000).
Owhaib et al., "Evaporative heat transfer in vertical circular microchannels," Applied Thermal Engineering 24, 1241-1253 (2004).
Peng et al., "Dyanmic characteristics of microscale boiling," Heat and Mass Transfer 37, 81-86 (2001).
Blackmore et al., "Detachment of Bubbles in Slit Microchannels by Shearing Flow," J. Colliod and Interface Science 241, 514-520 (2001).
Francois et al., "Extension of the compensated distortion method to the critical heat flux modelling in rectangular inclined channel," Int. J. Heat and Mass Transfer 46, 2673-2684 (2003).
Wu et al., "Liquid/two-phase/vapor alternating flow during boiling in microchannels at high heat flux," Int. Comm. Heat Mass Transfer 30, 295-302 (2003).
Kandlikar, "Heat transfer mechanisms during flow boiling in microchannels," Trans ASME 126, 8-16 (2004).
Ramaswamy et al., "High-speed visualization of boiling from an enhanced structure," Int. J. Heat and Mass Transfer, 45, 4761-4771 (2002).
Zhang et al., "Boiling heat transfer from mechanically fabricated porous tubes at atmospheric and superatomospheric pressures," Heat Transfer—Asian Research 28, 640-648 (1999).
Ghiaasiaan et al., "Boiling incipience in microchannels," Int. J. Heat and Mass Transfer, 45, 4599-4606 (2002).
Wu et al., "Boiling instability in parallel silicon microchannels at different heat flux," Int. J. Heat and Mass Transfer, 47, 3631-3641 (2004).
Li et al, "Bubble cavitation in a microchannel," Int. J. Heat and Mass Transfer, 47, 2689-2698 (2004).
Lee et al, "Bubble dynamics in microchannels.Part I single microchannel," Int. J. Heat and Mass Transfer 47, 5575-5589 (2004).
Li et al, "Bubble dynamics in microchannels.Part II two parallel channels," Int. J. Heat and Mass Transfer 47, 5591-5601 (2004).
Peng et al., "Bubble dynamics in microchannels: statistical mechanics approach," Int. J. Heat and Mass Transfer 44, 2957-2964 (2001).
Steinke et al., "Control of dissolved air in water during flow boiling in microchannels," Int. J. Heat and Mass Transfer 47, 1925-1935 (2004).
Peng et al., "Boiling nucleation during liquid flow in microchannels," Int. J. Heat and Mass Transfer 41, 101-106 (1998).
Office Action in JP Application No. 2007-540057, mailed Jan. 4, 2011.

* cited by examiner

Prior Art

View from bottom

PARTIAL BOILING IN MINI AND MICRO-CHANNELS

RELATED APPLICATIONS

This application claims the benefit of priority provisional application Ser. No. 60/624,860 filed Nov. 3, 2004.

This invention relates generally to methods, apparatus and systems (where systems are constituted by apparatus containing a fluid or fluids and may be further characterized by parameters such as pressure, temperature, etc.) in which there is partial boiling of a liquid in a mini-channel or microchannel. A minichannel has at least one dimension of 10 mm or less. A microchannel has at least one dimension of 2 mm or less, in some embodiments 1 mm or less, in some embodiments 0.5 mm or less, and in some embodiments in the range of 0.01 to 2 mm. While a mini and microchannel generally have the dimensions described above, in some preferred embodiments, a microchannel has a diameter of $D_h < 2$ mm, where Dh is the hydraulic diameter, and a mini-channel is defined as having a diameter $D_h$ from 2 to 10 mm.

Theory of Partial Boiling

Boiling is known as a highly efficient heat transfer mechanism that provides high heat flux density based on surface area and volume. There are several different boiling regimes including low vapor quality flow, nucleate boiling, film boiling and transition boiling. Nucleate boiling is mostly found in the industrial applications. Boiling can take place at heat transfer surface both in fluid flow (flow boiling) and fluid pool (pool boiling) or in the volume of the fluid (flash). Through phase change of the fluid, flow boiling has the potential to achieve an isothermal heat sink in the fluid while the phase change is occurring. Flow boiling can achieve very high convective heat transfer coefficients, and that coupled with the isothermal fluid allows the heat transfer wall to remain at quasi-constant temperature along the flow direction. This is a desirable heat transfer situation for many thermal, nuclear and chemical process applications In many chemical processes, such as an exothermic chemical reactor, the reaction rate strongly depends on the local temperature. An optimal temperature throughout the reaction zone often leads to a maximum yield, conversion and desired selectivity. Thus, boiling heat transfer is used in process control or thermal management of various reactions to maintain an isothermal thermal condition where the exothermic reaction(s) releases heat. Compared to a boiling process control, a cooling system via single-phase fluid convection generally cannot achieve a near isothermal boundary condition for the reactions without large flow rates needed to keep the stream at constant temperatures and increase the convective heat flux.

So far, boiling in microchannels has not been used in the thermal management and control of the microchannel chemical reaction processes due to various postulated or practical technical issues including the following:
1. Flow boiling in microchannels is associated with the flow patterns different from that found in the ordinary flow channels where vapor bubbles are smaller than the channel diameters and the channel wall is generally well wetted by the liquid. The hydraulic diameter of microchannels is usually smaller than the characteristic diameter of the vapor bubbles so that due to capillary effect vapor slugs and liquid slugs consecutively flow by a fixed location of the channel (FIG. 2). The prediction methods and design criteria for this flow pattern are not well established.
2. The other desired flow patterns such as bubbly flow and annular flow may only be possible in a very narrow flow parameter range or limited operation conditions or may be absent.
3. Due to the existence of vapor slugs, local hot spot of the wall and in turn the temperature non-uniformity may occur due to the low vapor-wall heat transfer rate.
4. Due to the existence of vapor slugs, severe flow and pressure oscillation may occur in microchannel boiling. Instability of the entire cooling system may instantly occur.
5. The heat transfer crisis can occur even at low heat duty due to the large difference between the heat transfer coefficients by evaporation and by single-phase vapor convection. This is characterized by the critical heat flux (CHF) that may be very low and lead to non-isothermal heat transfer (FIG. 2).
6. The flow distribution and manifolding are difficult in microchannel arrays with two-phase flow, while a large number of integrated microchannels is usually needed for the desired process capacity.

The inventive process makes it possible to make use of flow boiling in microchannels integrated in unit operations to realize a stable isothermal boundary condition for the exothermal reaction. The reaction process can be thus thermally controlled to operate in an optimal condition.

The term "equilibrium quality $X_{eq}$" also known as quality or "X" is defined as:

$$X_{eq} = \frac{z \cdot q'' \cdot P}{A \cdot G \cdot h_{fg}}, \qquad (1)$$

where
z[m]=The distance from the channel inlet in water flow direction (m)
q"[W/m²]=The average channel wall heat flux
P[m]=Channel perimeter normal to the direction of flow
A[m²]=Channel cross sectional area normal to the direction of flow
G [kg/m²/s]=Mass flux rate through the channel cross sectional area normal to flow
$h_{fg}$[J/kg]=Latent heat of evaporation
The equation (1) assumes:
1) The point of Onset of Nucleate Boiling (ONB) with $X_{eq}$=0 is just located at the channel inlet. In the practical operation, the water flow at inlet would be slightly subcooled due to non-condensable gas. As such, the location of $X_{eq}$=0 would not be at z=0, where z represents the direction of flow and z=L (where L is the length of the boiling microchannel) represents the end of the microchannel. On the other hand, the water flow at inlet could also be overheated ($X_{eq}$>0) due to the pre-heating to maintain water temperature before entering the channel;
2) Wall superheat $T_w$-$T_{sat}$ is large enough to start boiling near the inlet of the microchannel, defined as the first 5% of its length;
3) q" is constant along the channel periphery and in flow direction.

The local quality of the convecting flow is needed to estimate the pressure drop in a channel. Knowing the void fraction and vapor quality variation along the channel length, the two-phase pressure drop in the channel can be calculated using the separated flow model of Lockhart and Martinelli

[1949][1]. This equation, shown below, breaks up the pressure drop into frictional losses and acceleration from boiling terms, $$\Delta p = \Delta p_{fr} + \Delta p_{acc} \qquad (2)$$
$$= \int_0^z \frac{2f_{lo}G\phi_{lo}^2}{D_h\rho_l}dz +$$
$$\int_0^z G^2 \frac{dX}{dz}\left\{\left[\frac{2X}{\rho_v\alpha} - \frac{2(1-X)}{\rho_l\alpha}\right] + \frac{d\alpha}{dz}\left[\frac{(1-X)^2}{\rho_l(1-\alpha)^2} - \frac{X^2}{\rho_v\alpha^2}\right]\right\}dz.$$

$D_h$[m]=Hydraulic diameter of the channel
$f_{lo}$[−]=Friction factor of the channel when the entire mass flux rate as liquid
$f_l$[−]=Friction factor of the channel when the mass flux rate as liquid, $G(1-X)$
$\rho_v$[kg/m³]=Density of the vapor phase
$\rho_l$[kg/m³]=Density of the liquid phase The terms in equation (2) that aren't defined above need the Martinelli parameter, X, which defines the pressure gradients for the liquid flowing alone over the pressure gradient of the vapor flowing alone, $$\chi^2 = (dp/dx)_l/(dp/dx)_v \qquad (3)$$

where p is the local static pressure. The correlation for α in equation (2) for turbulent flow in large pipes is given as $$\alpha = [1+0.28\chi^{0.71}]^{-1} \qquad (4)$$

[1] Lockhart, R. W. and Martinelli, R. C., "Proposed Correlation of Data for Isotherrnal Two-Phase, Two-Component Flow in Pipes", Chemical Engineering Progress 45(1), pp. 39-48, 1949.

The value of $\phi_{lo}^2$, the two-phase flow friction multiplier, is dependent upon the friction multiplier for liquid flowing alone $\phi_l^2$, the friction factors and local quality, $$\phi_{lo}^2 = \phi_l^2\left(\frac{f_l}{f_{lo}}\right)(1-x)^2, \qquad (5)$$

The friction multiplier for liquid flowing alone is given by the Martinelli-Nelson correlation as, $$\phi_l^2 = 1 + \frac{C}{\chi} + \frac{1}{\chi^2}. \qquad (6)$$

C in equation (6) has terms dependent upon the gas and liquid phase flow regimes
  20 (liquid-turbulent, gas-turbulent)
  12 (liquid-viscous, gas-turbulent)
  5 for (liquid-viscous, gas-viscous).
Lee (2001) suggested a correlation of the coefficient C:

$$C = 0.06185 \, Re_{lo}^{0.726}, \qquad (7)$$

for micro-channels down to $D_h \sim 0.8$ mm.

The term "critical heat flux", or CHF, is the local heat flux at which wall temperature can not be maintained due to heat transfer mechanism change from boiling to vapor convection. This results in the formation of a localized hot spot. FIG. 1 shows the typical boiling curve, with heat flux on the vertical axis and the temperature difference between the wall ($T_w$) and the saturated fluid ($T_s$). Smaller values of the temperature difference range have single phase heat transfer and low heat fluxes. There is a threshold temperature difference where nucleate boiling starts and increasing the difference slightly can result in larger heat fluxes, as nucleate boiling starts to occur. CHF occurs when the difference reaches a point where the heat transfer rate changes from nucleate/bubbly flow to local dry out and gas phase resistance starts to dominate heat transfer. CHF can occur before dry-out.

CHF results in larger hydraulic diameters are fairly well characterized. CHF for saturated fluids are generally a function of the following effects:
1. Flow rate: CHF goes up when flow rate is increased for a fixed inlet conditions and geometry
2. Pressure: When pressure is increased from ambient pressure the CHF increases to a local maximum and gradually decreases with increasing pressure
3. Channel size: CHF increases when channel size increases;
4. Channel length: Longer channels lead to lower CHF;
5. Vapor quality: Increased vapor quality X leads to smaller CHF;
Channel size and vapor quality are related to average wall heat flux in saturated boiling. Thus, higher process heat flux (average) quickly approaches local CHF via higher vapor generation rate and accumulated vapor amount.

The boiling number, Bo, is the heat flux non-dimensionalized with mass flux and latent heat of vaporization $$Bo = \frac{q''}{G \cdot h_{fg}} \qquad (8)$$

The capillary number, Ca, ratios the viscous forces to surface tension forces $$Ca = \frac{\mu \cdot G}{\rho \cdot \sigma} \qquad (9)$$

where
  μ[kg/m/s]=Viscosity of the liquid
  ρ[kg/M³]=Density of the liquid
  σ[N/m]=Surface tension of the liquid
The Weber number represents the ratio of inertial to surface temperature forces $$We = \frac{D_h \cdot G^2}{\rho \cdot \sigma} \qquad (10)$$

The estimation of critical heat flux for saturated flow boiling has been studied for channels larger than microchannels. One correlation is from Katto and Ohno [Katto, Y. and Ohno, H., Int. J. Heat Mass Transfer, v. 26(8), pp. 1641-1648, 1984]

$$q''_{co1} = c_k G h_{fg} We_k^{-0.043}\left(\frac{L}{D_h}\right)^{-1} \qquad (11)$$

$$q''_{co2} = 0.10 G h_{fg} \gamma^{0.133} We_k^{-1/3}\left[\frac{1}{1+0.0031(L/D_h)}\right]$$

$$q''_{co3} = 0.098 G h_{fg} \gamma^{0.133} We_k^{-0.433}\left[\frac{(L/D_h)^{0.27}}{1+0.0031(L/D_h)}\right]$$

$$\gamma = \frac{\rho_v}{\rho_l}, \, We_k = \frac{G^2 L}{\rho_l \sigma}$$

$$C_k = 0.34, \quad \text{for } \frac{L}{D_h} > 150$$

$$C_k = 0.25 + 0.0009 \left[\frac{L}{D_h} - 50\right], \text{ for } 50 \leq 150 \quad (12)$$

$$C_k = 0.25, \text{ for } \frac{L}{D_h} < 50$$

$We_k$ is the length based Webber number, using the length scale of the channel length.

$$K_{k1} = \frac{1.043}{4C_k We_k^{-0.043}} \quad (13)$$

$$K_{k2} = \frac{5}{6} \cdot \frac{0.0124 + D_h/L}{\gamma^{0.133} \cdot We_k^{-1/3}}$$

for $q''_{co1} < q''_{co2}$: $q''_{co} = q''_{co1}$ for $q''_{co1} > q''_{co2}$:

$q''_{co} = q''_{co2}$ when $q''_{co2} < q''_{co3}$ $q''_{co} = q''_{co3}$ when $q''_{co2} \geq q''_{co3}$ for $K_{k1} > K_{k2}$: $K_k = K_{k1}$ for $K_{k1} \leq K_{k2}$: $K_k = K_{k2}$ $$q''_{crit} = q''_{co}[1 + K_k(h_{l,s} - h_{l,in})/h_{fg}] \quad (14)$$

For saturated flow boiling $q''_{crit}$ equals $q''_{co}$.
SR number is defined as:

$$SR = \frac{Bo \times (T_{wall,max} - T_{sat}) \times D_h}{T_{sat} \times L} \quad (15)$$

Where, Bo=Boiling number, dimensionless
$T_{wall, max}$=Maximum temperature of the wall surrounding boiling section, K
$T_{sat}$=Saturation temperature of fluid at given pressure and composition, K
$D_h$=Hydraulic diameter of channel in which boiling is occurring, mm
L=Length of the channel over which boiling occurs, mm The difference between the wall temperature and the saturation temperature is defined as the overage temperature. For a matrix of aligned microchannels where the local heat flux varies from channel to channel the difficulties described above become more challenging. Potential unit operations that would have a varying heat flux profile over a matrix of connecting channels include but aren't limited to the following: Exothermic chemical reactions, catalytic or homogeneous, distillation tower heat removal, desorption stage in an absorption or adsorption system, exothermic mixing processes, and the like. This can occur when the microchannels are aligned cross-flow to the direction of the other unit operation's channels. For the varying channel flux situation there may be need for more flow in channels with the higher heat fluxes and less flow to channels with less heat fluxes to sustain convective boiling.

PRIOR ART

The published literature does not reflect a consensus on the merits of microchannel boiling.

Boiling Regime and Heat Transfer Mechanisms

On one hand, some investigators have suggested that microchannel boiling is unique and possesses potential benefits over their macroscale counterparts. For example, Kandlikar (2002) performed a critical review flow boiling in channels with hydraulic diameter less than 3 mm. Based on this review, the following findings were made:

Three flow patterns are commonly encountered during flow boiling in minichannels: isolated bubble, confined bubble or plug/slug, and annular.

The effect of interfacial surface tension between phases is crucial in determining the final boiling flow regime. The presence of small nucleating bubbles, as small as 10 to 20 microns has been confirmed.

It should be noted that from a heat transfer performance standpoint, isolated bubbles are most desirable. Chedester and Ghiaasiaan (2002) cite data and previous theoretical analyses supporting the theory that bubble nucleation and evolution phenomena in microchannels are fundamentally different than in their large channel counterparts. In subcooled boiling, the velocity and temperature gradients near the walls of microchannels can be very large, and bubbles resulting from subcooled or saturated boiling can be extremely small. The occurrence of extremely small bubbles significantly impacts the various subcooled boiling processes including the onset of nucleate boiling (ONB), onset of significant void (OSV), and departure from nucleate boiling (e.g., film boiling).

The same authors (Ghiaasiaan and Chedester, 2002) also propose the hypothesis that boiling incipience in microchannels may be controlled by thermocapillary forces that tend to suppress the formation of microbubbles on wall cavities. If this were indeed the case, it would suggest that the heat transfer in microchannels, which is greatly enhanced by nucleate boiling due to the latent heat of vaporization, would actually perform worse than in conventional-sized channels. Their studies suggest that macroscale models and correlations for boiling heat transfer appear to under-predict the heat fluxes required for incipience of boiling in microtubes (defined to possess diameters in the range of 0.1 mm to 1 mm). It should be noted, among other factors, that their experiments were run in the fully turbulent regime, whereas most practical microchannel applications are operated in the laminar flow regime.

Haynes and Fletcher (2003) describe work where subcooled flow boiling heat transfer coefficients for select refrigerants in smooth copper tubes of small diameter have been investigated experimentally. The parameter ranges examined are as follows: tube diameters of 0.92 and 1.95 mm, heat fluxes from 11 to 170 kW/m$^2$, and total mass fluxes of 110 to 1840 kg/(m$^2$-s). Furthermore, the range of liquid Reynolds numbers encompassed by the data set is 450 to 12,000. In their work, they encountered no evidence that convection suppresses the nucleate term nor that nucleation events enhance the convective term, even in laminar and transitional flows. However, the laminar flows, in particular, are prone to enhancement by unknown mechanism.

Prodanovic, et al. (2002) note in their experimental studies that bubble agitation is the primary heat transfer model during nucleate boiling. Agitation dissipates as the bubble travels away from the heated channel surface.

Lee et al. (2004) conducted experiments in bubble dynamics in a single trapezoid microchannel with a hydraulic diameter of 41.3 microns. The results of the study indicates that the bubble nucleation in the microchannel typically grows with a constant rate from 0.13 to 7.08 microns/ms. Some cases demonstrate an extraordinarily high growth rate from 72.8 to 95.2 microns/ms. The size of bubble departure from the microchannel wall is found to be governed by surface tension and drag of bulk flow (as opposed to wall shear stress) and may be fairly correlated by a modified form of Levy equation. They also maintain that the bubble frequency in the microchannel is comparable to that in an ordinary sized channel.

Thome (2004) reviews recent research in microchannel boiling. Experiments and theory on evaporation in microchannels have been reviewed. He maintains that the most dominant flow regime appears to be the elongated bubble mode that can persist up to vapor qualities as high as 60-70% in microchannels, followed by annular flow, and that the controlling heat transfer mechanism is not nucleate boiling nor turbulent convection but is transient thin film evaporation. Flow boiling heat transfer coefficients have been shown by some investigators to be dependent nearly exclusively on heat flux and saturation pressure, i.e. similar to nucleate pool boiling heat transfer and only slightly dependent on mass velocity and vapor quality. However, more recent tests demonstrate a mass velocity and vapor quality effect, supporting the hypothesis that boiling heat transfer is controlled by slug flow or thin film boiling.

Stability of Flow

Stability of boiling flow in a microchannel is an issue of great concern. Since no comprehensive theory for onset of instability yet exists, it is primarily studied through flow pressure fluctuations and visualization. Heat transfer is much less efficient for unstable flow because of many factors including unsteadiness in the flow patterns, formation of film boiling, reverse flow, and poor flow distribution. Below are citations of the existing prior art literature on this subject.

Brutin et al. (2003) investigated two-phase flow instabilities in convective boiling taking place in narrow rectangular microchannels. Hydraulic diameter was 889 microns and channel length was 200 mm. The experiments were conducted at mass fluxes of 240 kg/(m$^2$–s) and heat fluxes ranging from 3.3 to 9.6 W/m$^2$. All these conditions exhibited vapor slug formation which blocks the two-phase flow and pushes the two-phase flow back to the flow entrance. Based on their experimental observations, they establish a criterion for steady state flow as low fluctuation amplitude variations in measured flow pressure of less than 1 kPa and a characteristic oscillation frequency of a ratio less than 20 (peak amplitude to noise amplitude).

Wu et al. (2004) describe a series of experiments carried out to study different boiling instability modes of water flowing in microchannels at various heat flux and mass flux values. Eight parallel silicon microchannels, with an identical trapezoidal cross-section having a hydraulic diameter of 186 micron and a length of 30 mm, were used in the experiments. When the wall heat flux was increased from 13.5 to 22.6 W/cm$^2$ and the time average mass flux of water was decreased from 14.6 to 11.2 g/cm$^2$-s, three kinds of unstable boiling modes were observed in the microchannels:

Liquid/two-phase alternating flow (LTAF) at low heat flux and high mass flux

Continuous two-phase flow (CTF) at medium heat flux and medium mass flux, and

Liquid/two-phase/vapor alternating flow (LTVAF) at high heat flux and low mass flux.

Generally, LTAF occurred at lower heat flux (from 13.5 to 16.6 W/cm2) with higher average mass flux (from 14.6 to 12.7 g/m$^2$-s); CTF occurred at the medium heat flux (18.8 W/cm$^2$) and medium mass flux (11.9 g/cm$^2$-s), and LTVAF occurred at higher heat flux (22.6 W/cm$^2$) and lower mass flux (11.2 g/cm$^2$-s). Among the three unstable boiling modes, oscillation amplitudes in LTVAF were the largest with oscillations of pressures and mass flux nearly out of phase.

$L/D_H$ Values

All microchannel experiments are conducted with a certain fixed geometry. For the purposes of summarizing heat transfer performance for these devices, the length-to-diameter ratio, typically the channel length divided by the hydraulic diameter, $L/D_H$, has been found to be a very useful metric. Much of the prior art in the literature does not explicitly report the length of the channels used in their experiments. Those that do are listed below.

Brutin et al. (2003): $L/D_H$=100 and 250 (see description above under "Stability of Flow").

Wu et al. (2004): $L/D_H$=161 (see description above under "Stability of Flow").

Lee et al. (2003): An integrated microchannel heat sink consisting of shallow, nearly rectangular microchannels was used to study the effects of the micrometer-sized channel shape on the evolving flow patterns and thermal performance of the microsystem. The device used channels with a equivalent diameter $D_H$=24 microns and a total length of 19 mm giving $L/D_H$=792. Local nucleation and isolated bubble formation was found to be negligible. The dominant flow pattern is an unsteady transition region connecting an upstream vapor zone to a downstream liquid zone with an average location depending on the input power.

Warrier et al. (2002): Both single-phase forced convection and subcooled and saturated nucleate boiling experiments were performed in small rectangular channels using FC-84 as test fluid. Test sections consisted of five parallel channels with each channel having the following dimensions: hydraulic diameter $D_H$=0.75 mm and length to diameter ratio=409.8. The experiments were performed with the channels oriented horizontally and uniform heat fluxes applied at the top and bottom surfaces. The parameters that were varied during the experiments included the mass flow rate, inlet liquid subcooling, and heat flux. New heat transfer correlations were generated for subcooled and saturated flow boiling heat transfer.

Pettersen (2004): Liquid CO2 evaporation in microtubes of diameter 0.8 mm and length 0.5 m ($L/D_H$=625). Heat transfer and pressure drop measurements were conducted at varying vapour fraction for temperatures in the range of 0 to 25° C., mass flux 190-570 kg/(m$^2$-s), and heat flux 5-20 kW/m$^2$. Heat transfer results show significant influence of dryout, particularly at high mass flux and high temperature. The flow observations reflect increasing entrainment at higher mass flux, and a dominance of annular flow (slug flow and thin film boiling).

Engineered Features to Enhance Boiling

Finally, boiling heat transfer characteristics of a microchannel can also be enhanced by applying a porous coating or in some means engineer porous or grooved structures on the wall surfaces of a microchannel. Ammerman and You (2001), for instance, described experimental work using porous coatings on a channel of width 2 mm and total length of 8 cm. The heat transfer characteristics for convective boiling using the coated channel and an uncoated channel with the same dimensions and flow mass fluxes were compared. The coated microchannel exhibited increase in heat transfer coefficient as well as a higher allowable critical heat flux.

Honda and Wei (2004) report work to enhance boiling heat transfer from electronic components immersed in dielectric liquids by use of surface microstructures. The microstructures developed include surface roughnesses produced by sandblast, sputtering of $SiO_2$ layer followed by wet etching of the surface, chemical vapor deposition of $SiO_2$ layer etc., a brush-like structure (dendritic heat sink), laser-drilled cavities, reentrant cavities, microfins, alumina particle spraying, painting of silver flakes or diamond particles, and heat sink studs with drilled holes, microfins and microchannels, pin fins etc. The primary focus of the study included the mitigation of incipience temperature overshoot, enhancement of nucleate boiling heat transfer, and increasing the critical heat flux. Their findings are as follows:

Complex microroughness, microreentrant cavity and microporous structure are effective in decreasing boiling incipience superheat. However, the microreentrant cavity tended to fill with liquid when the channel surface is subcooled. The mechanism of reduced boiling incipience superheat by the surface microstructure is not well understood.

Surface roughness is effective in enhancing nucleate boiling. However, the authors could not directly relate the surface roughness parameter $E/D_H$ to heat transfer enhancement. They found that surface roughness produced by the deposition of thin $SiO_2$ film (such as in microchip applications) is effective in increasing the critical heat flux.

Surface cavities are effective in enhancing nucleate boiling and increasing critical heat flux. In the range of surface cavity mouth diameter deq=1.6-9 microns, the cavity with larger deq was observed to be more effective in generating bubble nucleation sites.

Microporous structures are most effective in enhancing nucleate boiling. However, the slope of boiling curve of the microporous surface decreases sharply in the high-heat-flux region and the wall superheat at the CHF point is higher than the maximum allowable temperature for certain microchip applications.

the authors discovered that micropin-fins are most effective in increasing the critical heat flux, $q_{CHF}$. The boiling curve of micropin-finned surface shows a sharp increase in q with increasing $\Delta T_{sat}$ ($\Delta T_{sat}$=wall superheat=$T_{wall}-T_{sat}$). The $q_{CHF}$ increases monotonically with increasing $\Delta_{sub}$ ($\Delta T_{sub}$=liquid subcooling=$T_{sat}-T_{boil}$). The optimum fin spacing that gives the highest $q_{CHF}$ decreases as $\Delta T_{sub}$ increases.

The surface microstructures act to hold growing bubbles on the surface for a longer time than the smooth surface. This is considered to be an important factor for enhanced heat transfer obtained by the surface microstructures.

The highest performance is obtained with horizontal upward orientation of the chip. The authors give a mathematical expression relating $q_{CHF}$ to inclination angle.

The authors give quantitative measures of increase in $q_{CHF}$ due to channel wall surface roughness in microchip applications as 32.5% and 48%. These results were obtained for average values of surface roughness ∈ of 1.1, 18.7 and 309.3 nm, respectively, as compared to a 1.1 nm surface roughness base case. Furthermore, they generated boiling curves for various values of equivalent porous cavity mouth diameter and porous and engineer pin-fin designs. The enhancement in heat flux at a given wall superheat temperature can be compared to the smoothest surface, Chip S (∈=1.1 nm), and predictions for convective boiling which assumes a perfectly smooth surface (∈=0).

Ramaswamy et al. (2002) describe a study of surface-enhanced boiling in a microchannel using wafer dicing and wet etching was used to fabricate a net of interconnected microchannels on a 10 mm×10 mm piece of silicon wafer. The resultant structure has pores that communicate the interior of microchannels to the liquid pool. The pore diameter was varied in a range 0.12-0.20 mm and the pore pitch in 0.7-1.4 mm. The data were collected maintaining the system pressure at one atmosphere and increasing the wall superheat up to 12 K. A summary of their findings is as follows:

For low to intermediate wall superheat values (4-12° C.), the boiling took place in the isolated bubble regime. With an increase in the wall superheat, coalescence begins to occur, leading eventually to formation of large bubbles. The coalescence phenomenon was controlled to some extent by the pore pitch.

The average bubble departure diameter increased with an increase in the pore size (for same wall superheat). They report that the effect of pore pitch was very small. For a certain pore size, the bubble departure/detachment diameter increased with an increase in the wall superheat.

The frequency of bubble generation increased marginally with an increase in the wall superheat. At intermediate wall superheats (approximately 12° C.), the frequency showed a decreasing trend. Furthermore, the frequency reduced with an increase in the pore pitch and pore diameter.

The authors report that nucleation site density increased with an increase in the wall superheat (for all structures). A larger pitch resulted in fewer bubbles because of fewer pores. The pore size had negligible effect except for one structure where the number of bubbles increased. They maintain that the nucleation site density is a function of the volume evaporated inside the tunnels and the average departure diameter of the bubbles, and that with a change in the pore size, interplay of these two parameters leads to variability in the nucleation site density.

Wall Superheat

Small hydraulic diameter leads to low Reynolds numbers in the laminar regime, typically in the range 100-1000. In such low Reynolds number flows, nucleate boiling is generally required if good heat transfer characteristics in a two-phase microchannel application is to be achieved. However, the high degree of wall superheat oftentimes required to initiate nucleation in microchannels leads to "overshoot" or overly rapid evaporation which in turn can lead to bubble coalescence, slug flow, and various regimes of flow instability. One means of controlling boiling overshoot is to maintain the wall superheat temperature $\Delta T_{sat}=T_{wall}-T_{sat}$ (sometimes denoted as $\Delta T_{sup}$) to as low a value as possible for nucleate boiling.

Kandlikar (2004) discussed flow boiling in a channel from the subcooled liquid entry at the inlet to a liquid-vapor mixture flow at the channel outlet. As the liquid flows through a microchannel, nucleation occurs over cavities that fall within a certain size range under a given set of flow conditions. Assuming that cavities of all sizes are present on the channel wall surface, he proposes that the wall superheat necessary for nucleation may be expressed based the equations developed by Hsu and Graham (1961) and Sato and Matsumura (1964) and the assumption that subcooled temperature difference is set identically to zero:

$$\Delta T_{sat,ONB} = \frac{8\sigma T_{sat} v_{fg} C}{D_h h_{fg}} \quad (16)$$

For channels larger than 1 mm, the above expression predicts that the wall superheat is quite small, but as the channel size becomes smaller, larger superheat values are required to initiate nucleation. For example, water in a 200-micron channel requires a wall superheat of 2° C. before nucleation can begin.

In the case of channels with hydraulic diameter less than 50 microns, the wall superheat requirement may exceed 10° C.

with water, and above 2-3° C. for refrigerants. Flow boiling in channels smaller than 10 microns will pose significant challenges to achieve nucleate boiling.

When the wall superheat exceeds the temperature required to nucleate cavities present on the channel walls, nucleate boiling is initiated in a microchannel. Absence of nucleation sites of appropriate sizes may delay nucleation. Other factors such as sharp corners, fluid oscillations, and dissolved gases affect the nucleation behavior. The necessary wall superheat is estimated to be 2-10° C. for channels smaller than 50-100 micron hydraulic diameter with R-134a and water, respectively, at atmospheric pressure conditions.

One important factor to consider for all the wall superheat estimates using the above equation is that this expression is based on conventional channel boiling heat transfer correlations. The references for this expression predate all the literature on studies of boiling phenomena in microchannels by many years and therefore may not be applicable to microchannel wall superheat predictions.

Peng et al. (1997) report results that give larger values for wall superheat temperature at the same hydraulic diameter, such as illustrated in FIG. 3. They maintain that nucleate boiling in microchannels is much more difficult to achieve than in conventional size channels although they also hypothesize that the fluid is in a highly non-equilibrium state with an exceptional capacity to absorb and transport thermal energy.

Ramaswamy et al. (2002) report experimental results for average heat flux versus wall superheat in microchannels with engineered features in the walls to enhance boiling which range from about 4 W/cm$^2$ at a wall superheat of 4.5° C. to about 19 W/cm$^2$ at a wall superheat of 13° C. with hydraulic diameter varying between 0.134 mm and 0.287 mm. Finally, Honda and Wei (2004) have measured average heat flux for a given wall superheat for engineered wall surfaces. FIG. 4 shows the combined effects of fin thickness and fin height on the boiling curve of micropin-finned chip. The boiling curves of various other chip designs (Chip S, Oktay and Schmekenbecher, O'Connor et al., and Anderson and Mudawar) are also shown for comparison. In FIG. 4, Chip PFa-h (a=30 and 50, h=60-270) denotes the micropin-finned chip with in-line array of a micron thick and h micron high square pin fins. The fin spacing is the same as the fin thickness.

REFERENCES

Ammermann, C. N. and S. M. You, 2001, "Enhancing Small-Channel Convective Boiling Performance Using a Microporous Surface Coating," *Journal of Heat Transfer* 123(5), 976-983.

Brutin, D., F. Topin, and L. Tadrist, 2003, "Experimental study of unsteady convective boiling in heated minichannels," *International Journal of Heat and Mass Transfer* 46, 2957-2965.

Chedester, R. C. and S. M. Ghiaasiaan, 2002, "A proposed mechanism for hydrodynamically-controlled onset of significant void in microtubes," *International Journal of Heat and Fluid Flow* 23, 769-775.

Ghiaasiaan, S. M. and R. C. Chedester, (2002), "Boiling incipience in microchannels," *International Journal of Heat and Mass Transfer* 45, 4599-4606.

Honda, H and J. J. Wei, 2004, "Enhanced boiling heat transfer from electronic components by use of surface microstructures," *Experimental Thermal and Fluid Science* 28, 159-169.

Hsu, Y. Y., and Graham, R. W., 1961, "An Analytical and Experimental Study of the Thermal Boundary Layer and Ebullition Cycle in Nucleate Boiling," NASA TN-D-594.

Kandlikar, S. G., 2002, "Fundamental issues related to flow boiling in minichannels and microchannels," *Experimental Thermal and Fluid Science* 26 (2002) 389-407.

Kandlikar, S. G., 2004, "Heat Transfer Mechanisms During Flow Boiling in Microchannels," Transactions of the ASME, Vol 126, February 2004.

Lockhart, R. W. and Martinelli, R. C., "Proposed Correlation of Data for Isothermal Two-Phase, Two-Component Flow in Pipes", Chemical Engineering Progress 45(1), pp. 39-48, 1949.

Lee, M., Y. Y. Wong, M. Wong, and Y. Zohar, 2003, "Size and shape effects on two-phase flow patterns in microchannel forced convection boiling," Journal OF Micromechanics and Microengineering 13, 155-164.

Lee, P. C., F. G. Tseng, and Chin Pan, 2004, "Bubble dynamics in microchannels. Part I: single microchannel," *International Journal of Heat and Mass Transfer* 47, 5575-5589

Peng, X. F., H. Y. Hu, and B. X. Wang, 1998, "Boiling Nucleation during liquid flow in microchannels," International Journal of Heat and Mass Transfer 41 (1), 101-106.

Pettersen, J., 2004, "Flow vaporization of CO2 in microchannel tubes," *Experimental Thermal and Fluid Science* 28, 111-121.

Ramaswamy, C., Y. Joshi, W. Nakayama, and W. B. Johnson, 2002, "High-speed visualization of boiling from an enhanced structure," *International Journal of Heat and Mass Transfer* 45, 4761-4771.

Sato, T., and Matsumura, H., 1964, "On the Conditions of Incipient Subcooled Boiling with Forced Convection," Bull. JSME, 7(26), pp. 392-398.

Thome, J. R., 2004, "Boiling in microchannels: a review of experiment and theory," International *Journal of Heat and Fluid Flow* 25, 128-139.

Warrier, G. R., V. K. Dhir, and L. A. Momoda, 2002, "Heat transfer and pressure drop in narrow rectangular channels," *Experimental Thermal and Fluid Science* 26, 53-64.

Wu, H. Y. and P. Cheng, 2003, "An experimental study of convective heat transfer in silicon microchannels with different surface conditions," *International Journal of Heat and Mass Transfer* 46, 2547-2556.

Wu, H. Y. and P. Cheng, 2004, "Boiling instability in parallel silicon microchannels at different heat flux," *International Journal of Heat and Mass Transfer* 47, 3631-3641.

High flux boiling in low flow rate, low pressure drop mini-channel and micro-channel heat sinks", Bowers et al., International Journal of Heat and Mass Transfer; January 1994; v. 37, No. 2, p. 321-332. (12 pages)

"Forced convection boiling in a microchannel heat sink", Jiang et al., Journal of Microelectromechanical Systems; March 2001; v. 10, No. 1, p. 80-87. (8 pages)

"Forced convection and flow boiling heat transfer for liquid flowing through microchannels", Peng et al., International Journal of Heat and Mass Transfer; September 1993; v. 36, No. 14, pp. 3421-2427. (7 pages)

Anderson et al.; Microelectronic Cooling by Enhanced Pool Boiling of a Dielectric Fluorocarbon Liquid; 1988

Fujii et al.; Nucleate Pool Boiling Heat Transfer from MicroPorous Heating Surface; 1983.

Park et al.; Effects of Size of Simulated Microelectronic Chips on Boiling & Critical Heat Flux; 1986.

U.S. Patent Application Publication No.: U.S. 2004/0182551 A1, Boiling Temperature design in Pumped Microchannel Cooling Loops, Sep. 23, 2004.

U.S. Patent Application Publication No.: U.S. 2004/0104012 A1, Boiling Vapor Escape Microchannel Heat Exchanger, Jun. 3, 2004.

U.S. Patent Application Publication No.: U.S. 2004/0082804 A1, Boiling Multiphasic Microchannel Reactions, Apr. 29, 2004.

DISCUSSION OF THE INVENTION

The use of partial liquid boiling in microchannels or minichannels is a useful tool to control other unit operations. Microchannels are preferred and provide superior results over minichannels and even greater superiority over conventionally sized channels. The partial boiling microchannels or minichannels may be adjacent to one unit operation process channel. Alternatively, one boiling mini- or micro-channel may serve two, three, four, or more process channels. The process channel may be a microchannel ($D_h$<2 mm, where Dh is the hydraulic diameter) or a mini-channel ($D_h$ from 2 to 10 mm). The heat flux for a phase change such as boiling is much higher than that for a single phase heat transfer fluid. As such, the rate of heat generation can be much higher in the process channels and thus the overall productivity of the integrated system is held high.

Coolant channels of the present invention are substantially longer than channels of comparative size that have been considered for partial boiling applications in the prior art. Conventionally, longer channels would have been considered inappropriate for partial boiling applications because they would be considered a technical risk due to high pressure drops and problems with dry out. Surprisingly, we have obtained excellent results by the use of partial boiling in long microchannels—including high capacity, high flow, acceptable pressure drop, and stability without a tendency to dry out. Additionally, devices in which the ratio of manifold volume to process channel volume is small, better utilize apparatus volume.

In one aspect, the invention provides a process of removing heat from an exothermic process, comprising: conducting an exothermic process in a process channel; removing heat from the exothermic process in the process channel to an adjacent minichannel or adjacent microchannel; and passing a coolant fluid through the adjacent minichannel or adjacent microchannel that undergoes partial boiling for a length of at least 15 cm as it passes through the adjacent minichannel or adjacent microchannel. In this aspect, the adjacent minichannel or adjacent microchannel comprises an interior wall surface that is a surface on a channel wall that separates the adjacent minichannel or adjacent microchannel from the process channel; and the average shear stress of the fluid at the wall in the adjacent minichannel or adjacent microchannel for a length of at least 1 cm, either measured or calculated, is at least 1 Pascals (Pa).

In another aspect, the invention provides a process of cooling an exothermic process, comprising: conducting an exothermic process in a process channel; providing cooling to the exothermic process in the process channel by transferring heat to an adjacent microchannel having a channel length of at least 15 cm; passing a coolant fluid at a flow velocity of at least 0.1 m/s through the adjacent microchannel that undergoes partial boiling as it passes through the adjacent microchannel; wherein the adjacent microchannel comprises an interior wall surface that is a surface on a channel wall that separates the adjacent microchannel from the process channel; and wherein the surface's temperature during the process is no more than 5° C. above the coolant fluid's boiling temperature at conditions present within the microchannel.

In various embodiments, the invention may have one or more of the following characteristics: a wall stress at least 1 Pa, 10 Pa, 50 Pa., or at least 100 Pa; partial boiling length over at least 15 cm, over entire length of adjacent cooling channel; laminar flow; the process channel mini or micro; bubble diameters in partially boiling fluid are smaller than the gap of the adjacent minichannel or adjacent microchannel (preferably the bubbles diameters do not exceed 90%, more preferably 75%, 50%, 20% of the channel height); hydraulic diameter of 5 mm in the adjacent channel; the temperature in the adjacent minichannel or adjacent microchannel varies by no more than 5° C., 3° C., 1° C., as measured by thermocouples disposed at regions in the channel where partial boiling is occurring; coolant entering the adjacent channel is a single phase fluid; the coolant at least 1° C., more pref at least 3° C., 5° C., 10° C. less than the boiling temp at the conditions in the channel; length of partial boiling at least 25 cm, 50 cm, 100 cm; adjacent minichannel or adjacent microchannel is a microchannel; the surface is 1.5° C. or less above the boiling temperature at the point at which boiling is initiated, and the adjacent microchannel has a hydraulic diameter of 50 to 700 µm; adjacent microchannel is a smooth microchannel having a gap of 1 mm or less and wherein the average heat flux is at least 2, preferably 5, more preferably at least 10 W/cm² of surface; flow rate is at least 5 mL/min per coolant microchannel, channel length is at least 25 cm, and wall surface temperature is 5° C. or less above the boiling temp at channel conditions; pressure oscillation in the microchannel is 5% or less of the baseline pressure, as measured by a pressure gauge; adding a surfactant to the coolant fluid; pressure drop in the microchannel is less than 0.3 psig/2.5 cm for a flux of at least 2 W/cm²; coolant microchannels are at least 30 cm (pref at least 45 cm, 60 cm) with stable partial boiling such that pressure drop fluctuations are no more than 5%, 3% or 1%, as measured by a pressure gauge at the channel outlet; FT reaction with partial boiling cooling and methane selectivity <15%, <12%, <10%, <8%, <5% accomplished by controlling temp well so that selectivity is low; horizontal flow of a partial boiling fluid in a microchannel, which is conventionally considered more challenging than vertical flow; horizontal cooling channels stacked vertically, cross flow partial boiling, or counter, or co-, or diagonal flow; flow segregation in sub-manifolds prior to entering microchannels; no change in heat transfer performance in partial boiling channels if coolant flow is stopped for more than 20 hours during operation; no change in heat transfer performance in partial boiling channels if main process flow in the exothermic channel is stopped for more than 2 hours during operation; any exothermic reaction, including the Fischer-Tropsch reactions, with change in boiling side temperature <3° C., <1° C. from inlet to outlet of heat transfer channel; heat transfer coefficient in first single phase heat transfer section of the cooling microchannel is <80%, <50%, <25%, or <10% of the heat transfer coefficent in the second section of the cooling microchannel where partial boiling is occurring; partial boiling microchannels coupled with an exothermic unit operation where the heat flux or load in the first part of the process channel is substantially different than the heat flux or load in the second part of the process channel; and/or partial boiling at elevated pressures, >100 psig, >300 psig, >500 psig.

Apparatus features of this invention include: Aspect ratio of the coolant channel has a width to height ratio of at least 5, more preferably at least 10, more preferably at least 20. The height is perpendicular to net flow and width is perpendicular to height and length (length is direction of net flow through a channel). Plural (preferably a planar array) process channels and coolant channels (also preferably arranged in planar array; preferably interleaved planar arrays of process and cooling channels) are cross-flow relative to process channels. Coolant channels have horizontal flow (at least 50% of the flow length is oriented horizontally). Varying cross-section of cooling channel with a relatively large gap (at least 10% greater cross-sectional area) at the front of cooling channel where fluid is not boiling, relatively smaller cross-section in partial boiling region; and, optionally, a relatively large cross-sectional area near end of cooling channel. Flow distribution to multiple parallel channels as is discussed herein. Use of barriers that form an orifice diameter that is greater than 10% of a connecting channel hydraulic diameter, in other preferred embodiments >20%, >40%, >50% (orifice may be at entrance area or constricted opening; one-to-one barrier to channel), preferred lengths of orifice; preferably at least 50 micrometers, not more than 90% of channel. Fouling in headers or footers of a microchannel partial boiling channel if TDS>1 ppm (caused by a low flow rate in headers, while channels see a high velocity). Flow distributed to at least 4 or more zones across the inlet face of the array of parallel microchannels for a first distribution, prior to a second distribution into an array of at least 4 more parallel microchannels (see, for example, the low-P vaporizer example).

Partial boiling is defined as a process to vaporize a liquid to achieve a liquid-vapor mixture.

Exothermic reactions include: Fischer-Tropsch reaction; alkylation; oxidation to an oxygenate or nitrile; dimerization; polymerization; hydrogenation, hydrodesulfurization, hydrotreating, or hydrocracking; direct combination of hydrogen and oxygen to hydrogen peroxide.

Exothermic processes comprise unit operations which release energy, including separations such as absorption or adsorption, phase transformations, and exothermic chemical reactions.

In various aspects, the invention includes an exothermic process that transfers heat to a channel (of 10 mm or less) that comprises a boiling fluid, and may include any of the following concepts or any combination of these concepts:

A process comprising partial boiling in a microchannel with a chemical reaction in an adjacent reaction chamber;

A process comprising partial boiling in a microchannel with a chemical reaction in an adjacent reaction microchannel;

A process comprising partial boiling in a microchannel with a chemical reaction in an adjacent reaction chamber, whereby the catalyst temperature rises less than 30° C. (more preferably less than 10° C., less than 5° C., less than 3° C.) along the length of the reaction chamber and the reaction contact time is less than 300 ms;

A process comprising partial boiling in a microchannel with a process comprising a phase change in an adjacent process chamber;

A process comprising partial boiling in a microchannel with a process comprising a phase change in an adjacent process microchannel;

A process comprising partial boiling in a microchannel with a process comprising a distillation of a fluid mixture comprising at least two fluid components in an adjacent process microchannel;

A process comprising partial boiling in a microchannel with a process comprising a phase change in an adjacent process chamber, whereby the temperature rise is less than 10° C. in the process chamber;

A process comprising partial boiling in a microchannel with a mixing process in an adjacent process chamber;

A process comprising partial boiling in a microchannel with a mixing process in an adjacent process microchannel;

A process comprising partial boiling in a microchannel with a mixing process in an adjacent process chamber, whereby the temperature rise in the mixing chamber is less than 5° C.;

A process comprising partial boiling in a microchannel with a fermentation process in an adjacent process chamber;

A process comprising partial boiling in a microchannel with a fermentation process in an adjacent process microchannel;

A process comprising partial boiling in a microchannel with a fermentation process in an adjacent process chamber, whereby the temperature rise in the mixing chamber is less than 10° C.;

A process comprising partial boiling in a microchannel with a absorption process in an adjacent process chamber, whereby the temperature rise in the absorption chamber is less than 10° C.;

wherein there is a temperature range of 5° C. or less over at least 80% of the cycle time for thermal swing adsorption;

wherein there is a temperature range of 5° C. or less over at least 80% of the time for desorption.

Partial boiling process in a microchannel with >10 channels and a flow distribution quality factor <20%; more preferably less than 10%; and still more preferably less than 5%.

A process comprising partial boiling in a microchannel with an adsorption process in an adjacent chamber; and/or A process comprising partial boiling in a microchannel with an adsorption process in an adjacent microchannel.

In various aspects, the invention includes an exothermic process that transfers heat to a microchannel that comprises a boiling fluid that has dissolved solids (for example, tap water), and may include any of the following concepts or any combination of these concepts: Partial boiling process in a microchannel with more than 3 cycles where heat exchanger efficiency varies by less than 2% as compared before and after cycle in the range 0.01 ppm>TDS boiling fluid<15 ppm; Partial boiling process in a microchannel with 0.01 ppm>TDS boiling fluid<5 ppm for at least 1000 hours with 5% or less (preferably 2% or less) change in outlet temperature on adjacent process microchannel; Partial boiling process in a microchannel with 0.01 ppm>TDS boiling fluid<1 ppm for at least 1000 hours with 5% or less (preferably 2% or less) change in outlet temperature on adjacent process microchannel; Partial boiling process in a microchannel with 0.01 ppm>TDS boiling fluid<15 ppm for at least 100 hours with 5% or less (preferably 2% or less) change in outlet temperature on adjacent process microchannel; Partial boiling process in a microchannel with P>100 psig for at least 1000 hours with 5% or less (preferably 2% or less) change in outlet temperature on adjacent process microchannel; and/or Partial boiling process in a microchannel with <50% boiling for at least 1000 hours with 5% or less (preferably 2% or less) change in outlet temperature on adjacent process microchannel;

In any of the aspects in the paragraph above, the boiling fluid comprises at least 0.01 total dissolved solids (TDS), unless otherwise specified.

In another aspect, the invention provides a process for partial boiling in a microchannel where the SR number is less than about 0.001 for a microchannel length of of 4.0 inches or more.

The invention can further be characterized as a partial boiling process to maintain the temperature variation in an adjacent process channel where exothermic reactions take place at less than 5% above the process inlet stream temperature (K, absolute temperature scale). Or where there is a reduction of temperature rise in the process side of more than 50% with comparison to single phase convection heat transfer (K, absolute temperature scale).

The invention also includes the use of a microchannel to conduct stable, partial boiling heat transfer (per the definition given in Example 3) in a channel that has a channel length to hydraulic diameter ratio equal to or exceeding 1000 and a length of 15 cm or greater.

The invention also provides a method of partial boiling in a microchannel where the overage temperature ($T_w-T_s$) equal to or less than the following function $$56353 \times Bo + 1.4315$$

from Bo=1.0E-06 to 1E-04, for 3 or more channels when each channel's length is L is greater than 15 cm.

The invention further provides a system with where the overage temperature ($T_w-T_s$) equal to or less than the following function $$56353 \times Bo + 1.4315$$

from Bo=1.0E-06 to 1E-04, for 3 or more channels, and where the average maximum flux to minimum heat flux ratio of 3:1 or greater and the each channel's length is at least 15 cm (preferably greater than 20 cm). Alternatively, the Overage temperature can be defined as equal to 4.84E9*SR number+ 2.15 C+/−2 C for boiling in a microchannel.

The invention also provides apparatus for controlling partial boiling in mini or microchannels. In a preferred embodiment the apparatus comprises a pressure controller and/or a stabilizer located down stream of a channel or array of channels.

The invention also provides a method (or system) for controlling temperature in an array of channels in a device having an array of process channels adjacent to an array of partial boiling channels, comprising passing a fluid into a manifold and from the manifold into an array of heat exchange channels that are adjacent to an array of process channels that comprise an exothermic process. The flow of heat exchange fluid is controlled so that flow into the heat exchange channels varies to correspond to a varying heat output by the channels in the array of process channels. The flow into the heat exchange channels is controlled to provide stable partial boiling in the array of heat exchange channels that receive a varying amount of heat. In a preferred embodiment the array of heat exchange channels are cross-flow with respect to the array of process channels. One example of this system is illustrated in example 12.

Shear stress in the direction of velocity, u, may be calculated by the formula $F_x=mu*du/dy$, where mu is viscosity, and du/dy is the velocity gradient for the liquid flow normal to the microchannel wall. However, as in a location of liquid (represented by a control element) the velocity generally has three components, and shear stress also has three components. For a channel flow near and at the surface, a one dimensional assumption can be made and $F_x$ can approximate the net shear at an element surface of the liquid. The use of computational fluid dynamics, including commercial software packages such as Fluent or FEMLAB, may be used to solve the required transport equations such that the surface shear force may be calculated. The surface shear stress may be calculated along the channel length, parallel to the direction of flow. Shear stress at the wall may also be calculated between parallel channels, where flow distribution effects are included to determine the mass flux into each parallel channel as a function of the detailed channel and manifold geometry. Additional calculation methods can be found, for example, in "Fundamentals of Fluid Mechanics," 3$^{rd}$ Ed., B. R. Munson, D. F. Young and T. H. Okiishi, John Wiley & Son, Inc., Weinheim, 1998.

In one embodiment, the shear force or stress deviation factor (SFDF) for a process employing a single process microchannel may be within about 50% of the SFDF for a scaled-up process involving multiple process microchannels. SFDF may be calculated using the formula $$SFDF=(F_{max}-F_{min})/(2F_{mean})$$

wherein: $F_{max}$ is the maximum shear stress in a process microchannel for a specific fluid; $F_{min}$ is the minimum shear stress in the process microchannel for the fluid; and $F_{mean}$ is the arithmetic average shear stress for the fluid at the microchannel wall surface. Within a single process microchannel, operated in accordance with the inventive process, the SFDF may be less than about 2, and in one embodiment less than about 1, and in one embodiment less than about 0.5, and in one embodiment less than about 0.2.

In one embodiment, the inventive process may provide for a relatively uniform shear stress while employing multiple process microchannels. To measure the shear stress uniformity among multiple process microchannels, the average shear stress is calculated for each channel and compared. $F_{max}$ is the largest value of the average channel shear stress, and $F_{min}$ is the smallest value of the average shear stress. $F_{mean}$ is the mean of the average shear stresses of all the channels. SFDF may be calculated from these values. Among multiple process microchannels, at least with one embodiment of the inventive process, the SFDF may be less than about 2, and in one embodiment less than about 1, and in one embodiment less than about 0.5, and in one embodiment less than about 0.2.

Overall, the shear stress in the microchannel is much higher than the shear stress in a larger channel. The minimum wall shear stress is preferably at least 1 Pa, and more preferably greater than 10 Pa on average for a microchannel.

Partial boiling allows very good control of the wall temperature between the boiling fluid and the alternate unit operation. The wall is nearly isothermal along its length and is stable to perturbations in process conditions within a process control operating window, including flowrate, inlet temperature, inlet pressure, and others. Many unit operations have advantageous performance from the control brought by partial boiling, including exothermic chemical reactions, distillation, adsorption, absorption, condensation, mixing for emulsions, mixing for increased solubility, and fermentation.

Exothermic chemical reactions are often plagued by undesired side products that are favored at higher temperatures. As heat is evolved from the primary and desired reaction route it often cannot be removed at the same rate as generated by conventional heat exchange equipment. A faster rate of heat removal through the use of partial boiling allows the exothermic reaction to be operated closer to isothermal and thus reduce the rate of unwanted products. In addition, many exothermic reactions become more equilibrium limited at higher temperature, the water gas shift reaction is one example. A desired outcome is to run the reaction at a higher temperature at the front end of the reactor and at a cooler temperature near the reactor exit. Multiple heat exchange zones may be disposed along the reaction length, whereby each uses partial boiling at a different temperature to reduce the reaction temperature along the length. The exothermic reactions may be either catalytic or homogeneous.

The reactant, or reactants, and catalyst may be selected for reactions such as: acetylation, addition reactions, alkylation, dealkylation, hydrodealkylation, reductive alkylation, amination, ammoxidation, ammonia synthesis, aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, dehalogenation, dimerization, epoxidation, esterification, exchange, Fischer-Tropsch, halogenation, hydrohalogenation, homologation, hydration, dehydration, hydrogenation, dehydrogenation, hydrocarboxylation, hydroformylation, hydrogenolysis, hydrometallation, hydrosilation, hydrolysis, hydrotreating (HDS/HDN), isomerization, methylation, demethylation, metathesis, nitration, polymerization, reduction, reformation, reverse water gas shift, Sabatier, sulfonation, telomerization, transesterification, trimerization, and water gas shift.

Distillation is advantaged by careful control of the phase equilibrium temperature within multiple stages along the length of the distillation unit. Partial boiling will allow very nearly isothermal operation in each stage. This will allow the ability to tailor the amount of energy added in each stage to reduce the overall energy input.

Adsorption, especially thermal swing adsorption, is advantaged by the rapid addition or removal of heat during the desorption and adsorption stages respectively. Partial boiling allows for the desorption staged to be operated more closely to isothermal over the cycle time rather than have a range of temperatures as created by convective heat removal using a fluid. A more isothermal temperature profile during desorption should allow for a higher recovery of the sorbates from the adsorbent and thus an overall higher system efficiency.

Absorption processes rely on a sorbate solubilizing in a working fluid during absorption before flowing to a desorption unit. The heat of absorption released during fluid uptake is not insignificant and may reduce the overall capacity of the working fluid. Near isothermal operation during absorption would increase the uptake of the absorbate and the system efficiency. In addition, partial boiling during desorption could allow the desorption cycle to operate near isothermal operation and reduce the time required for desorption through efficient heat transfer.

The conjoined operation of partial boiling and condensation offers advantages of higher heat transfer efficiency and reduced hardware size. Heat integration in commercial chemical plants is an important component of optimizing capital and operating costs. The integrated heat transfer of a condensing and boiling fluid may reduce the need for additional working fluids for each unit operation.

Exothermic reactions that can be aided by microchannel partial boiling include polymerization reactions. The inventive concepts described can achieve high heat transfer rates over long distances that would be needed for polymer processing. The ability of partial boiling to remove large reactor exotherms seen in the Trommsdorff effect can help suppress the process upsets that make bulk and solution polymerizations dangerous. The Trommsdorff effect is when the polymerization stream sees massive chain growth that results in a large exothermic heat release and the drastic reduction in the chain termination reaction step as a result of viscosity changes. The Trommsdorff effect may leads to a large increase in viscosity of the stream, thereby rendering the stream difficult to pump, as well as leading to large molecular weight polymers that can skew the molecular weight distribution or lead to insoluble pockets in the stream.

Heat released during mixing may not be insignificant for many fluidic mixtures. As the temperature of the fluid mixture increases the properties may also change, including solubility, phase stability, and thermal and fluidic properties. Removing the heat of mixing with the use of partial boiling will allow for more isothermal operation and tailoring the final fluid mixture properties.

Fermentation processes are optimized by a more isothermal operation as afforded by partial boiling. Inadequate heat removal raises the temperature during the fermentation process and in turn this may reduce the stability of associated enzymes or yeast or alter the reaction pathways. As an example, the heat released from fermentation during wine making fermentation must be slowed down to preserve the quality of the final product. The ability to remove heat at a faster and more controlled rate with the use of partial boiling could reduce the time required to produce wine from many weeks or months to a few days or less. Further, one could imagine a microchannel wine making device with the active yeast bound on the microchannel walls to initiate the fermentation reaction coupled with microchannel heat removal (including partial boiling) on an adjacent wall. Further, the yeast could be adapted to the microchannel walls in a manner that either includes oak or other wood products. Further, one side of the microchannel wall, where the wine is produced, could be made from a disposable oak or other wood product array of wine synthesis channels. Alternatively, the entire device could be made from wood or material that enhances the product quality.

For a system where coolant flows through a matrix of aligned microchannels are used to remove a constant heat flux from a saturated inlet stream, small differences in the inlet channel mass flow rates from the average or target for the case of a tailored distribution can lead to large differences in outlet vapor quality and affect coolant flow distribution. Should a manifold design not ensure equal flows or nearly equal flows with a quality index factor less than 10% (quality factor is described in U.S. printed patent application Ser. No. 2005/0087767) through a matrix of equivalent connecting channels with the same wall heat flux, the channel with a lower mass flow rate than specified, it is expected that the constant heat input would increase the local quality throughout the channel and incur a larger pressure drop. This is seen in the Lockhart-Martinelli pressure drop equation (2) that has local quality dependencies of first and second order. Those channels to which the manifold delivers more flow will see a lower outlet quality than specified and conversely a lower local quality throughout the channel. The additional effect is a feedback mechanism that rewards a lower quality channel with more flow and penalizes a higher quality stream with less flow, further exacerbating flow maldistribution. This latter effect is dangerous for operation when the desired operation range is near the critical heat flux for the design flow rates. In those cases a flow maldistribution can lead to local heat removal instability that can endanger the unit operation being controlled by partial boiling. This is a major development challenge in the development of partial boiling systems.

The production of steam from convective boiling in nuclear reactors could be another application in which partial boiling could be crucial in temperature control. Convective boiling is used in cooling nuclear reactors, and potentially the inventions can increase the critical heat flux the system can handle, and proper manifold design can be used to remove large heat fluxes that would give rise to dangerous reactor operation.

EXAMPLE 1

Modifications of Boiling Fluid Properties

For many applications, heat removal with the use of a boiling fluid is a closed-loop process. Whereby the boiling fluid is cycled between the boiling unit where heat is captured to a condensation unit where heat is released to a second working fluid or the environment. For these systems, it may be desirable to add surfactant to the boiling working fluid. The surfactant may act to stabilize the small bubbles that are formed during the increased range of nucleate boiling in a microchannel unit operation. The stabilization of small bubbles formed may allow the partial boiling unit to operate with a higher degree of liquid boiling in pass. In other words, a process may be operated with boiling 10%, or 30%, or even 50% or more liquid may be evaporated in a single pass while preventing dryout or hot spot formation. The resulting reduction in total flowrate for the boiling fluid reduces the size of associated ancillary equipment, including pumps and valves.

EXAMPLE 2

Distributed Partial Boiling in Micro-Channels

Partial boiling heat transfer in microchannels is integrated with microchannel reactors to conduct exothermic reactions. The cooling channels can be arranged in various connection patterns to efficiently remove the reaction heat. From the partial boiling curve, the heat flux has a large positive gradient after the single phase cooling section. From the process side where exothermic chemical reactions take place, the heat flux peak typically occurs shortly after the beginning of the reaction zone. Its exact location is determined by reactant flow rate, the reactor dimension and the characteristics of the catalyst packed bed if the catalyst is used in the reactor. The typical heat flux curve from the process side shows that it peaks near the beginning the reactor. By designing the cooling channels with various types of connections, the heat flux curves from both process side and the cooling side can be aligned so that the partial boiling cooling can meet the desired the heat removal capability locally.

Figure 1:
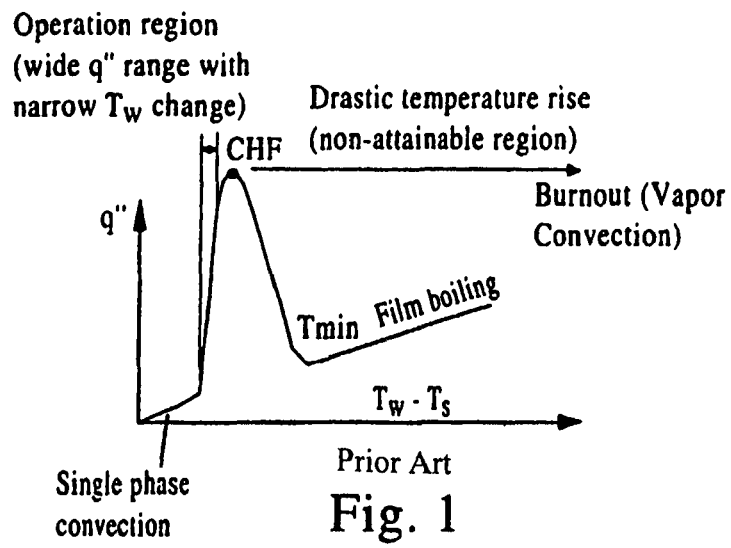
FIG. 1. A typical boiling curve
Figure 2:
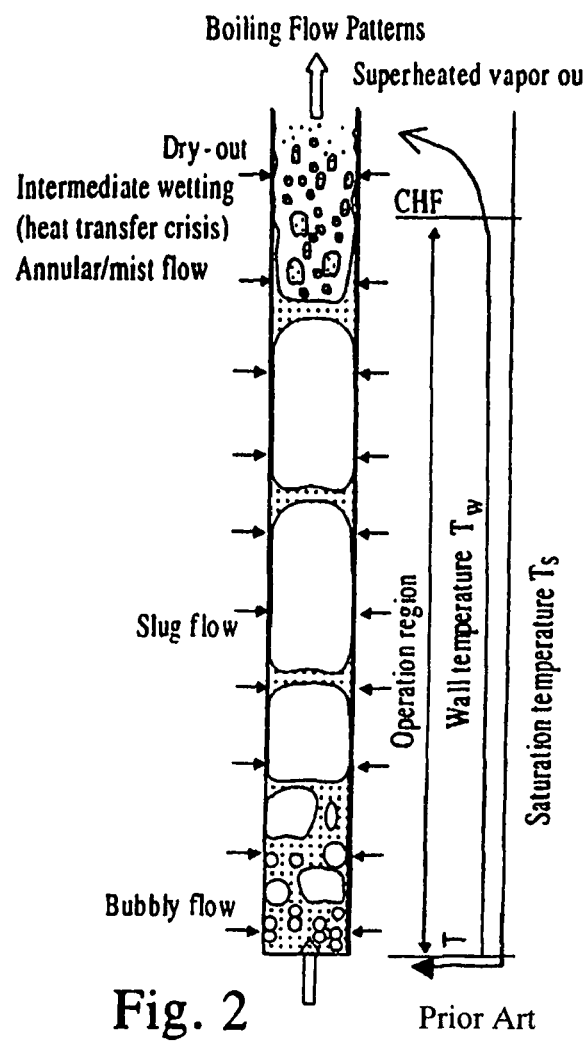
FIG. 2. Schematic of boiling flow patterns in a microchannel
Figure 3:
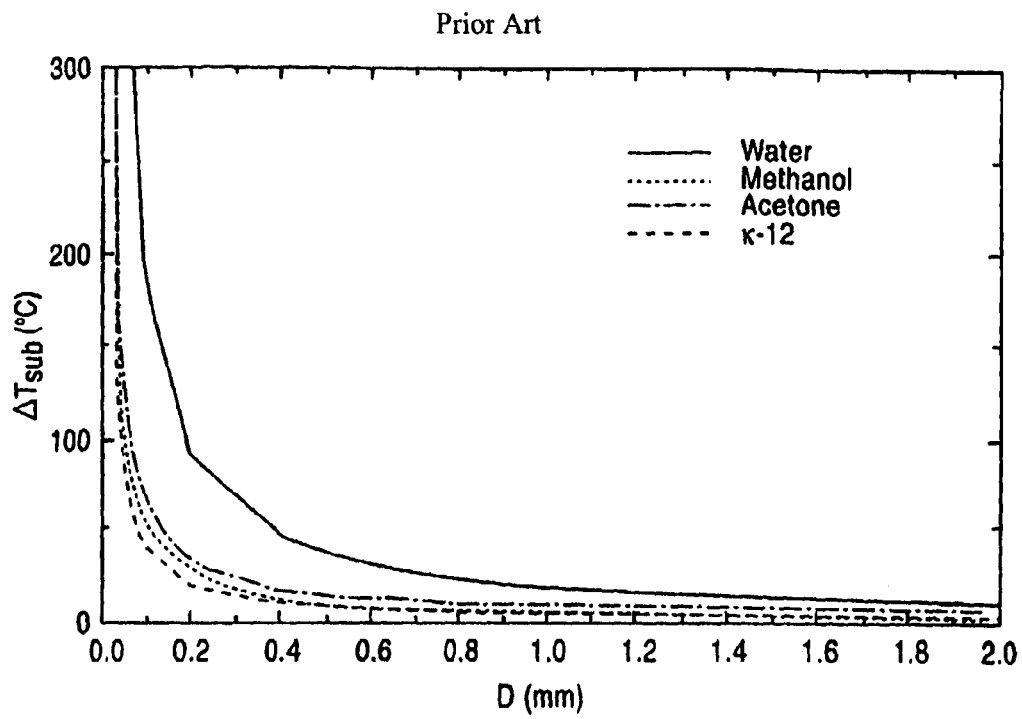
FIG. 3. Wall Superheat for Nucleation.
Figure 4:
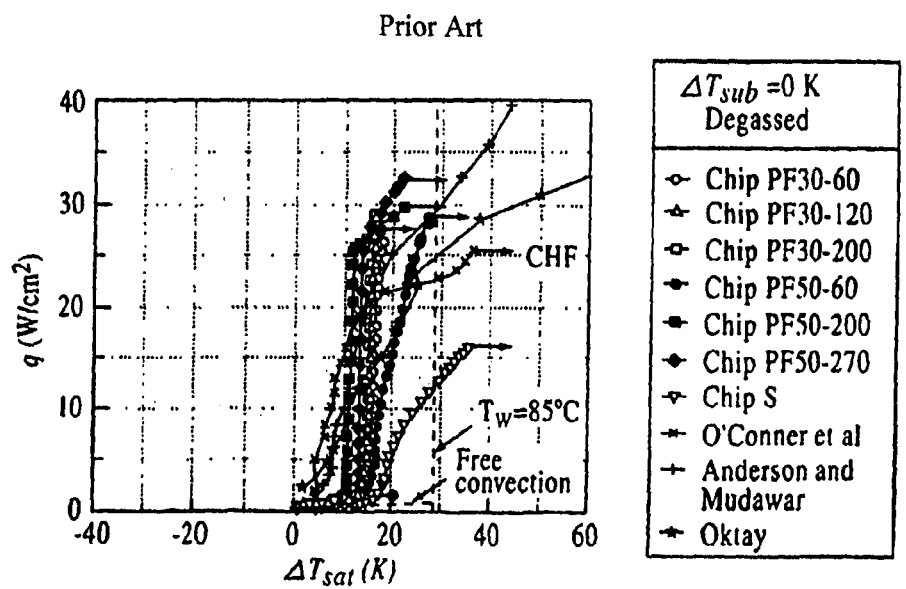
FIG. 4. Boiling curves; effects of porous structure and pin fin.
Figure 5:
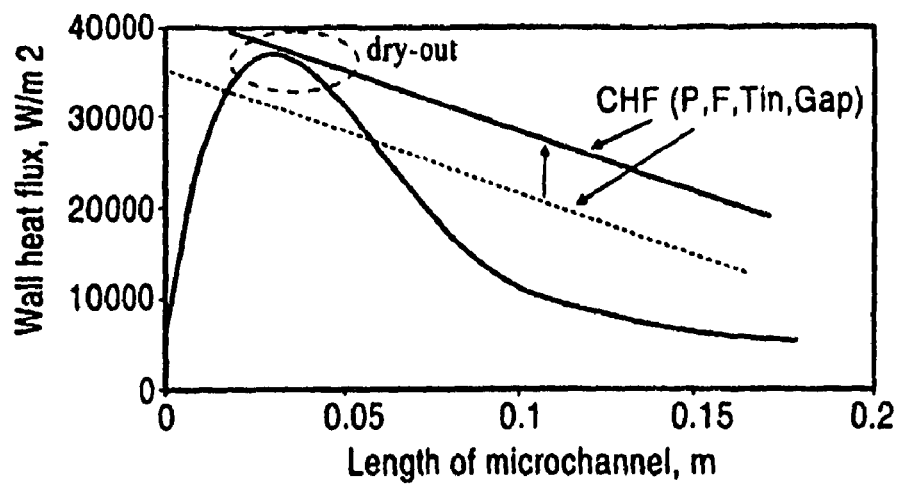
FIG. 5. Heat flux curve from process side vs. CHF curve
Figure 6:
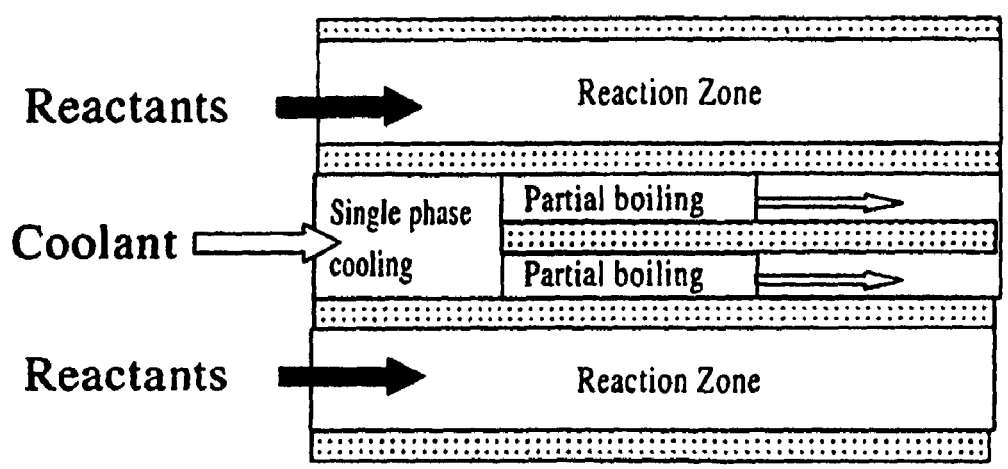
FIG. 6. Cooling Channel Split to increase CHF

FIG. 5 illustrates the main issue when designing the partial boiling heat transfer for exothermic micro-channel reactors. The heat flux from process side-requirement for iso-thermal operation-peaks after a short distance from the beginning of the reaction zone. The typical CHF curve has a negative slope along the cooling channel. With the dash-line CHF curve, given the conditions of pressure in the cooling channel, coolant flow rate, coolant inlet temperature and channel gap size, the dry-out will occur near the peak heat flux requirement. In order to make the partial boiling run stably, the parameters can be adjusted to give the CHF curve above the heat flux curve everywhere along the length.

Configuration 1: A cooling channel can be divided to improve performance for partial boiling. The coolant channel can have an initial area with single phase cooling followed by a second, subdivided region could have one, two or more walls dividing the coolant channels into subchannels in which partial boiling occurs; for example, subdivided into two channels each of which share a thermal transfer wall with a reaction channel. The division walls can be parallel or, more preferably, perpendicular to the height of the reaction channels so that heat is conducted through the wall directly from the reaction channel to the coolant channel.

Figure 7:
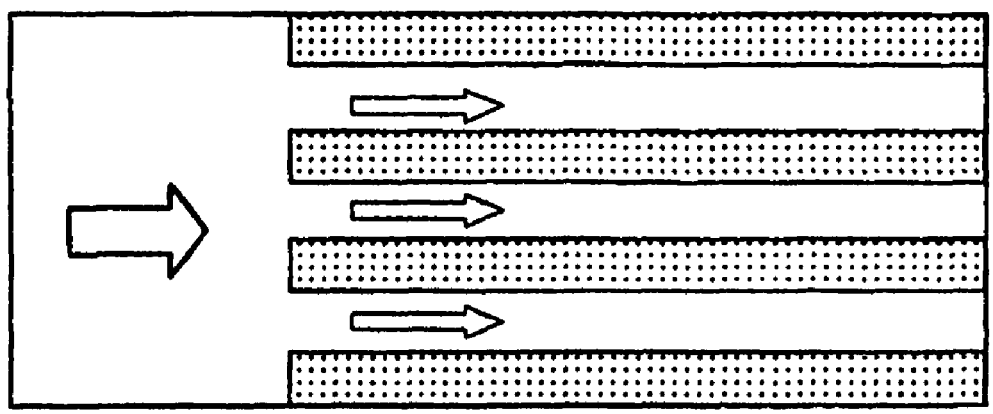
FIG. 7. Cooling channels subdivided into 3 channels. A process channel is disposed above and/or below the plane of the page.

Configuration 2: Single cooling channel is divided into several sub-cooling channels. See FIG. 7. The division location is designed to align with the peak of the heat flux profile from the process side. The smaller gap size of the partial cooling channels can achieve higher critical heat flux (CHF). Other design parameters are the dimensions of the sub-cooling channel, width (W) and gap height (H). The aspect ratio of W/H is in the range 5 to 10. By splitting the single cooling channel to several smaller cooling channels, all sides of the cooling channels are heat transfer surfaces. Compared to the cooling channels with the same size of the reaction channels, the heat transfer surface area per unit of the reactor volume is increased to 2 to 3 times.

Figure 8:
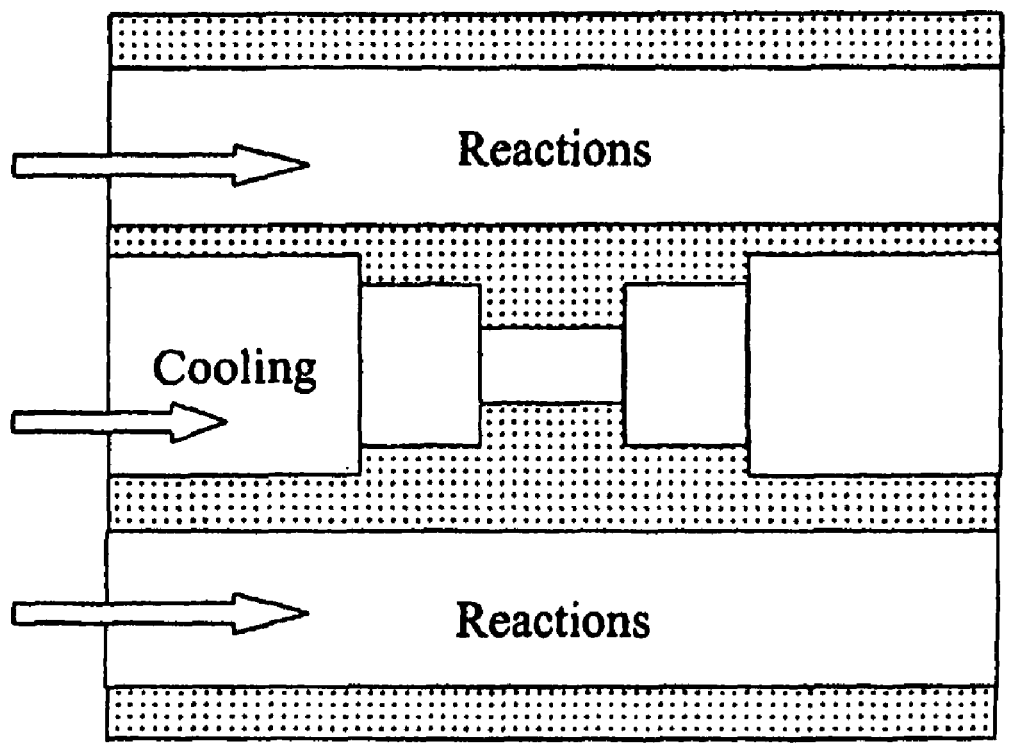
FIG. 8. Cooling channel with varying gap size.

Configuration 3: The cooling channel is designed such that the gap size varies along the cooling channel. The cooling fluid stream speeds up where the gap size is small. The higher critical heat flux is able to achieve locally where the gap size is small. The exact gap size profile is designed upon the heat removal need from the process side. See FIG. 8.

EXAMPLE 3

Partial Boiling in Micro-channel

A stainless steel device was fabricated to test partial boiling in micro-channels. The device was made by welding two stainless steel plates with milled micro-features that on assembly made micro-channels. Stainless steel plate 1 combined with stainless steel plate 2 to produce micro-channel flow paths. The total length of the plates and hence the micro-channels was 60 cm. The total width of the plates was 1.5(3.8 cm). The nominal thickness of both the stainless steel plates is 5/16 (8 mm). A chamfer was made at the outer edge of the plates to facilitate welding of the plates.

Figure 9:
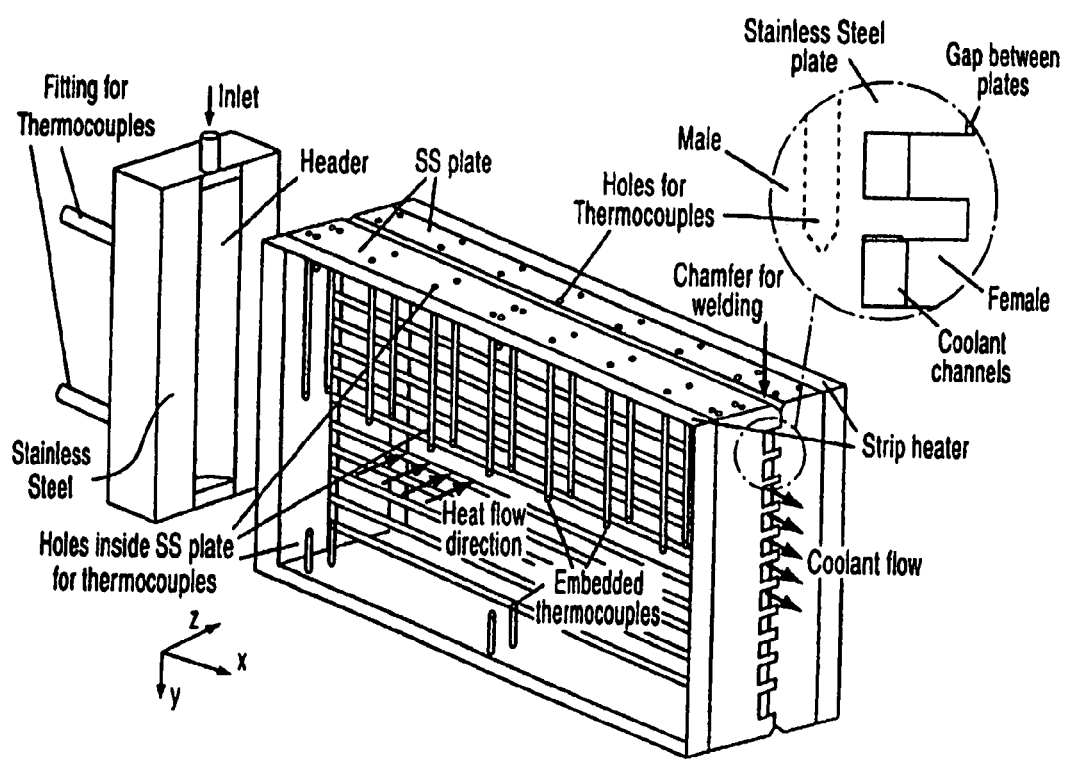
FIG. 9. Schematic of device for partial boiling

The micro-channels formed by combination of the two plates had cross-sectional dimension 0.030"×0.018". The length to hydraulic diameter ratio was 1067. The micro-channels were separated by a metal wall of thickness 0.018". A total of 14 such micro-channels were formed. Holes were drilled in the stainless steel plates along the length of the micro-channels (both 0.8 cm×60 cm face) as shown in FIG. 9.

The purpose of the holes was to insert thermocouples and estimate heat flux using the measured temperature. The diameter of all the holes is 0.022" and Type K 0.020" thermocouples were used for temperature measurements. FIG. 9 shows the schematic of layout of thermocouples on the stainless steel plate.

Thermocouples were located at total of 9 locations along the length of the micro-channel (60 cm direction) on both stainless steel plates. The distance between each location is 2.95". At locations 1 to 9, two thermocouples are placed at each location, both going 0.75" deep into the stainless steel plates. At each of these locations, the two thermocouples were located 0.01" from the edge of the plates as shown in View I-I in FIG. 10.

Figure 10:
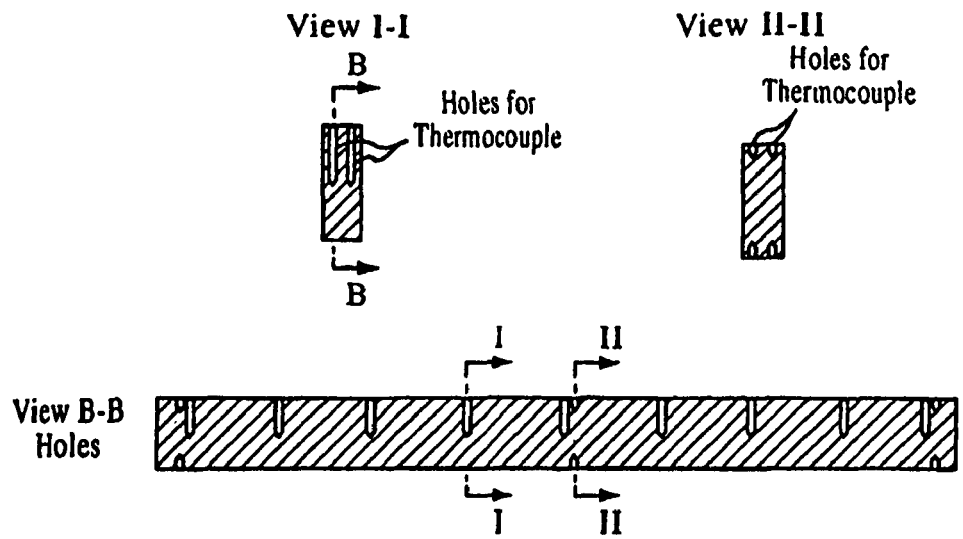
FIG. 10. Schematic of thermocouple locations in device of FIG. 9.

Four additional thermocouples were placed. These thermocouples went 0.30" deep into the plate and were offset from 0.75" deep thermocouples by a distance of 0.04" as shown in FIG. 10. At each of these locations, two thermocouples were placed on the same side of 0.75" deep thermocouples while remaining two thermocouples were placed on opposite side as shown in View II-II. The tub-like header and footer were dimensionally identical and were designed for uniform flow distribution of inlet flow.

Figure 11:
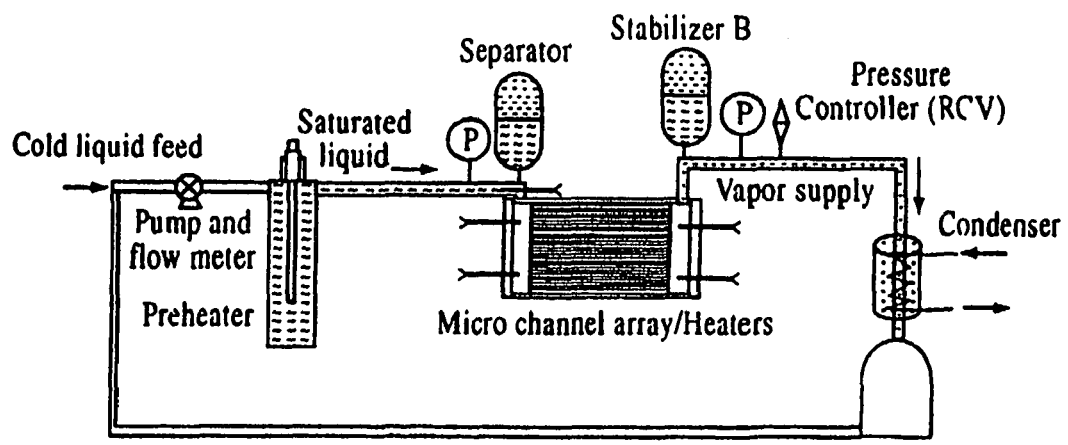
FIG. 11. Schematic of test loop for testing partial boiling device of FIG. 9.

Two strip heaters on 60 cm length and 3.8 cm width were placed on both sides of the welded plates as shown in FIG. 9. These heaters provide heat to the fluid in the micro-channels for boiling. The test loop to test the performance of the device is shown in FIG. 11. The test loop was a closed loop system. Water was used as a fluid and was also referred as coolant occasionally. The pressure of system was maintained 507 psig at the inlet of the device. The preheater heated the water to saturation temperature. Any vapor generated was removed by a separator at the inlet of the device. Heat was provided to the fluid using the strip heaters to partially boil the fluid. The partially boiled fluid was then sent through the condenser to cool it down below condensation temperature and send it back to pump where water was pressurized again before sent to the preheater, thus forming a closed loop system. An inline pressure controller was installed to regulate the system pressure.

Figure 12:
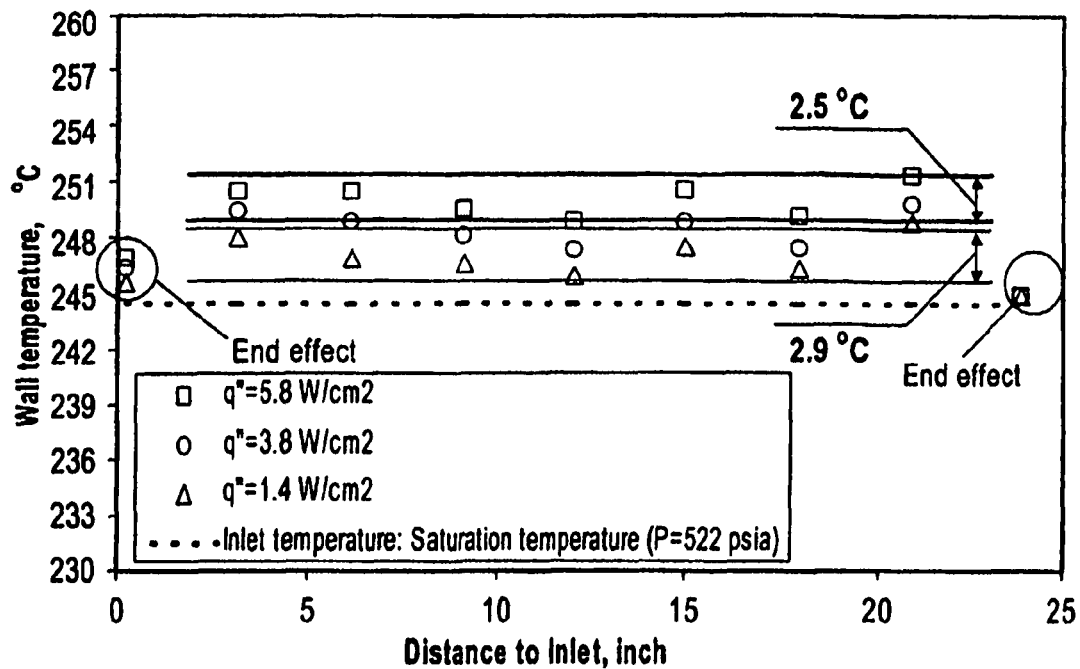
FIG. 12: Variation of wall temperature along the flow length at different heat fluxes
Figure 13:
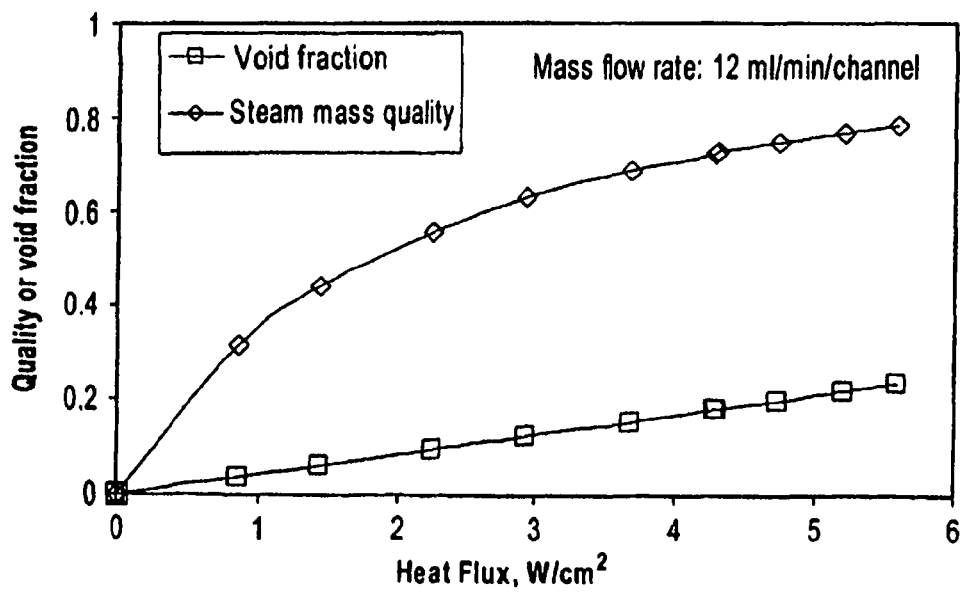
FIG. 13: Variation of outlet quality or void fraction with heat flux

The tests were performed at a flow rate of 12 ml/min/channel. A steady state operation of partial boiling was been achieved in the extraordinarily long micro channel array with water as coolant, as shown in FIG. 12. The device was operated at various heat flux rates from the strip heaters (as indicated in FIG. 12) and a constant temperature was obtained near the walls of the channel indicating successful partial boiling. The Boiling number at $q''=5.8$ W/cm$^2$ is $7.2\times10^{-5}$. The SR number is calculated to be $7.8\times10^{-10}$. The variation of vapor quality at the outlet of the device is shown in FIG. 13.

Figure 14:
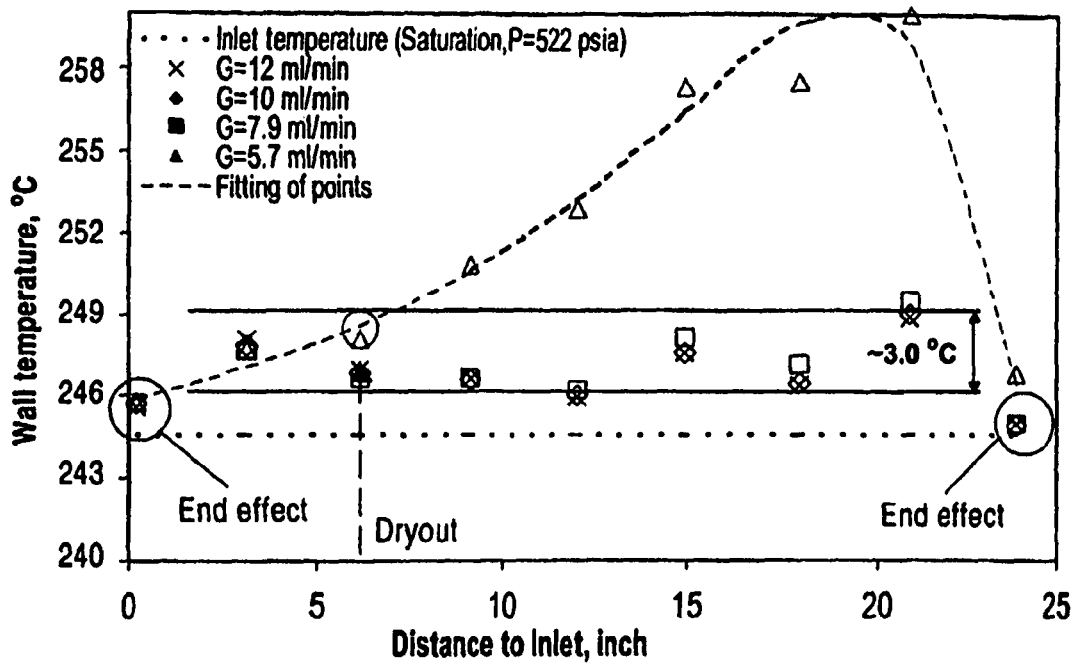
FIG. 14: Effect of mass flow rate on wall temperature profile FIG. 15. Pressure drop as a function of average heat flux for the 24 inch partial boiling test device.

The variation of wall temperature profile along the length of the channel with inlet mass flow rate is shown in FIG. 14. As we can see from the figure, at flow rates=12, 10 and 7.9 ml/min/channel, the wall temperature is maintained in a tight temperature band of 3° C. indicating partial boiling in the channels. However when the flow rate is reduced to 5.7 ml/min/channel, the wall temperature starts increased indicating a complete vaporization in the channel.

The back pressure regulator used on the outlet of the test system had a 25 second period of oscillation with 2 psig amplitude. The gentle oscillations shown on the performance curves result from the back pressure regulator and not from the partial boiling process. The very small pressure variation (less than 2 psi) demonstrated stable performance in time.

The inventive processes should be stable. Stability here for a microchannel boiling process is defined as follows: partial boiling is considered stable when only low fluctuation amplitude variations in measured flow pressure equal to or less than 5% of the average absolute operating pressure of the system and a characteristic oscillation frequency of a ratio less than 20 (peak amplitude to noise amplitude). Thus for instance, the maximum peak-to-peak oscillation in pressure is 5 psid and the average operating pressure is 505 psig=520 psia. Therefore the oscillation to operating pressure ratio is 5 psid/520 psid=0.96%<5%. Furthermore, the accuracy of the pressure tap transducers used in this experiment were at most 0.5% of full pressure loading at 1000 psia or 5 psi and thus the peak to noise ratio=5 psid/5 psi=1<20.

Channel aspect ratio (ratio of width to height) is another consideration for stable, partial boiling. Channels with low aspect ratio experience more bubble confinement during the onset of bubble nucleation at the surface. This in turn leads to conditions that promote bubble coalescence ultimately resulting in Taylor bubbles or slugs of vapor that occupy nearly the entire cross-sectional area of the channel. These conditions can lead to unstable two-phase flow systems. High aspect ratio channels, on the other hand, provide a greater degree of freedom in the channel width dimension to expand without encountering another nearby bubble before surface detachment. Furthermore, the persistence (lifetime) of Taylor bubbles (vapor slug) is dependent in part upon the geometry of the bubble. Cylindrical bubble slugs that, for instance, occur in tube flow are regarded as very stable and will persist for long periods of time. Taylor bubbles forced to take place in high aspect ratio channels will have a large relatively flat surface (such as a bubble squeezed between two parallel plates). The flat surface of the bubble cannot take on a more stable cylindrical or spherical shape which minimizes free surface energy, and therefore smaller perturbations in the flow field can destabilize the Taylor bubble and break it up into smaller bubbles. Therefore, high aspect ratio channels, namely of aspect ratio equal to or exceeding 5, more preferably equal to or exceeding 10, promote more stable partial boiling.

Figure 15:
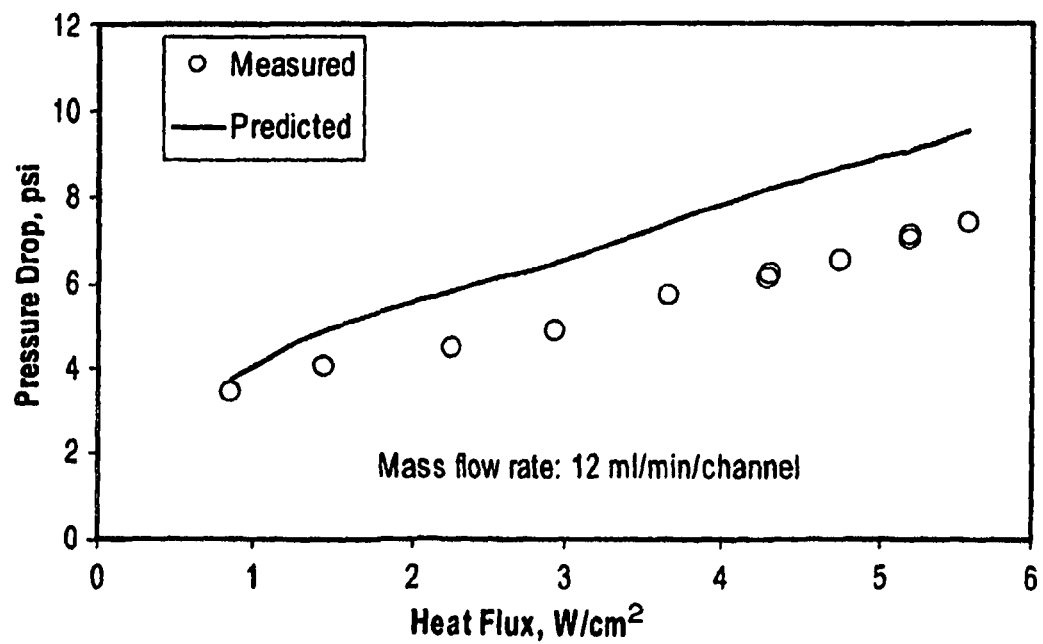

FIG. 15 shows the variation of pressure drop with average heat flux for the device. As the heat flux increased, more liquid was evaporated and hence the pressure drop increased.

Figure 16:
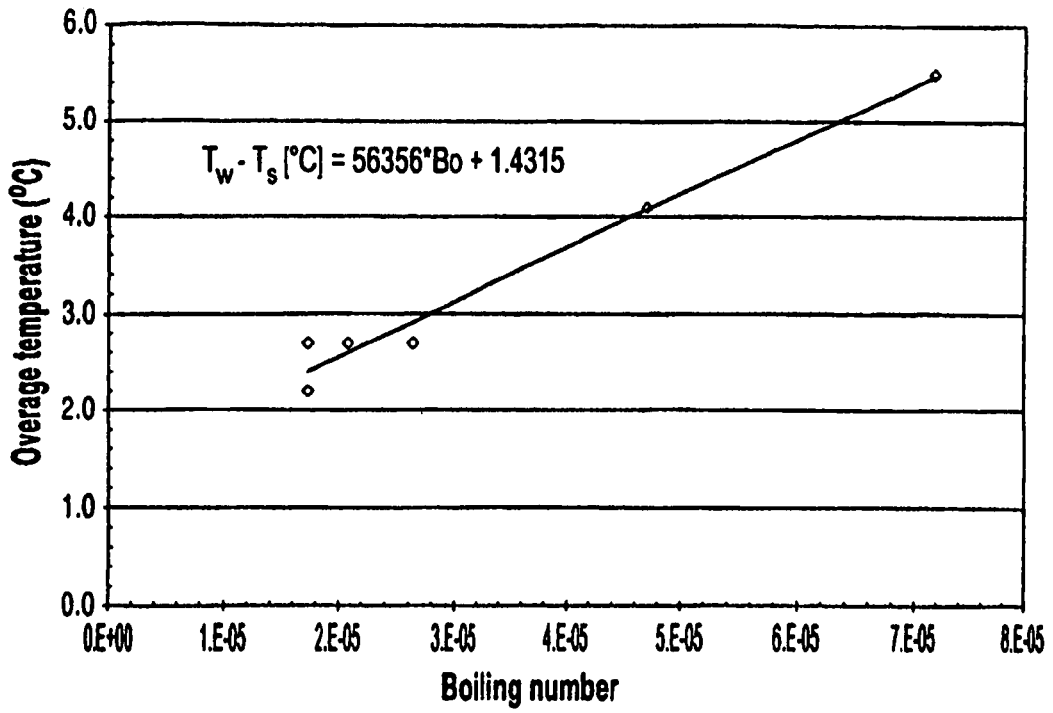
FIG. 16. The overance temperature vs. boiling number.
Figure 17:
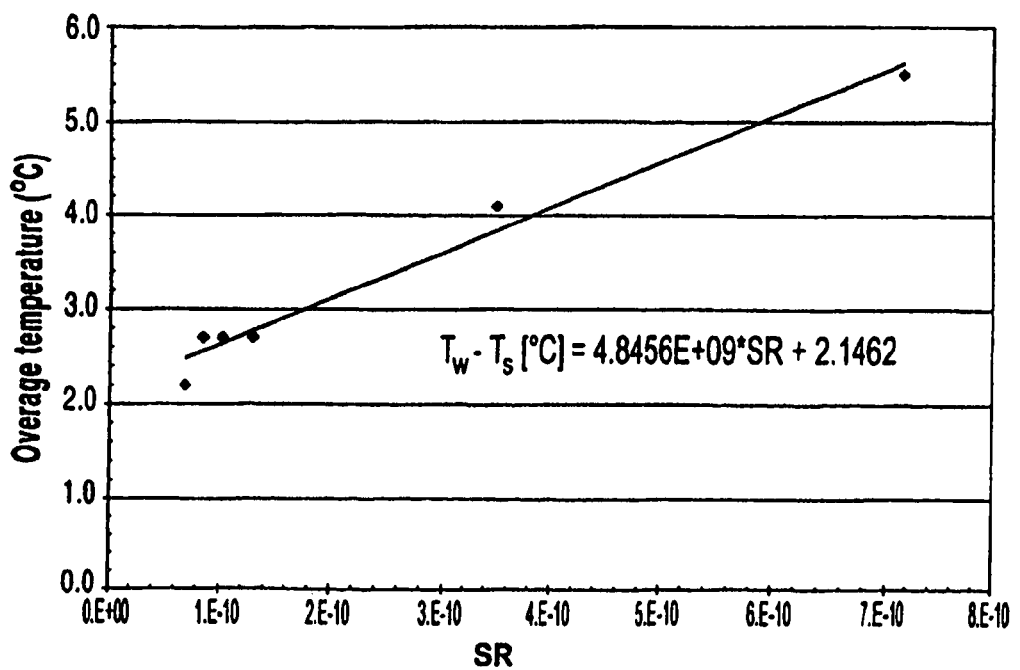
FIG. 17. The overance temperature vs. SR ratio.
Figure 18:
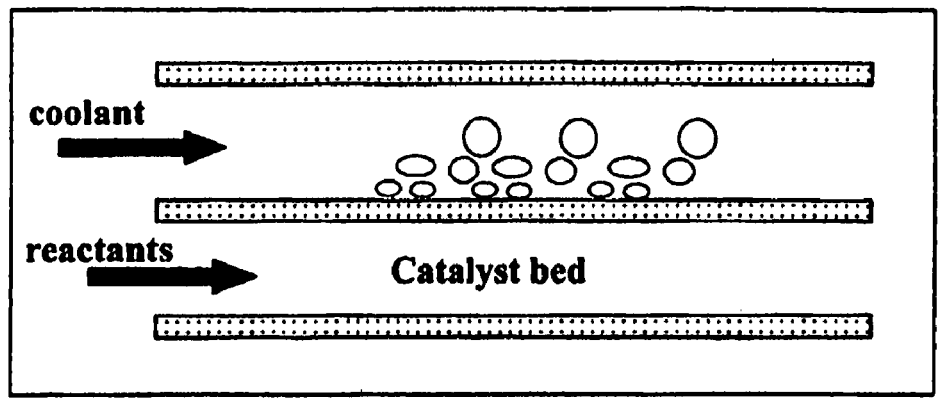
FIG. 18 Micro-channel reactor for VAM production.
Figure 19:
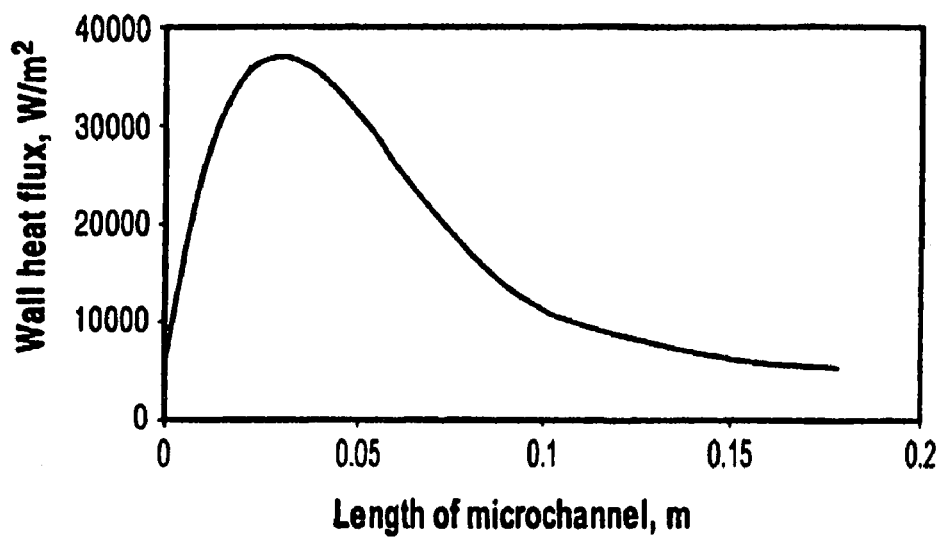
FIG. 19. Heat flux profile on the channel wall (mass flow rate on the process side is 146.2 Kg/m$^2$s).

FIGS. 16 and 17 compile the overage temperature, the difference between the average (excluding the two end points) wall temperature ($T_w$) and the saturation temperature ($T_s$), versus the boiling number (Bo) and the SR number, respectively, for the data described in FIGS. 12 and 14. This data set excludes the data point where dry out occurred in FIG. 19, as it isn't indicative of the high heat transfer convective boiling seen for the other data. The area beneath the points for both FIG. 16 and FIG. 17 indicates as stable nucleate boiling operation.

The shear stress during boiling for this example had an average of 7.5 Pa, a maximum shear stress of 10.6 Pa and a minimum shear stress of 1.7 Pa at a flowrate of 12 mL/min per microchannel of water for the 24" channel. For this case, the shear rate average over the channel length was 7425 hz, the maximum shear rate was 10253 hz, and the minimum shear rate in the channel was 2036 hz. The shear stress and shear rate was calculated using computational fluid dynamics based on the channel geometry, flowrate per channel and the flow regime, where the Reynolds number is less than 2000 for a laminar flow.

EXAMPLE 4

Partial boiling heat transfer is applied to vinyl acetate monomer (VAM) production in micro-channels. The microchannels by combination of the plates had cross-sectional dimension 0.05 mm×1.3 cm. The gap on the reaction side is 1 mm and on the coolant side is 1 mm. On the reaction side, a mixture of ethylene (C2H4), acid gas (CH3COOH) and oxygen (O2) is fed at temperature 160 C and pressure 8 atm. The micro-channel is packed with micro-pellet catalyst with a void fraction around 0.4.

The VAM producing reaction release heat into the packed bed and then the heat conducts through the channel walls to the surface on the coolant side, where the coolant vaporizes. The coolant used in this example is water. At the beginning of the catalyst bed, the reactants are at the highest concentration level and the reaction rate is at the maximum. This leads to the asymmetrical temperature profile along the catalyst bed. Accordingly, the heat flux profile on the channel wall (FIG. 19) also shows the peak neat the inlet of the reactor.

Figure 20:
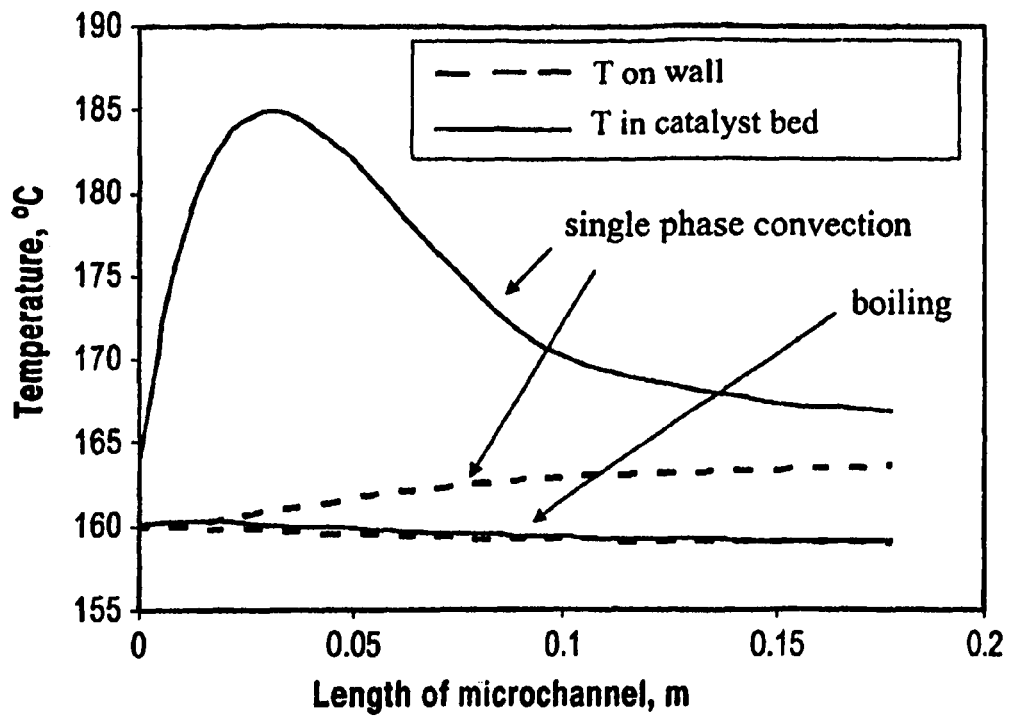
FIG. 20. Temperature profiles along the reactor length using different heat removal schemes. (mass flow rate on the process side is 146.2 kg/m2/s, $T_{in}$=160° C.).

The temperature hot spot near the beginning of the catalyst bed is detrimental to the selectivity of the desired product—VAM and the product yield. Also, the catalyst life time will be shortened due to the high temperature. It is desirable to operate the VAM reactor at the iso-thermal condition, or temperature variation along the reaction path within the tight range. In FIG. 20, temperature profiles along the reactor length using various heat removal schemes are compared. It clearly shows that the temperature variation along the reactor length is much tighter when partial boiling is applied to remove the heat. Another advantage of applying partial boiling heat removal is that high active catalyst can be used to give temperature profiles without large spikes, meanwhile the single phase cooling is not feasible under this condition.

Figure 21:
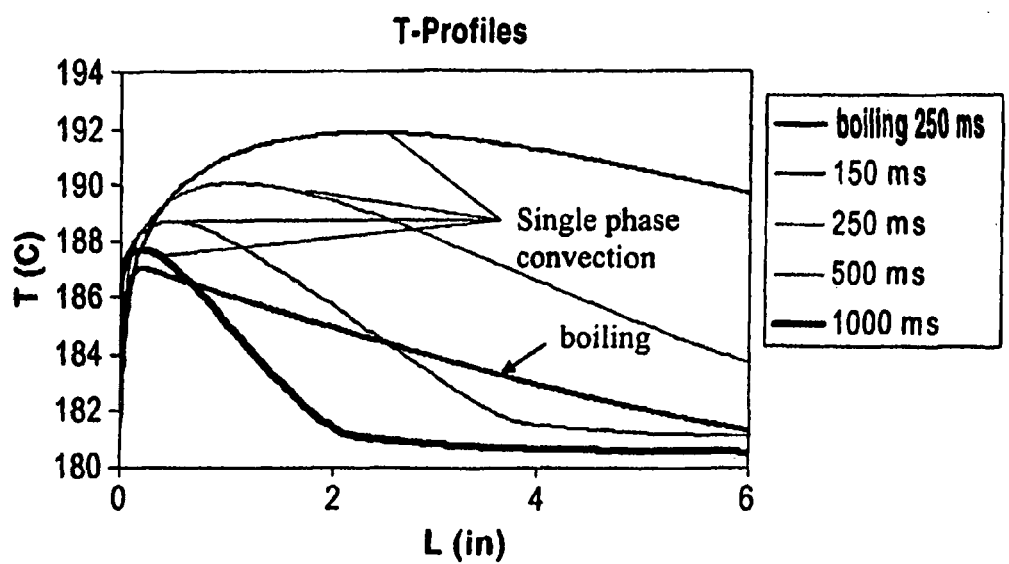
FIG. 21. Temperature curves along centerline of catalyst bed for the microchannel VAM reactor. Comparison of partial boiling with single phase convection heat transfer Tin (process)=180° C.; Tin (cooling)=180° C.; V (cooling)=0.3 m/s FIG. 22*a*. Main body of an FT reactor according to Example 5. The holes on the top face are thermowells.

The partial boiling heat transfer integrated with the microchannel VAM reactor enable operation under higher process output. FIG. 21 shows the temperature profiles along the centerline of the catalyst bed under four contact time levels with single phase heat convection as the heat removal method. The gap size of the coolant channel is 1 mm. The wall thickness is 0.5 mm and the channel gap on the process side is 1 mm inch also. The coolant flow stream has the average velocity of 0.3 m/s. Under lower contact time, or larger throughput, the temperature rise in the catalyst bed is larger. The design requirement of temperature rise is 10° C. above the inlet temperature, which is 180° C. in this case. With single phase heat convection as heat removal method, the reactor can not run at the contact time shorter than 250 ms. At 250 ms contact time on the process side, if partial boiling is the choice of heat removal method, the temperature rise in the catalyst bed is less than 10° C., well within the design allowable range.

EXAMPLE 5

Figure 22A:
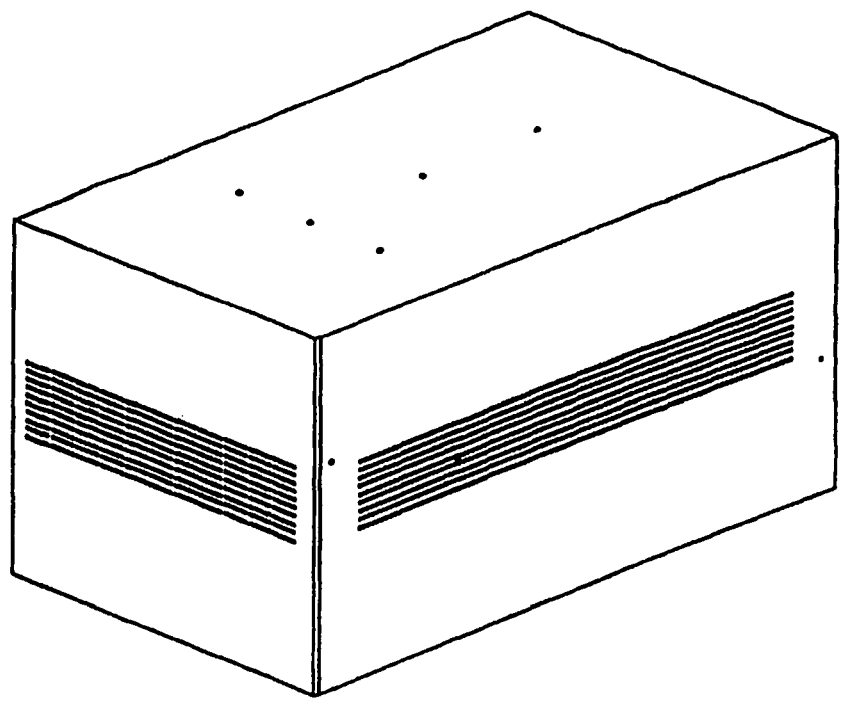
FIG. 22*b*. Exploded view of the reactor and the weldment of Ex. 5.
FIG. 22*c*. Time on stream temperatures for the multichannel cross-flow Fisher-Tropsch reactor of Ex. 5. "TC" is an abbreviation for thermocouple.

A multiple channel Fischer-Tropsch synthesis reactor was tested. The reactor designed had reactor unit operation channels for reactor microchannel in vertical orientation with flow in the direction of gravity. The heat exchanger microchannels were oriented in the horizontal orientation, cross-flow to the process channels. FIG. 22a shows the view of both sets of channels in the main body of the reactor. The reactor was constructed from stainless steel 316. There are 9 process channel that are 0.050 cm tall by 12.5 cm wide and 11.3 cm long, of which 7.5 cm are used for a catalyst bed. The catalyst bed was made up of an alumina support material with cobalt. There are 10 heat exchanger channel rows, with each row flanking a process channel. In each row there are 11 microchannels that are 0.750 cm tall and 0.270" wide and 15 cm long, with 0.030" separating channels in the row and 0.090" separating row from row.

Figure 22B:
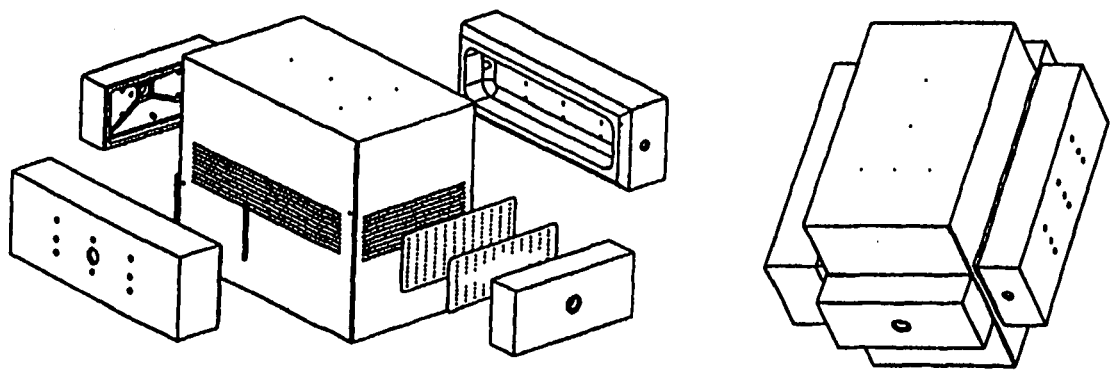

To get equal flow into all sections of the reactor, a set of orifice plates were used to push flow to the outside corners of the device, a problem seen in flow testing. These orifice plates are shown in FIG. 22b. Flow enters the header shown in FIG. 22b and distributes through the outer perimeter orifice and then through another straightener prior to entrance into the channels. Temperature measurement of the system's core was made through thermowells pictured in FIGS. 22a and 22b. These thermowells were close to the outer heat exchanger channels and would indicate the presence of temperatures higher than what is expected from partial boiling conditions.

Figure 22C:
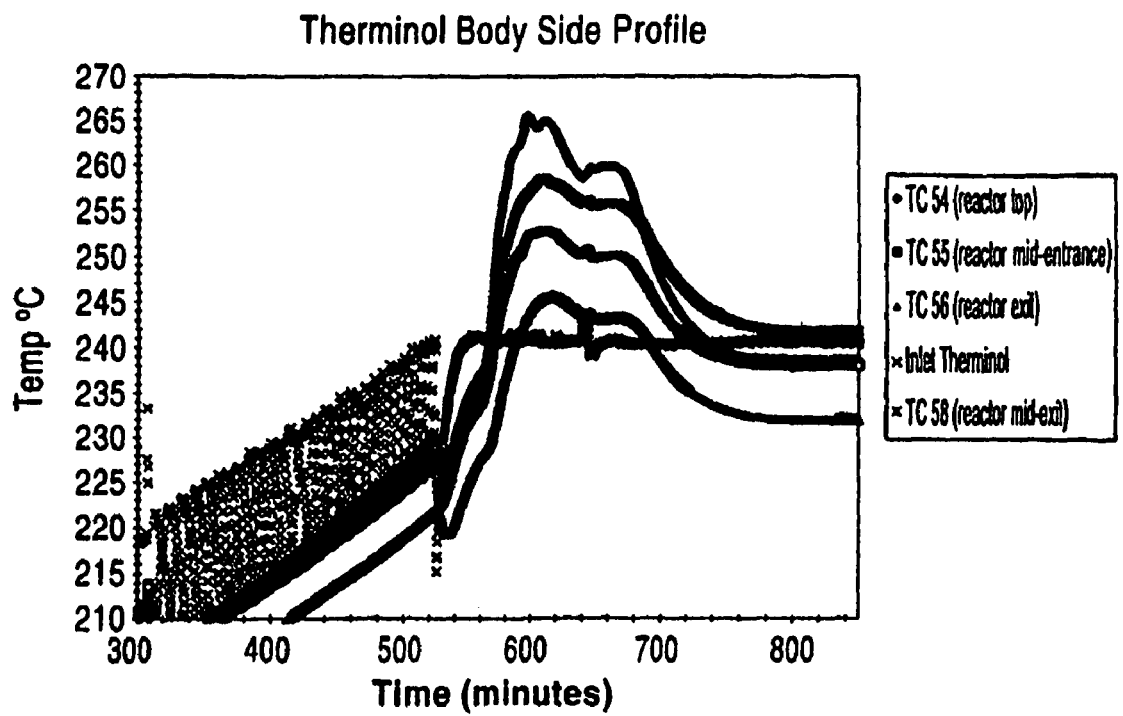
Figure 23:
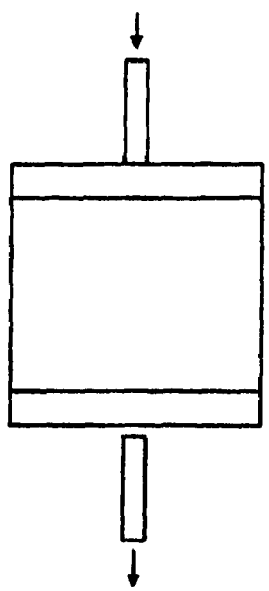
FIG. 23. Low Pressure Vaporizer Device Body with Water Side Header and Footer. The air header and footer are not shown.
Figure 24:
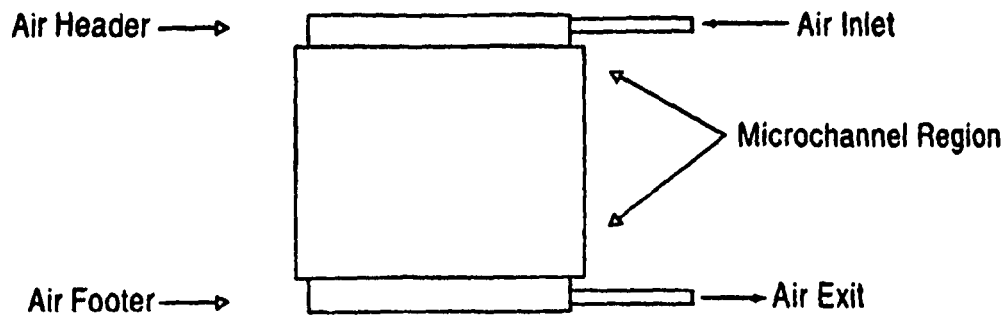
FIG. 24. Low Pressure Vaporizer Device Body with Air Side Header and Footer. The water header and footer are not shown.

THERMINOL LT™ (which is a commercially available synthetic aromatic heat transfer fluid that can be used in both the liquid and vapor phase) was fed at 50 mL/min and the reactor was fed a 2:1 molar mixture of hydrogen to carbon monoxide at a contact time of 250 milliseconds. FIG. 22c illustrates the time on stream data for the temperature ramp up to conditions and the initial performance. The reactor shows that the inlet coolant temperature varies during the temperature ramp up to the set point condition. Once the coolant reached the set point temperature the skin temperatures of the process spiked to values substantially higher than the boiling point of the coolant, with the highest readings seen for the inlet, or top, of the reactor bed. The skin temperatures drop in the direction of flow, but they all lie above the THERMI- NOL™ boiling point for an extended time. These elevated temperatures are indicative of dry out in a large number of channels. The high temperatures seen the top of the bed thermowell were indicative of dryout as they were substantially higher than the saturation temperature of the coolant at the design pressure. It shows that there may have been a large maldistribution of flow from the top to the bottom of the channel, as the bottom has a lower temperature (close to the boiling operation temperature) and the positions closer to the top substantially higher in temperature. This profile indicates that we may have had biased coolant flow: More flow in the channels near the reactor outlet and less at the top of the reactor channel. When the heat exchanger channel dries out the gas phase pressure drop can be much larger than in the partial boiling channels, making the problem one of flow distribution design in addition to convective boiling. During this time it is believed that the Fischer-Tropsch catalyst deactivated at the elevated temperatures.

EXAMPLE 6

A series of experiments was run to evaluate partial boiling and assess the fouling effects in microchannels when partial water boiling occurs. Accelerated tests with either 0.5-1 ppm or 10-20 ppm total dissolved solids (TDS) were operated to quantify the impact of fouling on the boiling side of the partial vaporizer.

Device Description:

Two low pressure and one high pressure partial vaporizers were operated, and the device descriptions follow. For the low pressure vaporizers, the water side consists of 12 channels, each 1" wide×1" long×0.020' gap. The air side consists of 11 channels, each 1"×0.020"×1". The overall design is a cross-flow pattern. The air and water channels alternate, with a water channel being the outermost channel on both sides. The device was oriented such that the water would flow vertically upward (opposite gravity), and the air flowed parallel to horizontal.

Figure 25:
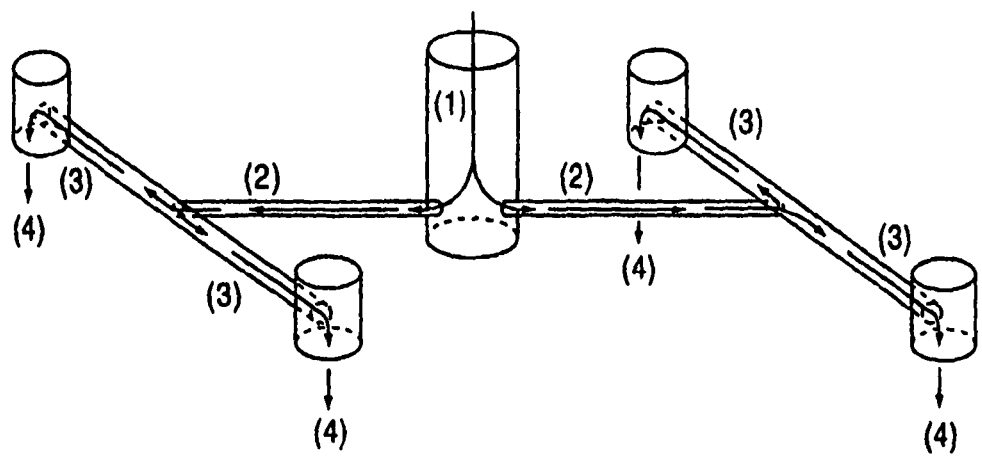
FIG. 25. Low Pressure Vaporizer Water Header
Figure 26:
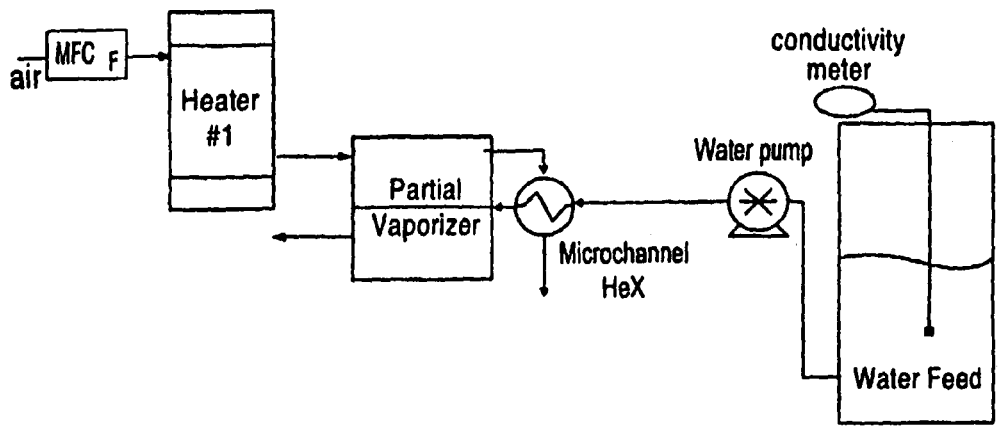
FIG. 26. Partial Vaporizer System Sketch.

The internal design of the header is shown in FIG. 25. The circular channel indicated with '1' is 0.180" ID, channel '2' is 0.031" ID, channel '3' is 0.063", and channel '4' is 0.100". The water flowed vertically upward into 'tube 1' (the drawing is upside down from the orientation the device was operated).

Low Pressure Vaporizer Water Footer

The internal design of the footer is simply a pyramid shaped cavity measuring 1"×1" at the start of the footer (by the microchannels), tapering down to a 0.180" circular exit opening.

Prior to the actual long term operation, acrylic devices were constructed to evaluate water flow distribution through the headers, microchannels and footers in the low and high pressure vaporizers. Using deionized water and food coloring as dye, the colored water flowed through the devices at flowrates equal to that of the actual long term operations, and the results were videotaped. The videos were reviewed to determine if flow was evenly dispersed, and changes to the design were made if needed. For the low pressure vaporizer header, a four way splitting method was chosen which delivered water feed to the four corners of the microchannel region. For the high pressure vaporizer header, the choice of distribution plates was critical to achieving even distribution. The final designs that were chosen are presented previously.

Experimental Setup and Operation:

Two low pressure and one high pressure partial vaporizers were operated and full details follow. A flow diagram for the low and high pressure partial vaporizer test stands follows.

The partial vaporizers were operated by controlling the air inlet flowrate on the hot side of the vaporizer and the water flowrate on the cold side of the vaporizer. The air was heated via a conventional heater to the desired temperature prior to entrance into the vaporizer. The air flowed out of the partial vaporizer into a microchannel heat exchanger which preheated the feed water. Water was pumped out of the bulk supply through the microchannel heat exchanger into the partial vaporizer. The high pressure vaporizer had an additional task of maintaining a constant backpressure. The water and steam mixture upon exiting the partial vaporizer was cooled and condensed.

Type K thermocouples (TC) from Omega Engineering were installed on the outer surface of the partial boiling vaporizer, and at all inlet and outlet locations. The air feed Brooks 5851 e series mass flow controller, the NoShok pressure transducers model 1001501127 and 1003001127, Omega latching relay controllers model CNI 1653-C24, LabAlliance HPLC Series 3 water pump, and Swagelok variable pressure relief valves, etc were calibrated and verified for proper operation. Air flowrate was calibrated against a primary standard calibrator, the Dry-Cal DC-2M Primary Flow Calibrator, which was calibrated and certified by BIOS International. Pressure transducers were calibrated using a Fluke pressure calibrator model 718 1006 with a Fluke 700P07 or 700P06 pressure module which were calibrated and certified by Fluke. The water pump was a Lab Alliance Model IV HPLC pump. The Omega CDCE-90-X conductivity sensor was calibrated using conductivity standards purchased from Cole Parmer. The entire system was constructed with Swagelok 316 stainless steel tubing and fittings.

Each vaporizer system was pressure tested by applying a static pressure to the water inlet line while plugging the outlet line. The applied pressure was 80-90 psig for the low pressure vaporizers and ~360 psig for the high pressure vaporizer, and was generated using a nitrogen fluid. The pressure was left on this side of the device. Concurrently, the air side was pressurized to ~40 psig. If there the leak rate does not exceed 0.5 psig in 15 minutes, then the vaporizer system was ready for operation.

Each vaporizer system was started up by turning on the preheaters and the air flow to the values indicated in the run plan. When the system was within ~35-45° C. of the desired temperature as indicated in the run plan, then water was introduced to the system. The water was started at full-flow to avoid low flowrates that would have very high percent boiling and risk dryout in the channels. In the case of the high pressure vaporizer, the back pressure control valve was then adjusted until the desired operating pressure was achieved. The microchannel heat exchanger immediately upstream of each of the partial vaporizers was controlled at a temperature 10-20° C. below the boiling point at their respective operating pressures. A conductivity meter in the water supply tank provided continual monitoring of the supply water quality during operation.

Prior to full startup, system energy losses were measured by operating the system 10° C. below the boiling point and measuring the energy provided to and exiting from the system. The system losses initially ranged from 6 to 10% of the available energy in the system.

The following table lists the respective temperatures, pressures, and flowrates into and out of each vaporizer.

TABLE 1

Vaporizer conditions

|  | Low Pressure Vap. #1 | Low Pressure Vap. #2 |
|---|---|---|
| Air inlet temp (C.) | 250 | 372 |
| Air outlet temp (C.) | 132 | 207 |
| Water inlet temp (C.) | 86 | 85.5 |
| Water outlet temp (C.) | 104.6 | 100.3 |
| Air flowrate (SLPM) | 150 | 150 |
| Water flowrate (ml/min) | 28.4 | 20 |
| Water inlet pressure (psig) | 2.9 | 0.7 |
| Water outlet pressure (psig) | 2.6 | 0.1 |

Low Pressure Partial Vaporizer Number One
Operational Summary:

The first low-pressure vaporizer completed operation at 9125 hours (~380 days), and demonstrated no signs of degradation during operation. It operated at ~31% vaporization and was fed with ~1 ppm total dissolved solids (TDS) water. The composition of the water was ~0.29 ppm Ca, 40.13 ppm Mg, ~0.19 ppm phosphate, and ~0.15 ppm Cl. The energy provided to the vaporizer via the heated air feed was ~391W. The system heat losses measured prior to full system startup were 39W. The system operated at ~2.9 psig inlet pressure, and ~2.6 psig outlet pressure. The BO number during normal operation was 0.00326, and the SR number was $1.39\text{E}10^{-6}$.

Figure 27:
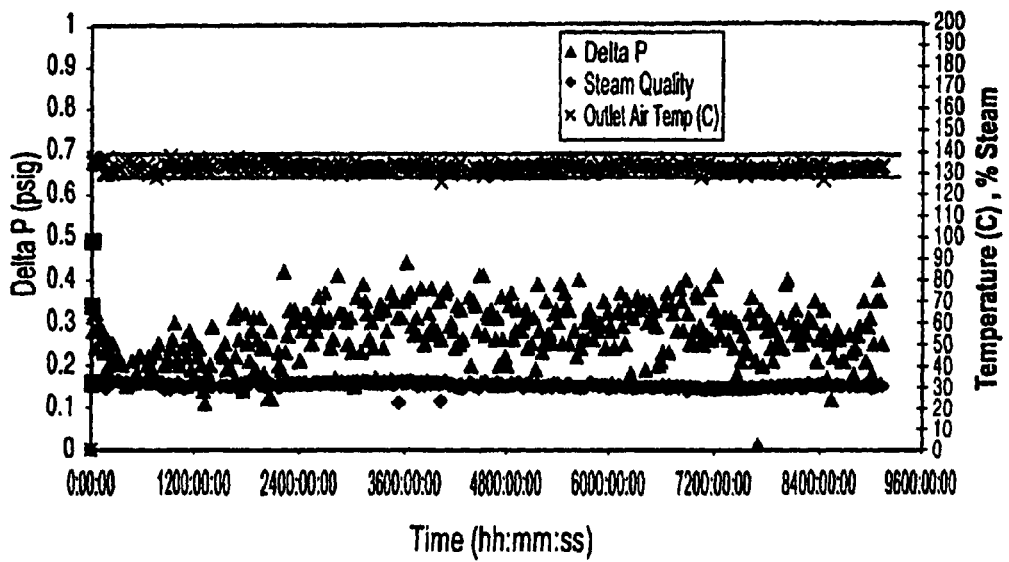
FIG. 27. Low Pressure Vaporizer, 1-2 ppm total dissolved solids.

Additionally, the system has endured ~14 cycles, or process upsets, without change in performance which demonstrated the durability of the partial vaporizer. A cycle is defined as a deviation from the expected normal operating condition. The variety of cycles include loss of water flow while the heated air maintained flow, loss of power to the air heater which caused the device to be cooled to room temperature, and loss of power to the entire system. During some cycles, periods of dry-out occurred within the partial vaporizer, however no scale deposition or buildup was observed, as is discussed in the next section in detail. Final data is shown in FIG. 27. The long term durability and overall effectiveness of the partial boiling vaporizer is demonstrated in Table 2 and Table 3. Table 2 shows the temperature difference between the water channel wall and the water/steam outlet temperature is small over the duration of the experiment. Table 3 demonstrates the unchanged vaporizer (i.e. heat exchanger) effectiveness before and after two types of cycles. Heat exchanger effectiveness is defined as the actual heat transferred by the air to the water divided by the maximum possible heat that can be transferred by the air.

TABLE 2

Low Pressure Vaporizer number one, Temperature Difference Wall to Water/Steam Outlet

| Steam/Water outlet (C.) | Device wall (C.) | Device Wall − Outlet (C.) | Total Time on Stream (hours) |
|---|---|---|---|
| 105.6 | 107.9 | 2.3 | 9125 |

TABLE 3

Low Pressure Vaporizer number one, Comparison of Vaporizer Effectiveness before and after cycles

| Type of Cycle | Duration (hours) | HEx Effectiveness before cycle | HEx Effectiveness after cycle |
|---|---|---|---|
| Loss of water flow | 20 | 0.73 | 0.73 |
| Loss of air heater | 2.5 | 0.72 | 0.72 |

Post Operation Analysis:

The device was analyzed for two effects, the first and more important effect was to look for signs of fouling on either the air or water sides, and the second effect was to look for material degradation such as pitting or corrosion.

The device was cut apart to visually observe no signs fouling or particulate buildup in the microchannels. The device was then cut into eight cubes such that the center channels of the device could also be seen, and again demonstrated no signs of fouling in either the air channels or the water channels. Using SEM, no obvious signs of pitting were observed. The EDS data indicate that there was an oxide scale on the surface that is rich in Fe, and Cr in some cases, likely from the underlying metal. Common hard water scale elements such as Ca and Mg were not present.

Figure 28:
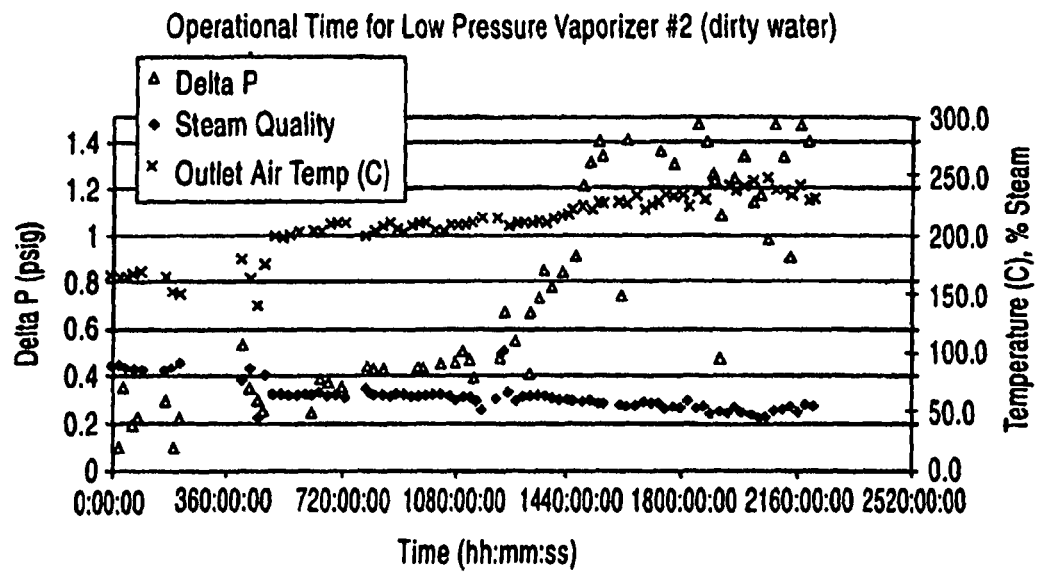
FIG. 28. Low Pressure Vaporizer, dirty water feed.

Low Pressure Partial Vaporizer Number Two
Operational Summary:

The second low-pressure vaporizer was operated 2041 hours. It was taken offline to investigate probable fouling. Fouling was suspected due to the decreased steam quality, and increased air outlet temperature (i.e. less heat being transferred to the water side). Data are shown in FIG. 28. The vaporizer operated with decreasing steam quality, from −85% to 50% and was fed with 12-15 ppm TDS water. The actual composition of the water was ~2 ppm Ca, ~0.9 ppm Mg, ~0.27 ppm Sr, ~0.67 ppm Cl, ~1.8 ppm sulfate, and ~7 ppm bicarbonate. The system operated at ~0.7 psig inlet pressure, and ~0.1 psig outlet pressure. The BO number during normal operation was 0.0068, and the SR number was $4.30\text{E}10^{-6}$.

This system also demonstrated durability as it endured ~9 cycles without change in performance. The upsets are the same as those listed in the low pressure vaporizer number one section. The long term durability and overall effectiveness of the partial boiling vaporizer is demonstrated in Table 4, which shows the unchanged vaporizer (i.e. heat exchanger) effectiveness before and after two types of cycles. Heat exchanger effectiveness is defined previously.

TABLE 4

Low Pressure Vaporizer number two, Comparison of Vaporizer Effectiveness before and after cycles

| Type of Cycle | Duration (hours) | HEx Effectiveness before cycle | HEx Effectiveness after cycle |
|---|---|---|---|
| Loss of air flow | 17 | 0.57 | 0.57 |
| Loss of system power | 3 | 0.54 | 0.54 |

Post Operation Analysis:

The water-side header and footer were removed and found to have scale deposits. The scale deposits also extended through the microchannel regions. Upon visual inspection with boroscope, the scale was located evenly throughout the microchannel region. Each channel appeared to have an equal amount of scale in similar areas. This indicates that flow was uniform through the microchannel region. Using SEM and EDS, the scale deposits were evaluated and found to contain a significant amount of Ca, Si, Mg and O, which are consistent with those elements in hard water scales. Additionally, the scale was found to contain matches to calcite, gypsum and other typical minerals found in hard water scale. Thus the probable conclusion is that the device suffered from typical hard water scaling. A calculation of shear stress and shear rate was done for these examples.

Geometry for low P vaporizer: 1×0.02×1, total 12 channels
Fluid: water
Flow rate: 20 (Vap. #2) and 28.4 (vap. #1) ml/min (total flowrate for device)
Calculation of Shear Rate and Stress.

|  | LP Vap. #1 | LP Vap. #2 |
|---|---|---|
| Shear rate: Max. (1/s) | 35.3 | 24.8 |
| Min. (1/s) | 5.65 | 4.0 |
| Avg.(1/s) | 34.8 | 24.5 |
| Shear stress: Max. (Pa) | 0.036 | 0.026 |
| Min. (Pa) | 0.0029 | 0.002 |
| Avg.(Pa) | 0.035 | 0.025 |

As noted in this example, the shear stress in the microchannel during the partial boiling operation was two orders of magnitude lower than the shear stress for the example described in example 3 with the long microchannels on the order of 24 inches.

Overall Performance Summary:

TABLE 6

Overall Partial Vaporizer Performance Summary

| Total Dissolved Solids (ppm) | Percent Boiling (%) | Operating Pressure (psig) | Time on Stream (hrs) | Onset of fouling (hrs) |
|---|---|---|---|---|
| ~1 | ~31 | 2.9 | 9125 | NA |
| 12-15 | initially 85 | 0.7 | 2041 | ~478 |
| ~1 | 40-50 | 294 | 6239 | NA |

EXAMPLE 7

Temperature Profile Advantage—Modeling Comparison

The high heat transfer characteristics of micro-channels enables partial boiling while maintaining low heat transfer wall temperature. The small temperature difference between the wall and the fluid in the micro-channels prefers nucleate boiling regime to film boiling regime and hence provide more stable boiling in the channels. A mathematical model was developed for partial boiling and the modeling results for micro-channel and large dimension channels were compared to demonstrate micro-channel advantage.

Figure 29:
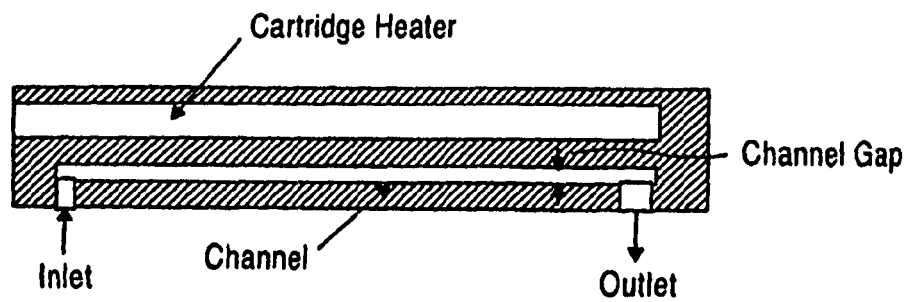
FIG. 29: Cross-sectional schematic of a microchannel vaporizer

The geometry of the vaporizer modeled is shown in FIG. 29. The heat for vaporization is provided by cartridge heaters. The fluid used for vaporization is methanol. The methanol enters the channel at room temperature (25° C.) and exit the channel at ambient pressure. The heat from the cartridge heater was adjusted to obtain 75% vapor quality (mass basis).

The width of the flow channel was 1.0" while the height of the channels was varied from micro-dimension to macro-dimension. The length of the channel was 4.0". The diameter of the cartridge heater was 0.375" and length of the heater was same as the length of the channel. The heater provided uniform surface heat flux. A construction material for the vaporizer was stainless steel. The metal wall between the heater and the channel was 0.02". A 0.25" perimeter was assumed surrounding the channel and the heater. Two cases were considered by varying the channel gap:

Case 1: Channel gap=0.050"
Case 2: Channel gap=0.375"

For both the cases, methanol flow rate of 3.7 ml/min was used. The heater setting was also kept constant. No heat losses to the surrounding were assumed in the model. Also at any cross-section perpendicular to the flow direction, the variations in metal wall temperature were ignored. Heat transfer coefficient for pure liquid phase was calculated from fully developed Nusselt number in rectangular channels.

$$h_{liq} = \frac{Nu \times k}{D_h} \quad (17)$$

Where,
Nu=Fully developed Nusselt number
K=Thermal conductivity of liquid, W/m-K
$D_h$=Hydraulic diameter, m
$h_{liq}$=Lqiuid heat transfer coefficient, W/m-K Heat transfer coefficient for pure vapor can also be calculated in similar manner.

For 2-phase system, the heat transfer coefficient was assumed to be dependent upon vapor quality. The maximum heat transfer coefficient was assumed to be 3000W/m2 K. The 2-phase heat transfer coefficient increased linearly with vapor quality from pure liquid heat transfer coefficient to maximum heat transfer coefficient (3000 W/m² K) from vapor quality=0 to vapor quality=0.5 and then decreased linearly from maximum heat transfer coefficient (3000 W/m² K) to pure vapor heat transfer coefficient from vapor quality=0.5 to vapor quality=1.

Figure 30:
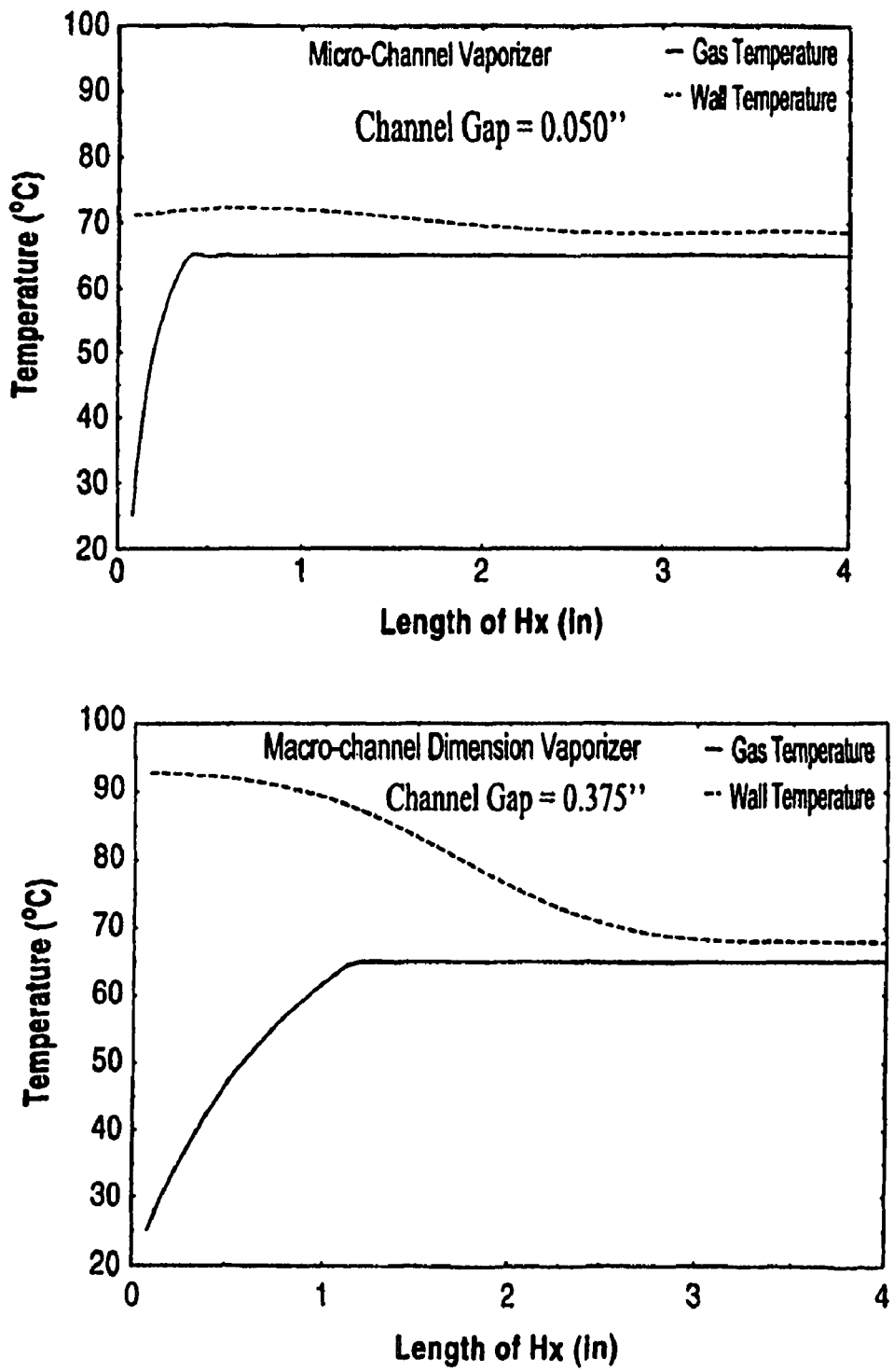
FIG. 30*a*. Wall and fluid temperature profile in microchannel vaporizer
FIG. 30*b*. Wall and fluid temperature profile in macrochannel vaporizer

FIGS. 30 a) and b) shows the temperature profile in the vaporizer (wall and fluid temperature) from inlet to outlet of the channel for Case 1 and Case 2 respectively. For both cases, the outlet quality of vapor is the same. The small temperature difference between wall and the fluid helps prevents film boiling regime and prefers convective or nucleate boiling regime. Film boiling is generally marked by vigorous evaporation of the liquid which may lead to non-uniform and difficult to control process. On the other hand, convective boiling or nucleate boiling are easier to control and provides stable process in terms of temperature, pressure and quality variations. Thus micro-channel dimension vaporizer will provide more stable boiling than conventional macro-channel dimension vaporizer.

Figure 31:
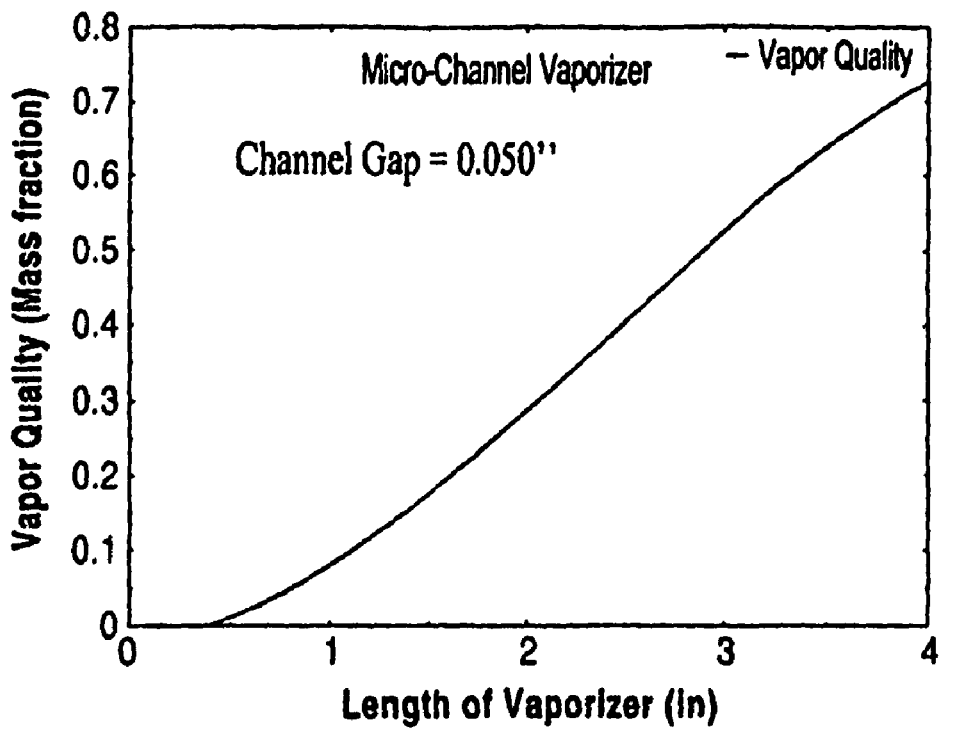
FIG. 31*a* Vapor quality profile in micro-channel vaporizer
FIG. 31*b* Vapor quality profile in macro-channel vaporizer
Figure 31:
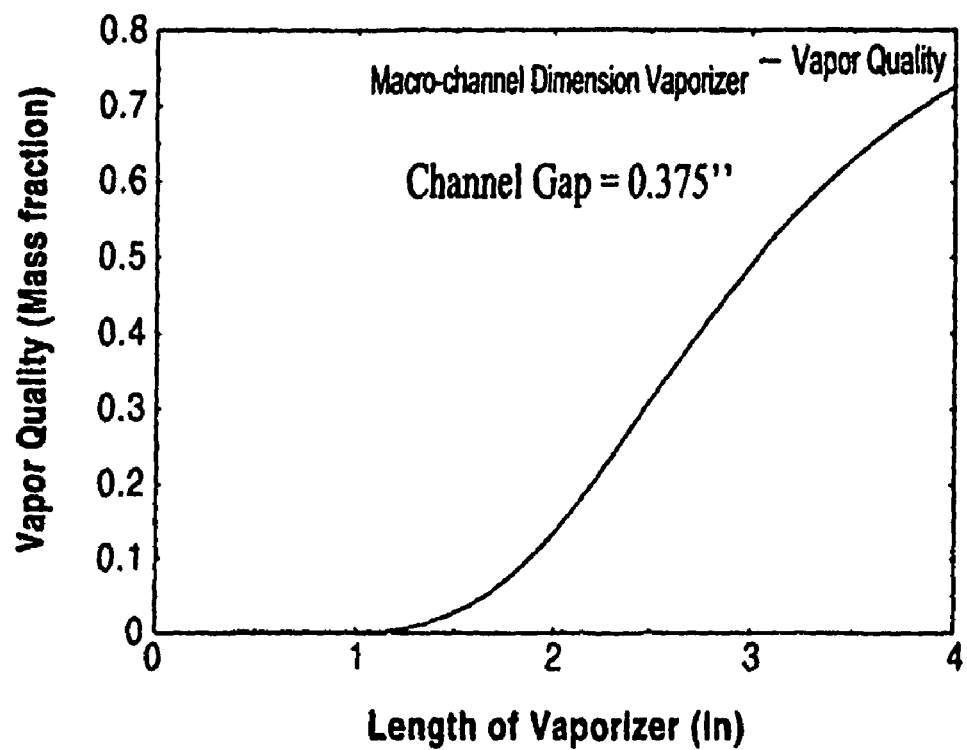

FIGS. 31 a) and b) shows the vapor quality profile along the channel length for Case 1 and Case 2 respectively. For both cases the outlet vapor quality is same 0.73 but there is a difference between the rate of vaporization. Microchannel vaporizer has a smoother and gradual vaporization while macro-channel vaporizer has sudden and steep vaporization. These results may imply that micro-channel dimensions leads to stable vaporization as compared to macro-channel dimensions.

The Boiling number for Case 1 is 0.005 and the SR number for Case 1 is 5×10⁻⁶. The boiling number and SR number for case 2 is 0.029 and 0.021 respectively.

EXAMPLE 8

Small Bubbles under High Shear Rate near the Heated Walls

Figure 32:
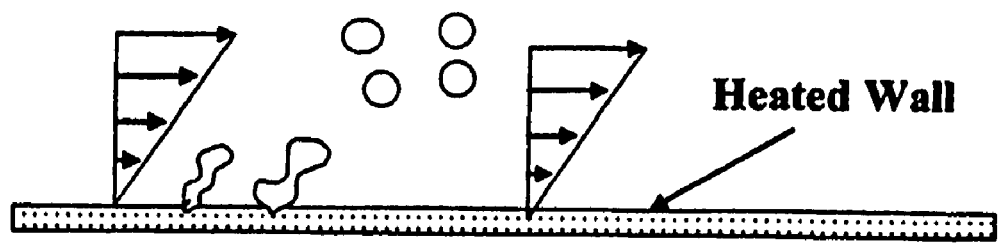
FIG. 32 Small bubbles are generated in micro-channels
Figure 33:
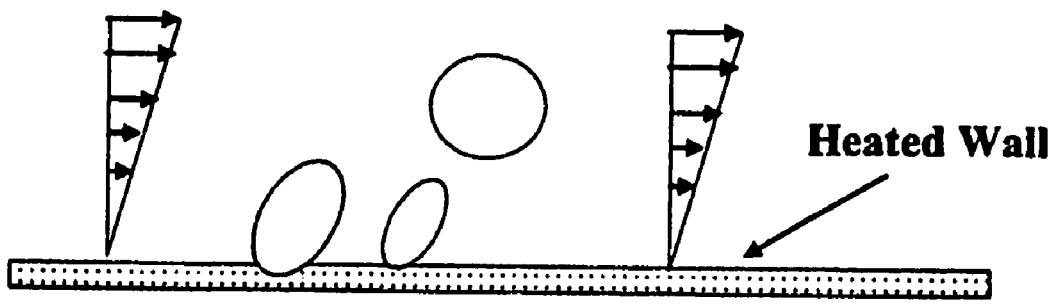
FIG. 33 Large bubbles are generated in large cooling channels

The high shear rate observed in the micro-channel facilitates the detachment of vapor bubbles from the heated wall. Before detachment, the bubbles grow in size near the walls, and deform under the shear rate. The higher the shear rate, the more severe the deformation of the bubbles. The net effect is that the bubbles will detach at smaller radius. See FIG. 32. Dispersion of small bubbles in the continuous liquid phase has high inter-phase surface area per unit volume of fluid which improves the heat transfer. Also higher dispersion rate can be achieved with the small bubble size. The flow is more stable without the collision between bubbles which cause flow fluctuations.

Flow boiling heat transfer is optimized when the regime is nucleate boiling and the bubbles are detached from the surface formation sites while still very small since small bubbles maximize interphase heat and mass transfer. The effects of flow conditions on bubble detachment in slit microchannels have been studied experimentally. Generally, higher velocity gradients exist at the channel wall for microchannels as compared to their conventional counterparts. This in turn leads to larger values of wall shear stress which serves to "clip off" or detach the bubbles more rapidly during formation for given conditions (e.g., wall superheat, average heat flux, etc.). The studies (e.g., Journal of Colloid and Interface Science 241, 514-520 (2001)) show that the critical flow parameters for bubble detachment are a function of channel height as well as the bubble's contact diameter. The required average fluid velocity (the Capillary number) decreases for larger bubbles and the slope of this relationship was seen to decrease as channel height decreased. In general, less fluid velocity is required to detach similar-sized bubbles in a channel of smaller height (gap). Therefore, by virtue of their inherently small channel gap sizes, microchannels can generate smaller bubbles for the same flow and heat conditions.

EXAMPLE 9

Stable Bubbly Flows at High Dispersion

Under partial boiling conditions in the micro-channels, the vapor bubbles are generated on the super-heated surfaces, then they detach from the surfaces and migrate into the fluid body. There exists a section of micro-channel where bubbles are dispersed in the continuous liquid phase. The interaction between these bubbles has direct impact on the heat transfer performance and two phase flow stabilities. Within microchannels the impact of the channel walls on the flow field is more dominant, and the shear rate across the channel width is at a high level. This high level shear rate prevents the growth of the bubbles and deformation and eventually breakup occurs for the bubbles above critical size, with the critical bubble radius being a function of shear rate as well as interfacial tension and fluid viscosity. The high shear rate reduces the critical bubble radius. The micro-channel walls regulate the flow field in between. The streamline is dominantly parallel to the walls. The flow is dominantly laminar.

EXAMPLE 10

Wetting Enhancement Structures

The surface heat flux requirement for boiling can be reduced significantly if the thickness of liquid film on the heated surface can be reduced. Though micro-channels provides thin liquid films inside the channels, however the liquid film thickness can be further reduced by using structures such as fine meshes, screens etc. These structures help liquid spread out on larger surface area, thus reducing the thickness of liquid film on the surface. The thin liquid film will require small surface heat flux for vaporization, thus these structures can help achieve partial boiling with low surface heat fluxes. Some examples of these structures are but not limited to expanded metal foils, wire mesh screen, cotton cloth, sintered metals, metal foams, polymer fibers, grooved surfaces (Triangular grooves (i.e. Fresnel lens), rectangular grooves, circular grooves) or any wetting, porous material.

In an alternate embodiment, surface features may also be used to enhance surface area for boiling. The size of the surface features either recessed or protruded from the wall may also be smaller than the hydraulic diameter of the microchannels. The smaller dimensionality may enable the formation of smaller bubbles than on a flat wall. In addition, flow advects within the surface features and as such there is a reasonable shear stress of the fluid against the wall surface. The shear stress within the surface features may be less than the shear stress on an analogous flat channel wall whose cross section intersects the top of the surface features. The magnitude of the shear stress in the surface feature may be 10% of the flat channel, and in some embodiments 50% or more of the comparable flat channel. The shear stress of fluid against the boiling wall in surface features is much higher than the shear stress found from other enhanced surface area structures as described in the literature because flow has minimal advection within the enhanced surface area regions as described in the literature.

EXAMPLE 11

Surface Roughness

Surface roughness and micropore structure within a microchannel has a dramatic effect on nucleate bubble formation. Surface roughness features generate perturbations in the flow field at the surface of the channel which in turn generate potential nucleation sites for bubble formation. Therefore, on a volumetric basis, there are more nucleation sites available in a microchannel application.

Surface roughness relative to the channel hydraulic diameter, $\in/D_H$, where $\in$ is the average height of the surface roughness and $D_H$ is the hydraulic diameter of the channel, is generally greater than that of conventional channels. Surface roughness can be measured by a profilometer, a stylus device used to trace across the surface profile. The results are expressed either as RA, which is the arithmetic average deviation from the center line of the surface, or as RMS, which is the root mean square of the deviations from the center line. RA or RMS values are given in either microns (same as micrometers or µm) or micro-inches (µ"). RMS will be approximately 11 percent higher than the RA number for a given surface. (RA×1.11=RMS). On most surfaces the total profile height of the surface roughness, or the peak-to-valley height will be approximately four times the RA value. A table of values for surface roughness in sanitary grade stainless steel pipes of all diameters is given below in Table 5.

TABLE 5

Surface Roughness Values for Sanitary
Grade Stainless Steel Pipes

| RMS (microinch) | RMS(μm) | RA (microinch) | RA (μm) | Grit Size |
|---|---|---|---|---|
| 80 | 2.03 | 71 | 1.9 | 80 |
| 58 | 1.47 | 52 | 1.32 | 120 |
| 47 | 1.2 | 42 | 1.06 | 150 |
| 34 | 0.6 | 30 | 0.76 | 180 |
| 17 | 0.43 | 15 | 0.38 | 240 |
| 14 | 0.36 | 12 | 0.3 | 320 |

These values are the average data of many tests considered accurate to within ±5% from *Bulletin on Material Welds and Finishers* by DCI, Inc. (Meltzer 1993)

These values are the average data of many tests considered accurate to within ±5% from *Bulletin on Material Welds and Finishers* by DCI, Inc. (Meltzer 1993)

Based on the values given in Table 5, the maximum value for $\in/D_H$ for a conventional system would be 2.03 micron/10 mm~$2\times10^{-4}$ m. However, based on experimentally determined surface features in microchannels (Wu and Cheng: 2003 and Honda and Wei: 2004) values for $\in/D_H$ can be at least one order of magnitude greater (~$10^{-3}$ m).

Engineered features in the surface of a microchannel can also enhance nucleate boiling. Among the geometrical parameters, the pore diameter was found to be most influential on the bubble departure diameter. It has been demonstrated experimentally (Ramaswamy et al., 2002) that there are distinct boiling regimes for enhanced structures similar to that for plain surfaces. For low to intermediate wall superheat values (4-12° C.), boiling took place in the isolated bubble regime. As wall superheat increases, bubble coalescence can begin to take place. The net result of this phenomenon is to create larger vapor bubbles which in turn lead to lower interphase heat transfer and reduced overall performance of the system. The coalescence phenomenon, however, can be controlled to some extent by varying the pore pitch. A slotted surface can assist nucleation. Other patterned surfaces can also be useful, such as a grid of subchannels on a wall or walls of a coolant channel.

In general, the average bubble departure diameter decreases with a decrease in the pore size (for constant wall superheat).

There is a primary reason why these enhancement features for nucleate boiling prove more successful in microchannel rather than conventional-sized channels. In most cases, the flow in a microchannel is laminar and the boundary layer occupies the full extent of the channel gap. With these enhancement features employed, the nucleate boiling can be increased throughout the entire boundary layer and hence throughout the entire cross-section of the microchannel flow. However, in a conventional channel application, the boundary layer (laminar or turbulent) occupies only a small percentage of the overall flow volume. Thus, enhancement features of this type will have relatively little impact on their performance.

EXAMPLE 12

Flow Distribution

For microchannel systems that have open manifolds connecting plural cooling channels, the invention may include flow control mechanisms such as described in U.S. patent application Ser. No. 10/695,400, published as 2005/0087767 which is incorporated by reference as if reproduced in full below, and from which FIGS. 34*a* and *b* have been copied.

Barriers with uniformly distributed obstacles aligned in parallel with the connecting channel matrix can change the pressure loss to enter a matrix of connecting channels through turning and sudden expansion losses for sub-cooled or saturated liquids. The barriers can include, but aren't limited to, orifice plates, screens, grids, ordered filter material, and gratings. To achieve different flows into a set of microchannels, barriers with different flow resistances can be placed into manifold to tailor the flow to the microchannels as needed, though it is important to seal the sections downstream of the barrier from each other to avoid cross-channel leakage.

Barriers with uniformly distributed obstacles (barriers can create orifices) aligned in the header can create a pressure loss from a change in cross-sectional area in the direction of the header flow, which is at a nonzero angle with respect to the connecting channel matrix. This lowers the local pressure for driving the fluid across the connecting channels. This barrier can be an alternative to distributed obstacles parallel to the connecting microchannels, but could also be used along with the obstacles.

Barriers with uniformly distributed obstacles aligned parallel with the connecting channel matrix used to add a higher pressure drop loss with higher fluid equilibrium quality. The higher the quality the higher the stream's momentum and the higher pressure drop the stream has for passage through the barrier. This barrier is very effective for microchannel arrays that remove a constant heat flux from each channel. The barrier can be fixed to the outlet or inlet of the channels to equalize local flow rates through the coolant channel matrix (such as a planar array of parallel channels having 2, 5, 10 or more planar, parallel channels.

In open manifold systems, there can be room to place and fixture these external-to-the-microchannel passive manifold structures.

An orifice plate design (see FIGS. 34*a* and 34*b*) can be used to meter flows to many parallel individual microchannels. The flow rate varies in the different cooling channels from top to bottom in the figures to accommodate the non-uniform heat flux profile on the walls in process flow direction. The flow distribution through the orifices is predicted by a flow resistant network approach and also using a computational fluid dynamics tool. In the one embodiment in FIGS. 34*a* and *b*, the following rules are used:

1) The temperature of the solid channel wall separating the process side and the coolant side should be maintained at a nearly constant value of 160° C. in order to create an isothermal boundary condition for the vinyl acetate monomer reaction. This is realized via flow boiling of water under pressure about 6 atmospheres.

2) In order to achieve an economic operation, the pumping power of the coolant loop should be minimized and the steam equilibrium quality of the coolant at exit should be maximized. As such, the overall pressure drop and the total flow rate of the coolant should be minimized under the condition such that hot spots and dry out do not occur in coolant channel under all operating conditions.

Based on a selected VAM reaction model, the maximum heat flux at the reactor top (near the beginning of reaction zone) is approximately as large as ten times of the heat flux at the bottom. This type of profile requires an unequal coolant flow rate distribution as shown in the same figure under the condition of an exit steam quality of 0.3 that is determined from the Critical Heat Flux (CHF) of flow boiling. This means that at the given local heat flux and the exit quality the flow rate prevents a local hot spot or coolant dryout to occur.

Figure 34A:
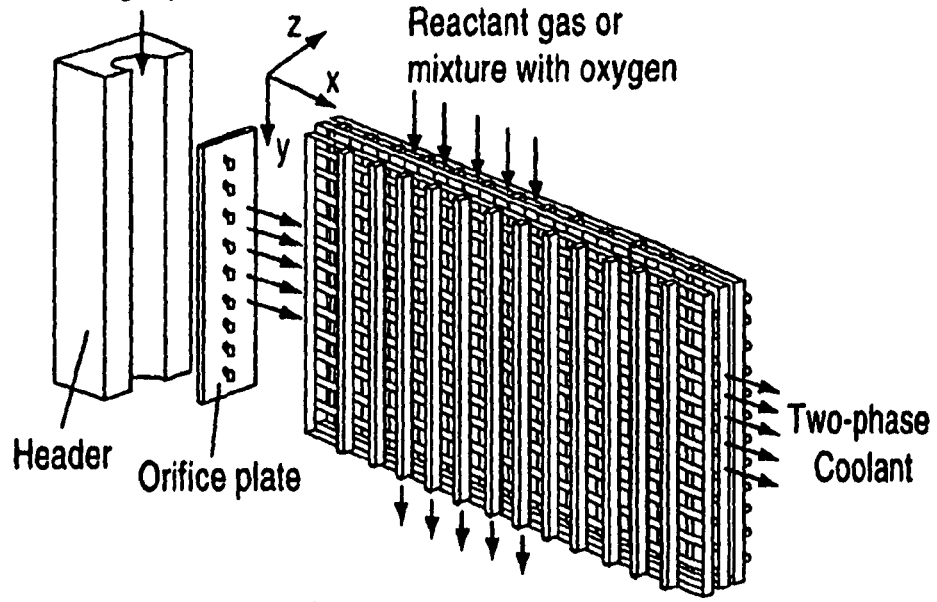
FIG. 34*a*. Configuration and flow arrangement of a multi-channel reactor
Figure 34B:
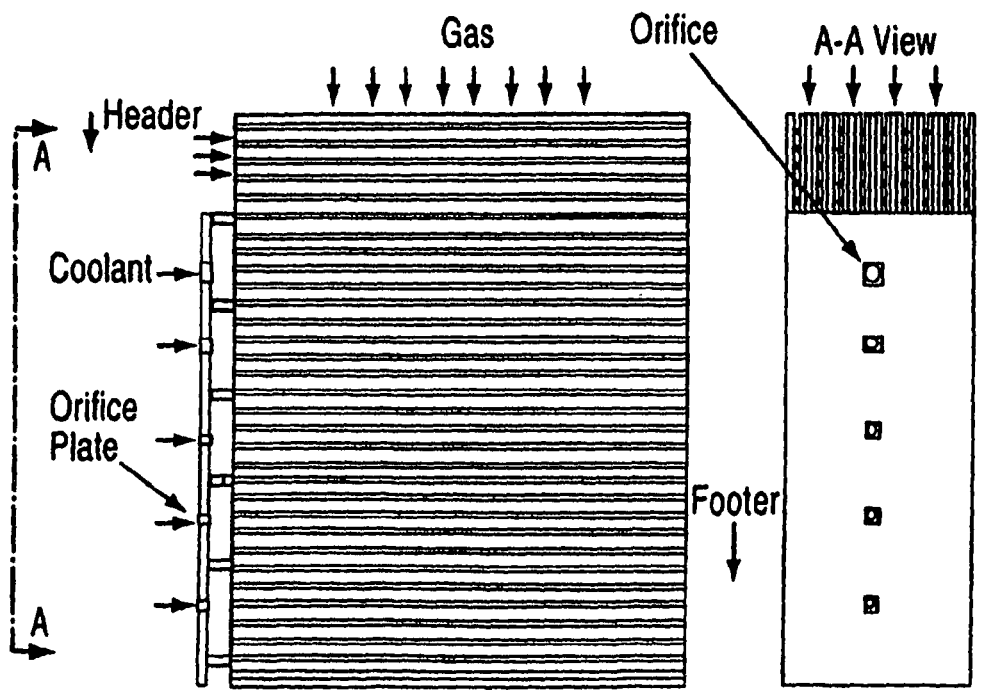
FIG. 34*b*. An example of the external orifice plate in the header
Figure 35:
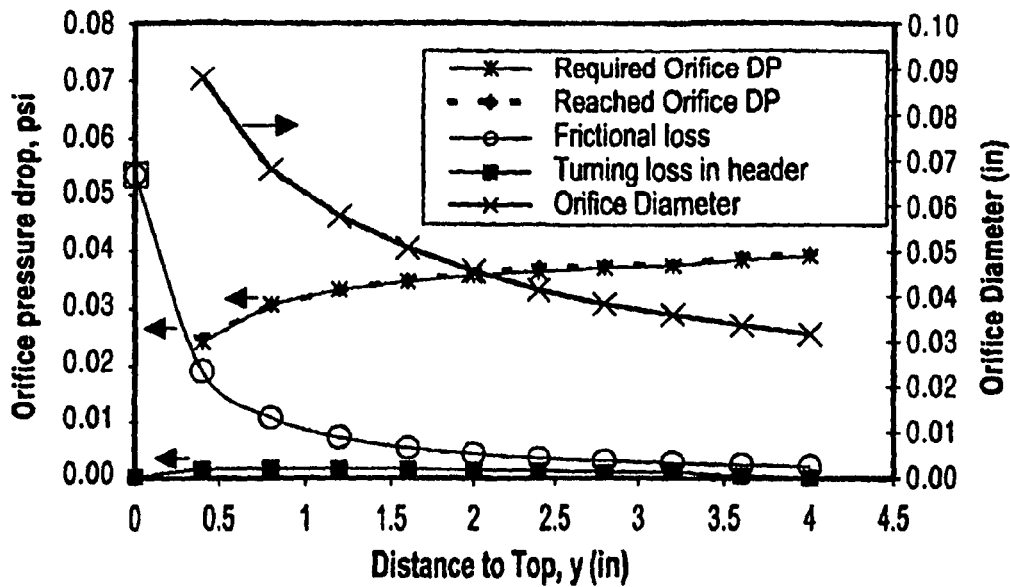
FIG. 35: Pressure drop and orifice diameter at given heat flux profile for exit quality X=0.3

By placing an orifice plate with different hole sizes at the inlets (header) to the channels, the same total pressure drop including the pressure loss in the header can be reached for the channels at the required flow rates. If for each channel a separate orifice were made, the orifice diameter would be very small (<0.1 mm) at small Reynolds number, especially if the length of the orifice is short, e.g. less than 1 mm. Due to the microscale and the large number (for example, 300) of the channels, the fabrication including the alignment would be not realistic. Thus, a configuration of orifice plate with few orifices has been designed, see FIGS. 34a and b, where as a function of the orifice diameter the frictional loss, turning losses from the manifold, and pressure drops are calculated. Each orifice is responsible for a group of channels so that the orifice sizes are large enough to be fabricated in a regular way and the flow regime in the orifices is turbulent that is suited for controlling the flow rate. FIGS. 34a and b show the orifice size distribution of the orifice plate, the total pressure drop from coolant inlet in the header to the outlet of footer and the pressure loss across the orifices.

EXAMPLE 13

Design of a Chemical Reactor with Partial Boiling for Temperature Control

Partial boiling in microchannels adjacent to an exothermic chemical reactor (Fischer-Tropsch synthesis) has been evaluated to control the reactor temperature such that the overall productivity is held high while concurrently minimizing production of by-products. The temperature in the partial boiling chambers is near isothermal, with a temperature differential less than 10° C. across the reactor, and more preferably less than 5° C. across the reactor.

In this example, flow is controlled into a array of parallel microchannels through the use of a restrictive orifice at the entrance of each channel to create sufficient pressure drop to meter the flow to each channel in a uniform or tailored manner. Alternative methods of distributing flow into an array of channels (typically parallel channels) is described in the previously referenced patent application which is incorporated herein by reference; such methods may include the use of submanifolds within a manifold, porous media to control flow to or within channels, or differing sized gates to regulate flow into channels.

The partial boiling fluid may flow horizontally or vertically in an upflow or downflow orientation. The upflow orientation may be preferred as this would remove the issue of the hydrostatic head pressure of water in the manifold contributing to flow maldistribution. In other embodiments, an upflow of water or other fluid for partial boiling may be challenging for some reactions, such as FT synthesis, where the reaction mixture is also multiphase and a downflow orientation may be preferred.

The FT reactor described in this example contains two parts to the process microchannels, where the top half of the process channel has a process gap of 0.1016 cm (0.04 inches), and the bottom half of the process microchannel contains a process gap of 0.3048 cm (0.12) inches. Two top half 0.1016 cm (0.04 inches) channels feed into one bottom half microchannel. The two top half process microchannels are separated by heat exchange channels, where partial boiling for heat extraction occurs. A step is defined as the region where the two process microchannels of the top half join with the one process microchannel of the bottom half. The intent of the step is to create more volume for process microchannel catalyst where the volumetric production of heat has decreased from the higher level created near the reactor inlet (with fresh feeds and the highest reactant concentration).

Using one dimensional models for mass, energy and momentum, the coolant stream distribution, temperature profile and pressure drop during reactor operation were described for the application of partial boiling of water to control the reaction temperature for Fischer-Tropsch synthesis.

A cooling channel and manifold system were design based on the heat flux profile from the F-T reaction when operated at a contact time of 350 ms. The reactor productivity is estimated at 0.08 barrels of FT liquid per day. The FT reactor also contained a mixture of catalyst and high thermal conductivity inert material in part of the reactor. The results show that at a pump rate of 3.0 liters per minute (LPM) at 20° C., the wall temperature across the coolant section is predicted to be controlled to a 224.2° C. to 225° C. range, surprisingly a range of less than 1° C., assuming 355 psig and 224° C. header inlet conditions, insulated perimeters and 0.2794 cm (0.011 inches) ID half circle orifices in each channel opening to the 0.05588 (0.022 inches)×0.254 cm (0.10 inches) array of parallel microchannels where boiling occurs adjacent to the FT reaction in interleaved microchannels.

Flow rates lower than 3.0 LPM result in higher outlet quality in the footer that lowers the footer overall density, making the pressure increase from the top of the footer manifold to the bottom less than in the all liquid header. Lower total flows into the header also result in lower orifice pressure losses in entering sections in the "step" have more flow than in the upstream section in a monotonic change driven by differences in the local hydrostatic pressure difference between the header and footer. That distribution bias coupled with constant heat input gives rise to higher quality in channels of the upper sections, further adding flow resistance and maldistribution. The model predicts backflow for pumping rates below 1.0 LPM, which has a predicted exit mass quality of 5%, so the recommendation is to operate at 3.0 LPM with an approach temperature to saturation down to 1° C.

Figure 36:
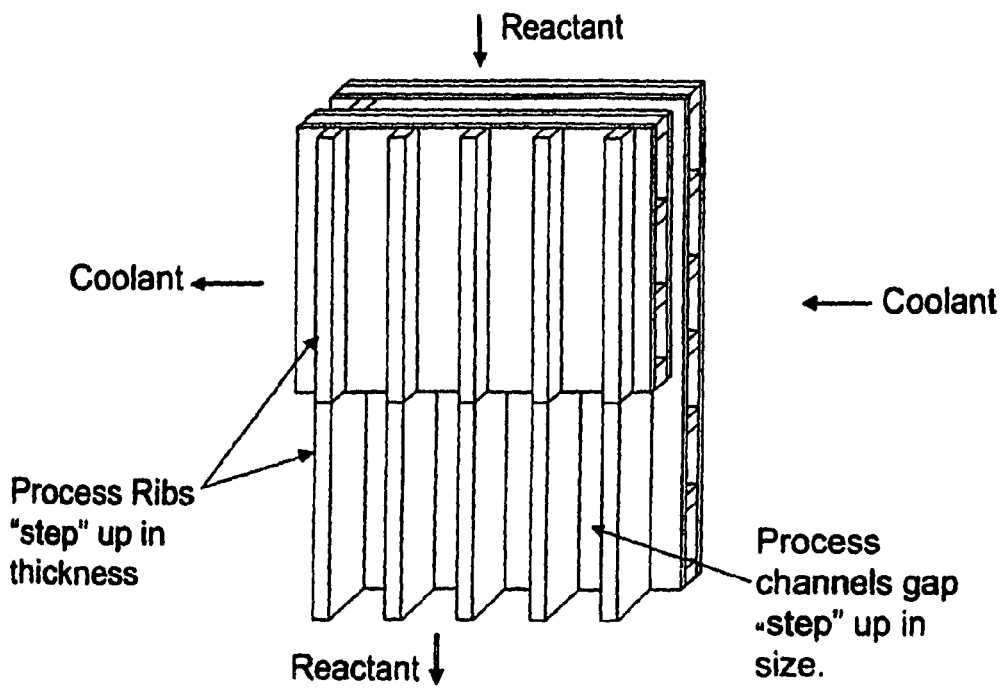
FIG. 36: Cross flow reactor

FIG. 36 illustrates reactor geometry, where coolant is cross flow in microchannels and process flow is from top to bottom (aligned with gravity). The process channels are narrower at the top of the reactor and become wider near the bottom of the reactor. There are more cooling channels near the top of the reactor than near the bottom of the reactor. This design requires a horizontal manifolding system for the coolant stream, in this case water that partially boils in the coolant channels.

Assumptions and References
Model Geometry

Figure 37:
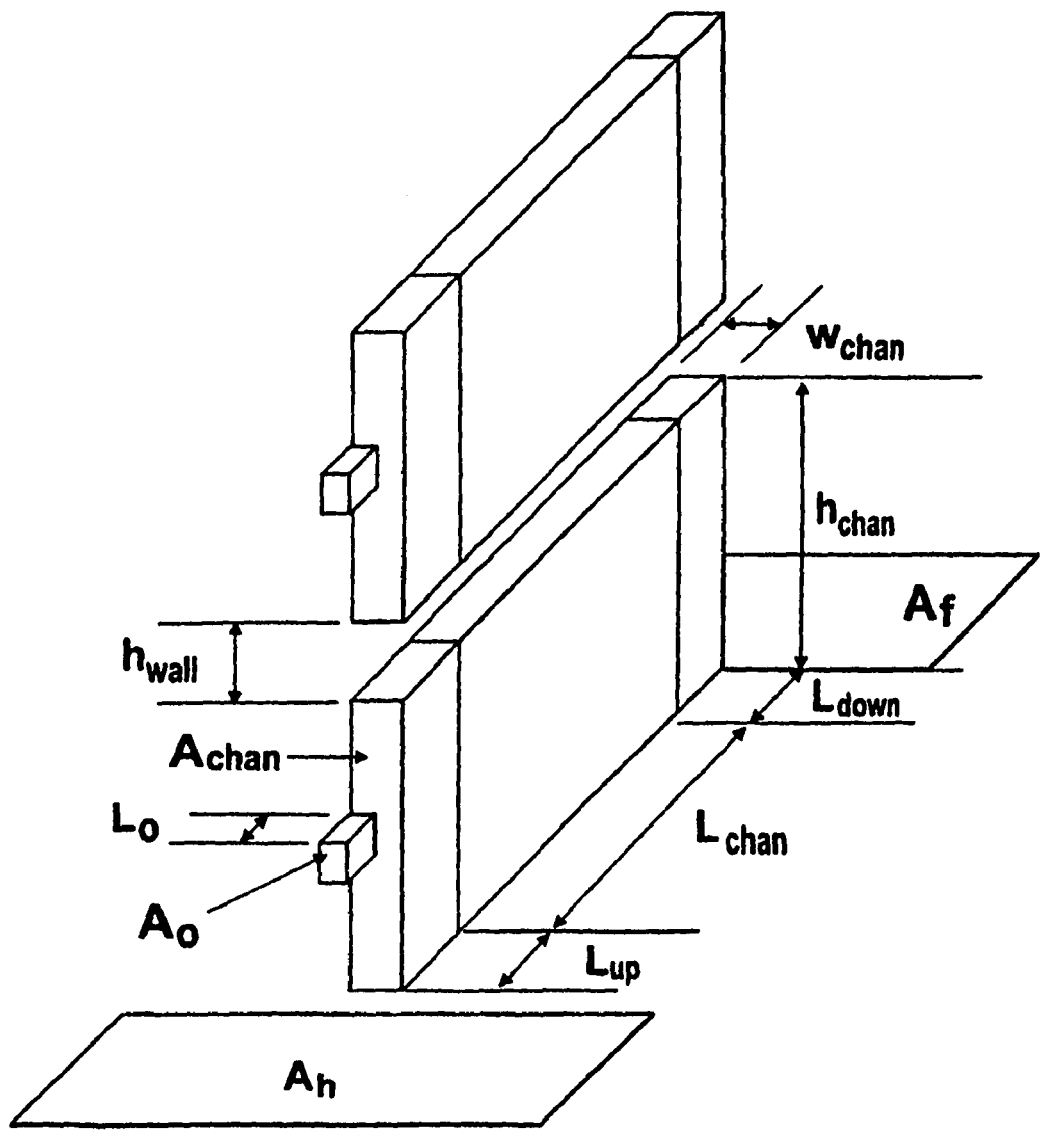
FIG. 37. Definitions and channel dimensions of the model, not drawn to scale.

FIG. 37 shows a schematic of the channels and the important dimensions.

The coolant manifold has one hundred and seventy (170) 0.05588 cm (0.022 inches) wide by 0.254 cm (0.100 inches) tall coolant channels for the end channel columns and 83 channels in the "Step" channel column. There are 0.030" tall ribs separating the channels. The total modeled height of the header and footer column is 170×(0.100"+0.030")=22.100".

The orifice opening is a 0.011" diameter half circle, which has been experimentally tested in the single channel boiling device. The purpose of the orifice is to create a higher pressure drop in the orifice at the inlet to the cooling channel than the pressure drop through the channel during partial boiling operation. By this manner, the flow is controlled to each of the hundreds of cooling channels. This orifice channel extends 0.050" in length and opens up to the main channel cross-section described in the preceding paragraph. The upstream section of the channel before the main heat exchanger section is 0.700" in length. The heat exchanger section then extends 11.500" in length. The downstream section of the channel is 0.750" in length prior to the footer.

The header and footer cross-sectional area sections are taken as a 0.925" diameter half circle extending from a 0.75" long by 0.925" wide rectangle, which interfaces the coolant channels.

The goal is to obtain constant wall temperature, high heat removal and robust flow (i.e. stable operation) for a coolant loop. A model based upon experimental findings allows the design for operation to be made to remove a heat load of 2750 W/m2 in the top half of the manifold and 6500 W/m2 in the bottom half. Sub-cooled water enters the header from its top and leaves the footer out the bottom.

Figure 38:
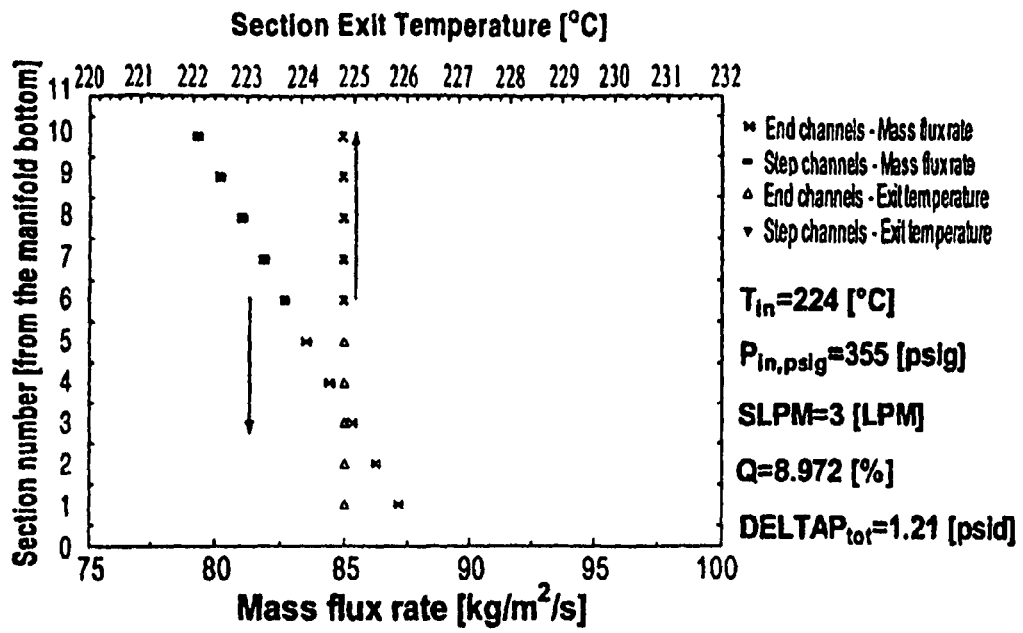
FIG. 38. Section channel mass flux rates (lower x-axis) and exit temperatures (upper x-axis) for a case (3.0 LPM).

This coolant loop has a number of heat removal channels arranged vertically with a header and footer of 0.56 meters in height arranged vertically to gravity. The fluid was brought in at high pressure (355 psig) and 224° C., just below the saturation temperature of 225° C. By using 0.02794 cm (0.011 inches) diameter half circular orifices in each channel and an average outlet mass quality of 0.02, the channel to channel quality index factor was 9%. The exit temperatures were all 224.8° C. FIG. 38 shows the average channel mass flux rate (bottom axis) and average exit temperatures of the manifold (top axis) plotted versus the section number, ordered with the first set of seventeen channels as section 1 and the last set of 17 channels in section 10. There is a tendency for the flow to bias toward the bottom sets of channels which is driven by the lower hydrostatic pressures difference from the top to the bottom in the vapor containing footer compared to the header.

Figure 39:
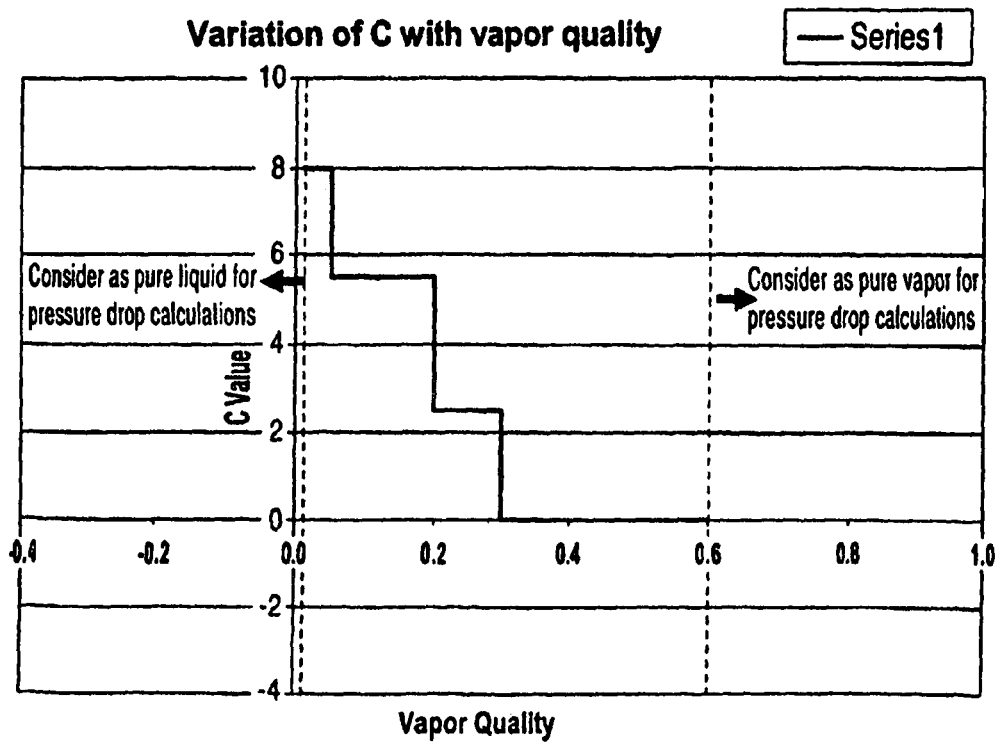
FIG. 39: Variation of Lockhart-Martenelli C factor with quality

This design can have a good flow distribution due to the pressure losses in the orifice add sufficient flow resistance. This was necessary, as the pressure drop losses for the 29.21 cm (11.5 inches) long channel is fairly small at this pressure. FIG. 39 shows the Lockhart-Martenelli constant C versus mass quality fraction, and the constant drops from 8 at X=0.01 to zero by X=0.3, with the pressure drop best described by single phase gas pressure drops for mass quality fractions greater than 0.6.

Figure 40:
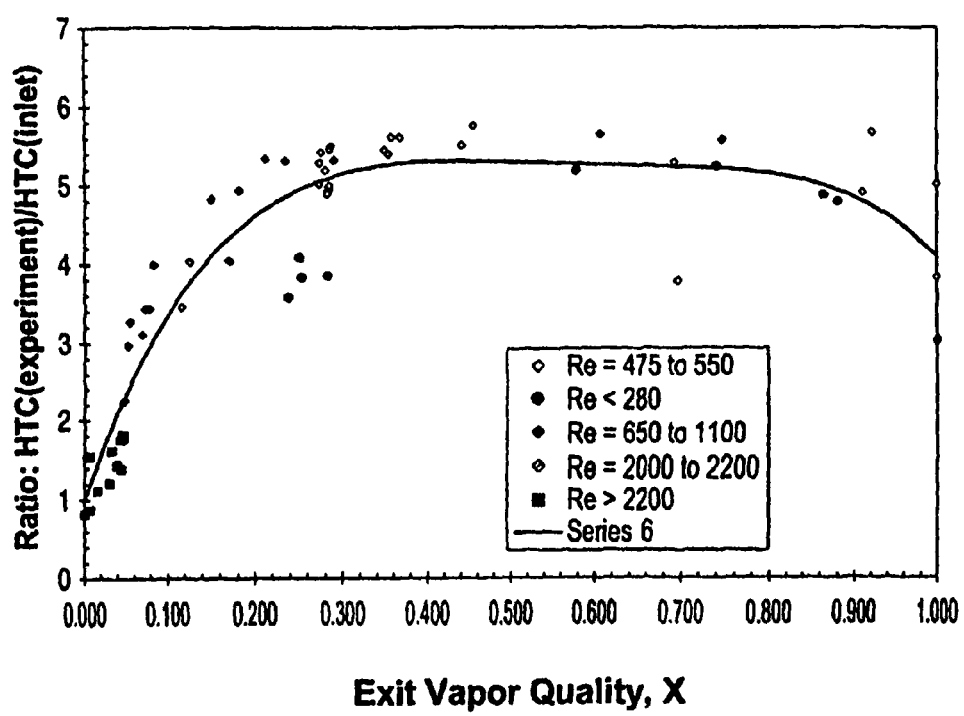
FIG. 40. The ratio of the measured heat transfer coefficient to the single phase inlet heat transfer coefficient plotted versus channel exit quality.

The manifold can maintain a 225° C. wall temperature well because the convective heat transfer coefficient sees a substantial increase in just a small outlet mass quality fraction. FIG. 40 shows the ratio of the experimentally obtained heat transfer coefficient to that of the single phase liquid heat transfer coefficient at the inlet temperature. The ratio increases quickly from unity at mass quality fraction of 0.01 to almost 5 by X=0.2. Thus the advantages of the convective boiling heat transfer can be obtained at low mass quality fractions.

We claim:

1. A process of removing heat from an exothermic process, comprising:
    conducting an exothermic process in a process channel;
    removing heat from the exothermic process in the process channel to an adjacent minichannel or adjacent microchannel;
    wherein the adjacent minichannel or adjacent microchannel comprises an interior wall surface that is a surface on a channel wall that separates the adjacent minichannel or adjacent microchannel from the process channel; wherein the adjacent minichannel or adjacent microchannel comprises a barrier at an entrance area of the minichannel or microchannel, wherein the adjacent minichannel or adjacent microchannel comprises a cross-sectional area perpendicular to flow through the minichannel or microchannel, and wherein the barrier creates an opening in the direction of flow through the minichannel or microchannel that is greater than 10% of the cross-sectional area of the minichannel or microchannel;
    passing a coolant fluid through the adjacent minichannel or adjacent microchannel at an average shear stress of the fluid at the wall in the adjacent minichannel or adjacent microchannel for a length of at least 1 cm, either measured or calculated, of at least 1 Pascals (Pa); and
    partially boiling the coolant fluid for a length of at least 15 cm as it passes through the adjacent minichannel or adjacent microchannel.

2. The process of claim 1 wherein the adjacent minichannel or adjacent microchannel is a microchannel having a hydraulic diameter of 2 mm or less.

3. The process of claim 2 wherein the average shear stress of the fluid at the wall in the adjacent microchannel for a length of at least 1 cm, is at least 10 Pascals.

4. The process of claim 2 wherein the average shear stress of the fluid at the wall in the adjacent microchannel for the entire length of the adjacent microchannel, is at least 10 Pascals.

5. The process of claim 1 comprising:
    controlling pressure of the coolant fluid in the adjacent minichannel or adjacent microchannel using a pressure controller or stabilizer located downstream of the adjacent minichannel or adjacent microchannel where partial boiling is occurring.

6. The process of claim 3 wherein the process channel has a hydraulic diameter of 10 mm or less.

7. The process of claim 1 wherein the adjacent minichannel or adjacent microchannel has a hydraulic diameter of 5 mm or less.

8. The process of claim 2 wherein the coolant fluid enters the adjacent microchannel at a temperature of at least 5° C. less than the boiling temperature at the conditions in the microchannel.

9. The process of claim 6 wherein partial boiling in the adjacent microchannel occurs over a length of at least 50 cm.

10. The process of claim 7 wherein the adjacent minichannel or adjacent microchannel has an aspect ratio of at least 5.

11. The process of claim 1 wherein the adjacent microchannel comprises an inlet and an outlet, wherein the microchannel has a larger cross sectional area near the inlet, where the coolant fluid isn't boiling, than in a region further downstream where the coolant fluid is boiling.

12. The process of claim 2 wherein the adjacent microchannel is disposed horizontally with respect to gravity.

13. The process of claim 1 comprising plural coolant microchannels connected to a common manifold, and
    wherein each of said plural microchannels comprise an barrier, wherein, other than the barrier, each of said plural microchannels has essentially a constant cross-sectional area, wherein said plural microchannels each have essentially the same cross-sectional area, and wherein the barrier in each of said plural microchannels creates an orifice that is at least 40% as large as the average cross-sectional area of each of said plural microchannels.

14. The process of claim 1 wherein the temperature in the length of at least 15 cm in the adjacent minichannel or adjacent microchannel varies by no more than 3° C.

15. The process of claim 1 wherein the average shear stress of the fluid at the wall in the adjacent minichannel or adjacent microchannel for a length of at least 15 cm, either measured or calculated, is at least 10 Pascals (Pa).

16. The process of claim 1 comprising a planar array of process channels and an adjacent planer array of the minichannels or microchannels wherein each of the minichannels or microchannels in the adjacent planar array comprises a barrier at an entrance area of the minichannel or microchannel, wherein the barrier creates an opening in the direction of flow through the minichannel or microchannel that is at greater than 40% of the cross-sectional area of the minichannel or microchannel.

17. The process of claim 14 wherein the adjacent minichannel or adjacent microchannel is a microchannel having a length of at least 30 cm and further wherein pressure drop through the microchannel fluctuates by no more than 5% as measured by a pressure gauge at the channel outlet.

18. The process of claim 1 wherein the adjacent minichannel or adjacent microchannel has an aspect ratio of at least 10.

19. The process of claim 2 wherein pressure oscillation in the adjacent microchannel is 5% or less.

20. The process of claim 1 wherein the adjacent channel is a microchannel and wherein pressure drop in the microchannel is less than 0.3 psig/2.5 cm and wherein heat flux at the interior wall surface is at least 2 W/cm$^2$.

21. The process of claim 1 wherein the adjacent channel is a microchannel having a length of at least 30 cm and wherein pressure drop fluctuations are no more than 5% as measured by a pressure gauge at the channel outlet.

22. The process of claim 1 wherein the exothermic process comprises the Fischer-Tropsch reaction that has a methane selectivity of less than 15%.

23. The process of claim 16 wherein coolant passes through each of the minichannels or microchannels and undergoes partial boiling in each minichannel or microchannel in the adjacent planar array of the minichannels or microchannels.

24. The process of claim 23 wherein flow of coolant in the adjacent planar array of the minichannels or microchannels is cross-flow relative to flow in the planar array of process channels.

25. The process of claim 23 wherein the planar array of minichannels or microchannels are connected to a common manifold.

26. The process of claim 1 wherein the adjacent channel has a width to height ratio of at least 5.

27. The process of claim 1 wherein the barrier creates an opening in the direction of flow through the minichannel or microchannel that is greater than 50% of the cross-sectional area of the minichannel or microchannel.

28. The process of claim 1 wherein the exothermic process is an exothermic reaction comprising: Fischer-Tropsch reaction; alkylation; oxidation to an oxygenate or nitrile; dimerization; polymerization; hydrogenation, hydrodesulfurization, hydrotreating, or hydrocracking; or direct combination of hydrogen and oxygen to hydrogen peroxide.

29. The process of claim 1 wherein the adjacent channel is a microchannel, wherein the exothermic process is an exothermic reaction comprising a catalyst and the contact time is less than 300 ms, and wherein temperature along the process channel rises by less than 5° C.

30. The process of claim 1 wherein the adjacent channel is a microchannel, wherein the exothermic process comprises a phase change, and wherein temperature along the process channel rises by less than 10° C.

31. The process of claim 1 wherein the adjacent channel is a microchannel, wherein the exothermic process comprises mixing.

32. The process of claim 2 comprising more than 10 coolant microchannels connected to a common manifold, and having a flow distribution quality factor of less than 20% in said more than 10 coolant microchannels.

33. The process of claim 2 wherein coolant passing through the adjacent channel undergoes stable, partial boiling and wherein the adjacent channel has a length to hydraulic diameter ratio equal to or exceeding 1000.

34. The process of claim 23 comprising a pressure controller or stabilizer located downstream of the array of microchannels.

35. The process of claim 1 wherein the adjacent minichannel or adjacent microchannel comprises patterned surfaces.

36. The process of claim 1 comprising plural coolant microchannels connected to a common manifold, and
wherein each of the microchannels comprises a barrier at an entrance area of the microchannel, wherein the barrier creates an opening in the direction of flow through the microchannel that is at greater than 40% of the cross-sectional area of the microchannel; and
wherein the barrier in each of the microchannels has a length in the direction of flow of at least 50 μm.

\* \* \* \* \*